(12) United States Patent
Zuckermann et al.

(10) Patent No.: US 6,251,433 B1
(45) Date of Patent: Jun. 26, 2001

(54) POLYCATIONIC POLYMERS

(75) Inventors: Ronald N. Zuckermann; Nathalie Dubois-Stringfellow, both of Berkeley; Varavani Dwarki, Alameda; Michael A. Innis, Moraga; John E. Murphy, Oakland; Fred E. Cohen; Tetsuo Uno, both of San Francisco, all of CA (US)

(73) Assignee: Chiron Corporation, Emeryville, CA (US)

( * ) Notice: Subject to any disclaimer, the term of this patent is extended or adjusted under 35 U.S.C. 154(b) by 0 days.

(21) Appl. No.: 08/910,647

(22) Filed: Aug. 13, 1997

Related U.S. Application Data

(60) Provisional application No. 60/023,867, filed on Aug. 13, 1996.

(51) Int. Cl.$^7$ ...................................................... A61F 9/14
(52) U.S. Cl. ........................ 424/486; 424/450; 530/300; 530/333; 435/320.1; 525/54.1; 525/420
(58) Field of Search ................................... 424/490, 450, 424/484, 486; 559/105; 935/6, 52, 54, 66; 530/300, 333; 435/455, 458; 525/54.1, 420

(56) References Cited

U.S. PATENT DOCUMENTS

| | | | |
|---|---|---|---|
| 4,235,886 | * 11/1980 | Freidinger et al. | 424/177 |
| 5,041,497 | * 8/1991 | Bhattacharjee et al. | 525/54.11 |
| 5,334,761 | * 8/1994 | Gebeyehu et al. | 564/197 |
| 5,635,487 | * 6/1997 | Wolf et al. | 514/44 |
| 5,679,559 | * 10/1997 | Kim et al. | 435/455 |

FOREIGN PATENT DOCUMENTS

| | | |
|---|---|---|
| 544292 A2 | 6/1993 | (EP) . |
| 545016 A1 | 6/1993 | (EP) . |
| WO 91/19735 | 12/1991 | (WO) . |
| WO 94/06451 | 3/1994 | (WO) . |
| WO 95/02397 | 1/1995 | (WO) . |
| WO 95/28494 | 10/1995 | (WO) . |
| WO 95/31557 | 11/1995 | (WO) . |
| WO 96/18372 | 6/1996 | (WO) . |
| WO 96/22765 | 8/1996 | (WO) . |
| WO 96/27379 | 9/1996 | (WO) . |
| WO 97/11682 | 4/1997 | (WO) . |
| WO 97/12052 | 4/1997 | (WO) . |

OTHER PUBLICATIONS

Wagner et al., "DNA–Binding Transferrin Conjugates as Functional Gene–Delivery Agents: Synthesis by Linkage of Polylysine or Ethidium Homodimer to the Transferrin Carbohydrate Moiety" *Bioconjugate Chem.* 2(4):226–231, 1991.

Wagner et al., "Influenza Virus Hemagglutinin HA–2 N–terminal Fusogenic Peptides Augment Gene Transfer by Transferrin–Polylysine–DNA Complexes: Toward a Synthetic Virus–Like Gene–Transfer Vehicle" *Proc. Natl. Acad. Sci. USA* 89 :7934–7938, Sep., 1992.

Batra et al., "Receptor–Mediated Gene Delivery Emplyong Lectin–Binding Specificity" *Gene Therapy* 1 :255–260, 1994.

Behr et al., "Gene Transfer With Synthetic Cationic Amphiphiles: Prospects for Gene Therapy" *Bioconjugate Chem.* 5:382–389, 1994.

Michael and Curiel, "Strategies to Achieve Targeted Gene Delivery via the Receptor–Mediated Endocytosis Pathway" *Gene Therapy* 1:223–232, 1994.

Gao and Huang, "Potentiation of Cationic Liposome–Mediated Gene Transfer Delivery by Polycations" *Biochemistry* 35 :1027–1036, 1996.

Gao and Huang, "Cationic Liposome–Mediated Gene Tranfer" *Gene Therapy* 2 :710–722, 1995.

Guy et al., "Delivery of DNA into Mammalian Cells by Receptor–Mediated Endocytosis and Gene Therapy" *Molecular Biology* 3:237–248, 1995.

Kabanov and Kabanov, "DNA Complexes with Polycations for the Delivery of Genetic Material into Cells" *Bioconjugate Chem.* 6 :7–20, 1995.

Liu et al., "Cationic Liposome–Mediated Intravenous Gene Delivery" *J. Biological Chemistry* 270 (42):24864–24870, 1995.

Phillips, "Receptor–Mediated DNA Delivery Approaches to Human Gene Therapy" *Biologicals* 23 :13–16, 1995.

Remy et al., "Targeted Gene Transfer into Hepatoma Cells With Lipopolyamine–Condensed DNA Particles Presenting Galactose Ligands: a Stage Toward Artificial Viruses" *Proc. Natl. Acad. Sci. USA* 92 :1744–1748, Feb., 1995.

Lasic and Tenpleton, "Liposomes in Gene Therapy" *Advanced Drug Delivery Reviews* 20:221–226, 1996.

Tomlinson and Rolland, "Controllable Gene Therapy Pharmaceutics of Non–Viral Gene Delivery Systems" *J. Controlled Release* 39 :357–372, 1996.

Legendre et al., "Dioleoylmelittin as a Novel Serum–Insensitive Reagent for Efficient Transfection of Mammalian Cells" *Bioconjugate Chem.* 8 :57–63, 1997.

Behr et al., "The Proton Sponge: a Trick to Enter Cells the Viruses did not Exploit" *Chimia* 51 :34–36 (1997).

(List continued on next page.)

Primary Examiner—Dave Trong Nguyen
(74) Attorney, Agent, or Firm—LeeAnn Gorthey; David P. Lentini; Robert P. Blackburn

(57) ABSTRACT

This invention relates compositions and methods for increasing the uptake of polynucleotides into cells. Specifically, the invention relates to vectors, targeting ligands, and polycationic agents. The polycationic agents are capable of (1) increasing the frequency of uptake of polynucleotides into a cell, (2) condensing polynucleotides; and (3) inhibiting serum and/or nuclease degradation of polynucleotides.

9 Claims, 9 Drawing Sheets

OTHER PUBLICATIONS

Hong et al., "Stabilization of Cationic Liposome–Plasmid DNA Complexes by Polyamines and Poly(ethylene glycol-)–phospholipid Conjugates for Efficient in vivo Gene Delivery" *FEBS Letters* 400:233–237 (1997).

Merwin et al., "Targeted Delivery of DNA Using YEE(Gal-NAcAH)$_3$, a Synthetic Glyopeptide Ligand for the Asialoglycoprotein Receptor" *Bioconjugate Chemistry* 5 (6):612–620 (1994).

Richter and Zuckermann, "Synthesis of Peptide Nucleic Acids (PNA) by Submonomer Solid–Phase Synthesis" 5(11):1159–1162 (1995).

Ledley (Human Gene Ther. (1995) 6:1129–1144).*

Wheeler et al. (Biochim. et Biophsica Acta 1280, 1996, 1–11).*

Mastrangelo et al. (Seminars in Oncology, vol. 23, 1:4–21, 1996).*

Ngo et al., in: *The Protein Folding Problem and Tertiary Structure Prediction,* 1994, Merz et al., (ed.), Birkhauser, Boston, MA, pp. 433 and 492–495.*

* cited by examiner

Two Step Monomer Assembly

Step 1: Acylation

Leaving   Carbonyl
Group     Group

Step 2: Nucleophilic Displacement

Three Step Monomer Assembly

Step 1: Acylation

Step 2: Nucleophilic Displacement

Step 3: Acylation

POLYCATIONIC POLYMERS

CROSS-REFERENCE TO RELATED APPLICATION

This application claims the benefit, under 35 U.S.C. §119(e) of U.S. provisional patent application No. 60/023,867, filed Aug. 13, 1996, which is incorporated herein by reference.

DESCRIPTION

1. Field of the Invention

This invention relates to compositions and methods for increasing the uptake of polynucleotides into cells. Specifically, the invention relates to vectors, targeting ligands, and polycationic agents. The polycationic agents are capable of (1) increasing the frequency of uptake of polynucleotides into a cell, (2) condensing polynucleotides; and (3) inhibiting serum and/or nuclease degradation of polynucleotides.

2. Background of the Invention

Polycations, such as polylysine, have been used to facilitate delivery of nucleic acids to cell interior. Both in vitro and in vivo applications have taken advantage of this property. See, for example, Gao et al., 1996, *Biochem.* 35:1027–1036.

Polynucleotides, typically DNA, may be taken into a cell by a receptor-mediated endocytosis pathway, a cellular mechanism which internalizes specific macromolecules. In general, complexes designed to be delivered in this fashion contain nucleic acids encoding the gene of interest and a polycationic agent, which acts as a DNA-binding carrier and both neutralizes the charge on the nucleic acids and condenses it.

Condensation facilitates entry of nucleic acids into cell vesicle systems by simulating a macromolecular structure. For example, polylysine condenses DNA into a toroid or doughnut-like structure. (Wagner et al., 1991, *Proc. Natl. Acad. Sci.* 88:4255–4259).

Polycations previously utilized for nucleic acid delivery to cell interiors include polylysine, protamines, histones, spermine, spermidine, polyornithine, polyargnine, and putrescine.

All publications mentioned herein are incorporated herein by reference for the purpose of disclosing and describing features of the invention for which the publications are cited in connection with.

SUMMARY OF THE INVENTION

An embodiment of the invention is a vector for expression of polypeptides. The vector of the instant invention comprises: (i) an Epstein Barr Virus (EBV) origin of replication; (ii) a polynucleotide encoding an EBV origin binding protein; (iii) an enhancer; (iv) a promoter; and (v) a terminator. Polynucleotides encoding a desired polypeptide, such as erythropoietin or leptin can be inserted into the vector. Also, ribozyme and antisense polynucleotides can also be inserted into the vector.

One embodiment of the invention is a composition capable of targeting a polynucleotide to a specific cell type. The composition comprises: (i) a lipoprotein; (ii) a polynucleotide binding molecule; and (iii) a polynucleotide.

Another embodiment of the invention is a method of increasing the frequency of uptake of polynucleotides into a cell by contacting a cell with a composition comprising: (i) a lipoprotein, (ii) a polynucleotide binding molecule; and (iii) a polynucleotide.

Yet another embodiment of the invention is a method of increasing the frequency of uptake of polynucleotides into a specific cell type by contacting a population of cells with a composition comprising (i) a lipoprotein, (ii) a polynucleotide binding molecule; and (iii) a polynucleotide.

One embodiment of the invention is a polycationic agent exhibiting a net positive electrical charge at physiological pH with the following formula:

$$Ta \left[ \begin{array}{c} R_1 \ R_2 \ O \\ | \ | \ \| \\ N-C-C \\ \vdots \\ R_3 \end{array} \right]_n Tc$$

where Ta and Tc are terminating groups. A preferred subset of these compounds is the set where $R_2$ is hydrogen. Even more preferred are polymers comprising at least one unnatural amino acid. Also preferred are polymers where $R_2$ and $R_3$ are hydrogen and $R_1$ is not hydrogen, also referred to as poly N-substituted glycines or "poly NSGs."

Another embodiment is a neutral polymer exhibiting no net positive or negative electrical charge at physiological pH with the following formula:

$$Ta \left[ \begin{array}{c} R_1 \ R_2 \ O \\ | \ | \ \| \\ N-C-C \\ \vdots \\ R_3 \end{array} \right]_n Tc$$

where Ta and Tc are terminating groups. A preferred subset of these compounds is the set where $R_2$ is hydrogen. Even more preferred are polymers comprising at least one unnatural amino acid. Also preferred are polymers where $R_2$ and $R_3$ are hydrogen and $R_1$ is not hydrogen, also referred to as poly N-substituted glycines or "poly NSGs."

The instant polycationic agents and neutral polymers are capable of neutralizing the electrical charge of nucleic acids. A subset of these compounds are capable of (1) condensing the structure of polynucleotides and/or (2) protecting polynucleotides from serum and/or nuclease degradation.

Yet another embodiment of the invention are polycationic agents and neutral polymers that (1) target binding of nucleic acids to cell surfaces, (2) trigger cell membrane destabilization; (3) exhibit endosome buffering capacity; (4) trigger endocytosis; (5) help trigger the release of polynucleotide/lipid complexes from endosomes or (6) nuclear tropism.

Another embodiment of the invention is a composition comprising a polynucleotide of interest and an effective amount of the polycationic agent to neutralize the charge of the polynucleotide. Optionally, the composition includes a ligand which directs the complex to particular cells expressing a ligand-binding partner, and/or an endosomolytic agent, which serves to cause disruption of the endosome containing the complex.

Another embodiment of the invention is a method of condensing nucleic acids by providing an effective amount of the polycationic agents or neutral polymers of the invention and contacting the agent with the desired polynucleotides.

Also an embodiment of the invention is a method of inhibiting serum and/or nuclease degradation of nucleic acids by providing an effective amount of the the polycationic agents or neutral polymers of the inventions and contacting the agent with the desired nucleic acids.

DETAILED DESCRIPTION

Definitions

Figure 1:
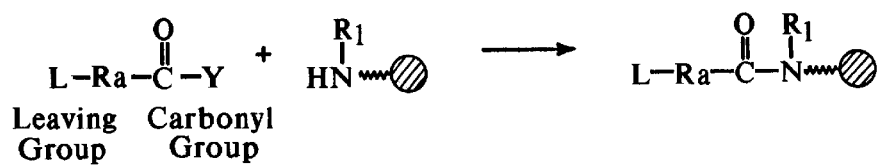
FIG. 1 is a schematic of a two-step monomer assembly reaction scheme.
Figure 1:

"Lipoproteins" refers to polypeptides that are associated non-covalently with lipids in the bloodstream and are capable of binding to cellular receptors. Preferably, lipoproteins are those involved with transport and storage of lipids. Such proteins include, for example, chylomicrons, low density lipoprotein (LDL), very low density lipoprotein (VLDL), intermediate density lipoprotein (IDL), and high density lipoprotein (HDL). Also, included in the term are mutants, fragments, or fusions of the naturally occurring lipoproteins. Also, modifications of naturally occurring lipoproteins can be used, such as acetylated LDL.

Mutants, fragments, fusions, or modifications of the naturally occurring lipoproteins are amino acid sequences that exhibit substantial sequence identity to naturally occurring lipoproteins or a fragment thereof. These polypeptides will retain more than about 80% amino acid identity; more typically, more than about 85%; even more typically, at least 90%. Preferably, these polypeptides will exhibit more than about 92% amino acid sequence identity with naturally occurring lipoproteins or fragment thereof; more preferably, more than about 94%; even more preferably, more than about 96%; even more preferably, more than about 98%; even more preferably, more than about 99%. All of these polypeptides exhibit receptor binding properties of naturally occurring lipoproteins. Usually, such polypeptides exhibit at least about 20% receptor binding of naturally occurring lipoproteins. More typically, the polypeptides exhibit at least about 40%, even more typically the polypeptides exhibit at least about 60%; even more typically, at least about 70%; even more typically, at least about 80%; even more typically, at least about 85%; even more typically, at least about 90%; even more typically, at least about 95% receptor binding of the naturally occurring lipoproteins.

"Polynucleotide binding molecule" refers to those compounds that associate with polynucleotides, and the association is not sequence specific. For example, such molecules can (1) aid in neutralizing the electrical charge of polynucleotide, or (2) facilitate condensation of nucleotides, or (3) inhibit serum or nuclease degradation.

"Polycationic agent" refers generally to a polymer comprising positively-charged single units, although some non-positively charged units may be present in the polymer. The instant agents exhibit a net positive charge under physiologically relevant pH. Such agents are capable of neutralizing the charge of nucleic acids and can exhibit additional properties, such as condensation and/or serum protection of nucleic acids. Preferably, the agents comprises both amino acids and NSGs as monomeric units; also, preferred are agents comprising NSGs as monomeric units.

"Physiologically relevant pH" varies somewhat between in vitro and in vivo applications. Typically, the physiological pH is at least 5.5; more typically, at least 6.0; even more typically, at least 6.5. Usually, physiologically relevant pH is no more than 8.5; more usually, no more than 8.0; even more usually, no more than 7.5.

"Polynucleotide" or "nucleic acid" refers to DNA, RNA, analogues thereof, peptide-nucleic acids, and DNA or RNA with non-phosphate containing nucleotides. Additionally, these nucleic acids may be single-stranded, double-stranded, or chimeric single- or double-stranded molecules.

The term "oligomer" includes polymers such as poly NSGs, produced by the submonomer process described herein and also in Zuckermann et al. supra. includes polymers, copolymers, and interpolymers of any length. More specifically, oligomers may comprise a single repeating monomer, two alternating monomer units, two or more monomer units randomly and/or deliberately spaced relative to each other. Regardless of the type of polyamide produced, the polyamide of the invention may be produced by the same general procedure which includes repeating a two-step or three step cycle wherein a new monomer unit is added in each cycle until an oligomer of desired length is obtained. The oligomer is preferably 2–100 monomers, more preferably 2–50, or 18–28 monomers or 24 to 48 monomers in length.

The term "frequency of uptake of polynucleotides into a cell" refers to an increase in the amount of polynucleotides actually taken up by a cell relative to the amount actually administered to the cell. The frequency of uptake of polynucleotides into a cell is increased if it is greater than the frequency of uptake of naked polynucleotides. For example, using in vitro transfection methods, uptake of naked polynucleotides into mammalian cells is not usually detectable over background. Some frequency of uptake, however, can be detected when naked polynucleotides are delivered in vivo. The frequency of uptake in vivo and in vitro depends on the tissue type. The frequency of uptake can be measured by known methods for detecting the presence of polynucleotides, such as Northern, Southern, or Polymerase Chain Reaction (PCR) techniques.

Usually, a composition or compound is capable of increasing the frequency of polynucleotide uptake into a cell if it induces a frequency of uptake that is at least 10% greater than the frequency of naked polynucleotide uptake; more usually, at least 15% greater; even more usually, 20% greater; even more usually, at least 30%; and up to 40% to 100% greater, and even 1,000% and 10,000% greater.

"Naked polynucleotides" refers to polynucleotides that are substantially free from any delivery vehicle that can act to facilitate entry into the cell. For example, polynucleotides are naked when free from any material which promotes transfection, such as liposomal formulations, charged lipids, such as Lipofectin® or precipitating agents such as $Ca_3(PO_4)_2$.

"Effective amount to increase the frequency of polynucleotide uptake into cells" refers to an amount that induces a frequency of polynucleotide uptake into a cell that is at least 10% greater than the frequency of naked polynucleotide uptake; more usually, at least 15% greater; even more usually, 20% greater; even more usually, at least 30%; even more usually, at least 40%.

"Effective amount to neutralize nucleic acids" refers to the amount used to neutralize at least 10% of the electrical charge of the nucleic acid composition; more preferably; the amount refers to the amount used to neutralize at least 40%; even more preferably, the amount to neutralize 50% of the electrical charge; even more preferably, the amount to neutralize 60% of the electrical charge; even more preferably, the amount to neutralize 70% of the electrical charge; even more preferably, the amount to neutralize 80% of the electrical charge; and most preferably, at least 90% of the electrical charge of the nucleic acid composition of interest.

"Condensation of nucleic acids" occurs when the polycationic agent that is combined with nucleic acids, neutralizes the electrical charge of the nucleic acids and causes it to assume a reduced structure relative to uncomplexed nucleic acids. Preferably, condensation reduces the structure of nucleic acids to a size that can be internalized by structures present on cell surface membranes. Condensation can be measured by determining the charge of the nucleic acid/polycationic agent by gel electrophoresis, for example. Alternatively, an effective amount to condense nucleic acids can also be measured by the final size of the polycationic agent/nucleic acid complex.

"Effective amount to inhibit serum or nuclease degradation of nucleic acids" refers to the amount used to increase the half-life of the polynucleotide when exposed to serum and/or nucleases by at least 5 minutes as compared the uncomplexed nucleic acids; more preferably, the amount used to inhibit degradation by at least 10 minutes; even more preferably, the amount used to inhibit degradation by at least 30 minutes; even more preferably, the amount used to inhibit degradation by at least 45 minutes; even more preferably, the amount used to inhibit degradation by at least 60 minutes; even more preferably, the amount used to inhibit degradation by at least 90 minutes; and more preferably, the amount used to inhibit degradation by at least 120 minutes.

A composition containing A is "substantially free of" B when at least 85% by weight of the total A+B in the composition is A. Preferably, A comprises at least about 90% by weight of the total of A+B in the composition, more preferably at least about 95% or even 99% by weight.

"Immunogenicity" refers to the ability of a given molecule or a determinant thereof to induce the generation of antibodies with binding capacity to the molecule upon administration in vivo, to induce a cytotoxic response, activate the complement system, induce allergic reactions, and the like. An immune response may be measured by assays that determine the level of specific antibodies in serum, by assays that determine the presence of a serum component that inactivates the polycationic agent/nucleic acid complex or conjugated gene delivery vehicle, or by other assays that measure a specific component or activity of the immune system. As discussed in more detail below, low immunogencity may be established by these assays. The terms "low immunogenicity," "reduced immunogenicity," "lowered immunogenicity" and similar terms are intended to be equivalent terms.

An "origin of replication" is a polynucleotide sequence that initiates and regulates replication of polynucleotides, such as an expression vector. The origin of replication behaves as an autonomous unit of polynucleotide replication within a cell, capable of replication under its own control. With certain origins of replication, an expression vector can be reproduced at a high copy number in the presence of the appropriate proteins within the cell. Examples of origins are the $2\mu$ and autonomously replicating sequences, which are effective in yeast; and the viral T-antigen, effective in COS-7 cells.

GENERAL METHODS AND DETAILED DESCRIPTION

Polynucleotides

Polynucleotides used in the instant invention can be used to express desired polypeptides, or can be, in themselves, therapeutic, such as ribozymes or antisense polynucleotides. Such polynucleotides can be used in in vitro, ex vivo, and in vivo applications.

Also, the polynucleotides of the invention can be vectors that express polypeptides, ribozymes, or antisense molecules. Vectors contain at least a promoter to initiate transcription operably linked to the coding region, ribozyme or antisense molecule. Other components that can be included in the vector are, for example: (1) a terminator sequence; (2) a sequence encoding a leader peptide to direct secretion; (3) a selectable marker; and (4) an origin of replication. An orgin of replication is not necessary. The polynucleotides to be delivered can be either replicating or non-replicating. Other components can be added as desired and convenient.

The polynucleotides and methods of the invention can be utilized with any type of host cell. The choice of promoter, terminator, and other optional elements of an expression vector will depend on the host cell chosen. The invention is not dependent on the host cell selected. Convenience and the desired level of protein expression will dictate the optimal host cell. A variety of hosts for expression are known in the art and available from the American Type Culture Collection (ATCC) (Rockville, Md., U.S.A.). Suitable bacterial hosts suitable include, without limitation: Campylobacter, Bacillus, Escherichia, Lactobacillus, Pseudomonas, Staphylococcus, and Streptococcus. Yeast hosts from the following genera may be utilized: Candida, Hansenula, Kluyveromyces, Pichia, Saccharomyces, Schizosaccharomyces, and Yarrowia. *Aedes aegypti, Bombyx mori, Drosophila melanogaster,* and *Spodoptera fru-*

*giperda* (PCT Patent Publication No. WO 89/046699; Carbonell et al., 1985, *J. Virol.* 56:153; Wright, 1986, *Nature* 321:718; Smith et al. 1983, *Mol. Cell. Biol.* 3:2156; and see generally, Fraser et al., 1989, *In Vitro Cell. Dev. Biol.* 25:225).

Useful mammalian cell types for in vitro applications include for example, those cell lines available from the American Type Culture Collection (ATCC), Chinese hamster ovary (CHO) cells, HeLa cells, baby hamster kidney (BHK) cells, monkey kidney cells (COS), human hepatocellular carcinoma cells (e.g., Hep G2), human embryonic kidney cells, baby hamster kidney cells, mouse sertoli cells, canine kidney cells, buffalo rat liver cells, human lung cells, human liver cells, mouse mammary tumor cells, as well as others.

Useful cell types for in vivo or ex vivo applications include, without limitation, any tissue type, such as muscle, skin, brain, lung, liter, spleen, blood, bone marrow, thymus, heart, lymph, bone, cartilage, pancreas, kidney, gall bladder, stomach, intestine, testis, ovary, uterus, rectum, nervous system, eye, gland, and connective tissue.

A. In vitro and Ex vivo Vectors

The polynucleotides encoding the desired polypeptides or ribozymes, or antisense polynucleotides can be transcribed and/or translated using the following promoters and enhancers as examples. The examples include, without limitation: the 422(aP2) gene and the stearoyl-CoA desaturase 1 (SCD1) gene, which contains suitable adipocyte-specific promoters, as described in Christy et al., 1989, *Genes Dev.* 3:1323–1335. Synthetic non-natural promoters or hybrid promoters can also be used herein. For example, a T7T7/T7 promoter can be constructed and used, in accordance with Chen et al., 1994, *Nucleic Acids Res.* 22:2114–2120, where the T7 polymerase is under the regulatory control of its own promoter and drives the transcription of a polynucleotide sequence, which is placed under the control of another T7 promoter. The primary determinant for the fat-specific expression is an enhancer located at about >5 kb upstream of the transcriptional start site, as described in Ross et al., 1990, *Proc. Natl. Acad. Sci. USA*.87:9590–9594 and Graves et al., 1991, *Genes Dev.* 5:428–437. Also suitable for use herein is the gene for the CCAAT/enhancer-binding protein C/EBPα, which is highly expressed when 3T3-L1 adioblast commit to the differentiation pathway and in mature post-mitotic adipocytes, as described in Birkenmeier et al., 1989, *Gene Dev.* 3:1146–1156. The recently isolated transcription factor PPARγ2, expressed exclusively in adipocyte tissues, as described in Tontonoz et al., 1994, *Cell* 79:1147–1156, can also be used herein.

Typical promoters for mammalian cell expression include the SV40 early promoter, the CMV promoter, the mouse mammary tumor virus LTR promoter, the adenovirus major late promoter (Ad MLP), and the herpes simplex virus promoter, among others. Other non-viral promoters, such as a promoter derived from the murine metallothionein gene, will also find use in mammalian constructs. Expression may be either constitutive or regulated (inducible), depending on the promoter. Typically, transcription termination and polyadenylation sequences will also be present, located 3' to the translation stop codon. Preferably, a sequence for optimization of initiation of translation, located 5' to the coding sequence, is also present. Examples of transcription terminator/polyadenylation signals include those derived from SV40, as described in Sambrook et al., 1989, "Molecular Cloning, A Laboratory Manual," second edition, Cold Spring Harbor Press, Cold Spring Harbor, N.Y. Introns, containing splice donor and acceptor sites, may also be designed into the constructs of the present invention.

Enhancer elements can also be used herein to increase expression levels of the mammalian constructs. Examples include the SV40 early gene enhancer, as described in Dijkema et al., 1985, *EMBO J.* 4:761, and the enhancer/promoter derived from the long terminal repeat (LTR) of the Rous Sarcoma Virus, as described in Gorman et al., 1982b, *Proc. Natl. Acad. Sci. USA* 79:6777, and human cytomegalovirus, as described in Boshart et al., 1985, *Cell* 41:521. A leader sequence can also be present which includes a sequence encoding a signal peptide, to provide for the secretion of the foreign protein in mammalian cells. Preferably, there are processing sites encoded between the leader fragment and the gene of interest such that the leader sequence can be cleaved either in vivo or in vitro.

Other regulatory regions from viruses can be included in the polynucleotides of the instant invention to increase transcription and translation levels or increase the duration of transcription and translation. For example, the long terminal repeats of HIV can be included. Alternatively, the inverted terminal repeats of the Epstein Barr Virus can be used.

There exist expression vectors that provide for the transient expression in mammalian cells of DNA encoding the target polypeptide. In general, transient expression involves the use of an expression vector that is able to replicate efficiently in a host cell, such that the host cell accumulates many copies of the expression vector and, in turn, synthesizes high levels of a desired polypeptide encoded by the expression vector. Transient expression systems, comprising a suitable expression vector and a host cell, allow for the convenient positive identification of polypeptides encoded by cloned DNAs, as well as for the rapid screening of such polypeptides for desired biological or physiological properties. Thus, transient expression systems are particularly useful for purposes of identifying analogs and variants of the target polypeptide that have target polypeptide-like activity.

B. In vivo Vectors

For delivery using viral vectors, any of a number of viral vectors can be used, as described in Jolly, 1994, *Cancer Gene Therapy* 1:1–64. For example, the coding sequence of a desired polypeptide or ribozymes or antisense molecules can be inserted into plasmids designed for transcription and/or translation in retroviral vectors, as described in Kimura et al., 1994, *Human Gene Therapy* 5:845–852, adenoviral vectors, as described in Connelly et al., 1995, *Human Gene Therapy* 6:185–193, adeno-associated viral vectors, as described in Kaplitt et al., 1994, *Nature Genetics* 6:148–153 and sindbis vectors. Promoters that are suitable for use with these vectors include the Moloney retroviral LTR, CMV promoter and the mouse albumin promoter. Replication competent free virus can be produced and injected directly into the animal or humans or by transduction of an autologous cell ex vivo, followed by injection in vivo as described in Zatloukal et al. 1994, *Proc. Natl. Acad. Sci. USA* 91:5148–5152.

The polynucleotide encoding a desired polypeptide or ribozyme or antisense polynucleotide can also be inserted into plasmid for expression of the desired polypeptide in vivo. For in vivo therapy, the coding sequence can be delivered by direct injection into tissue, or via oral administration as an aerosol. Promoters suitable for use in this manner include endogenous and heterologous promoters such as CMV. Further, a synthetic T7T7/T7 promoter can be constructed in accordance with Chen et al., 1994, *Nucleic Acids Res.* 22:2114–2120, where the T7 polymerase is under the regulatory control of its own promoter and drives the transcription of polynucleotide sequence, which is also placed under the control of a T7 promoter. The polynucleotide can be injected in a formulation that can stablize the coding sequence and facilitate transduction thereof into cells and/or provide targeting, as described in Zhu et al., 1993, *Science* 261:209–211.

Expression of the coding sequence of a desired polypeptide or replication of a ribozyme or antisense polynucleotide in vivo upon delivery for gene therapy purposes by either viral or non-viral vectors can be regulated for maximal efficacy and safety by use of regulated gene expression promoters as described in Gossen et al., 1992, *Proc. Natl. Acad. Sci. USA* 89:5547–5551. For example, the polynucleotide transcription and/or translation can be regulated by tetracycline responsive promoters. These promoters can be regulated in a positive or negative fashion by treatment with the regulator molecule.

For non-viral delivery of the coding sequence of the desired polypeptide, the sequence can be inserted into conventional vectors that contain conventional control sequences for high level expression.

C. Preferred Vector

A preferred vector comprises: (1) an (EBV) origin of replication or a BKV (BK virus), a parvovirus, origin of replication; (2) a coding region for an EBV or BKV origin binding protein; (3) at least one inverted terminal repeat; (4) a promoter; (5) an enhancer; (6) a terminator; (7) optionally, a selectable marker.

Preferably, the orgin of replication is EBV ori p; more preferably, nucleotides 2623 to 4559 of SEQ ID NO:1 are utilized. The sequence is obtainable from vector pCEP4, commercially available from Invitrogen, San Diego, Calif., USA.

Preferably, the coding region encodes the EBV nuclear antigen A, which binds to EBV ori p; more preferably, the polynucleotide sequence is nucleotides 14 to 2594 of SEQ ID NO:1 are utilized. The sequence is obtainable from vector pCEP4, commercially available from Invitrogen, San Diego, Calif., USA.

Fragments and mutants of the preferred origin and binding protein capable of initiating replication of the vector in the desired host cell can be utilized. Preferably, the fragments and mutants will retain more than about 80% sequence identity with nucleotides 14 to 2594 or 2623 to 4559 of SEQ ID NO:1 or fragment thereof; more typically, more than about 85%; even more typically, at least 90%. Preferably, these polynucleotides exhibit more than about 92% sequence identity with nucleotides 14 to 2594 or 2623 to 4559 of SEQ ID NO:1 or fragment thereof; more preferably, more than about 94%; even more preferably, more than about 96%; even more preferably, more than about 98%; even more preferably, more than about 99%.

Preferably, the inverted terminal repeats are those sequences found in adenovirus (AV) or adeno-associated virus (AAV); more preferably, the inverted terminal repeats are those found in AAV; even more preferably, the polynucleotide sequence is 4938 to 5104 or 7189 to 7355 of SEQ ID NO:1. The sequence of AAV is described in Samulski et al., 1987, *J. Virol.* 61:3096–3101.

Fragments and mutants of the preferred inverted terminal repeat capable of initiating replication of the vector in the desired host cell can be utilized. Preferably, the fragments and mutants will retain more than about 80% sequence identity with nucleotides 4938 to 5104 or 7189 to 7355 of SEQ ID NO:1 or fragment thereof; more typically, more than about 85%; even more typically, at least 90%. Preferably, these polynucleotides exhibit more than about 92% sequence identity with nucleotides 4938 to 5104 or 7189 to 7355 of SEQ ID NO: 1 or fragment thereof; more preferably, more than about 94%; even more preferably, more than about 96%; even more preferably, more than about 98%; even more preferably, more than about 99%.

Preferably, the cytomegalovirus enhancer/promoter is utilized; more preferably, the CMV promoter sequence is nucleotide sequence 5112 to 6734 of SEQ ID NO:1.

Mutants and fragments of the preferred enhancer and promoter capable of initiating transcription and/or translation can be utilized. Preferably, the fragments and mutants will retain more than about 80% sequence identity with nucleotides 5112 to 6734 of SEQ ID NO:1 or fragment thereof; more typically, more than about 85%; even more typically, at least 90%. Preferably, these polynucleotides exhibit more than about 92% sequence identity with nucleotides 5112 to 6734 of SEQ ID NO:1 or fragment thereof; more preferably, more than about 94%; even more preferably, more than about 96%; even more preferably, more than about 98%; even more preferably, more than about 99%.

A preferred terminator is the bovine growth hormone poly A sequence; more preferably, the polynucleotide sequence is nucleotide 6818 to 7050 of SEQ ID NO:1.

Mutants and fragments of the preferred terminator capable of terminating transcription and/or translation can be utilized. Preferably, the fragments and mutants will retain more than about 80% sequence identity with nucleotides 6818 to 7050 of SEQ ID NO:1 or fragment thereof; more typically, more than about 85%; even more typically, at least 90%. Preferably, these polynucleotides exhibit more than about 92% sequence identity with nucleotides 6818 to 7050 of SEQ ID NO:1 or fragment thereof; more preferably, more than about 94%; even more preferably, more than about 96%; even more preferably, more than about 98%; even more preferably, more than about 99%.

The sequence of the preferred vector is shown in SEQ ID NO:1. Polynucleotides encoding polypeptides, such as erythropoietin or leptin, and ribozymes and antisense polynucleotides can be inserted into the vector.

D. Examples of Coding Regions, Ribozymes, and Antisense Molecules

The following are examples of coding regions, ribozymes, and antisense molecules that can be used to treat various indications in mammals. The nucleotide sequence of the genes of interest can be found, for example, in publically available databases, such as Genbank. Polynucleotides to be delivered can be used to treat viral infections or chronic pathogen infection.

1. Hemophilia

Gene replacement by in vivo delivery of polynucleotides can be effective in treating hemophilia The following are examples of polypeptides that can be encoded by the polynucleotides to be delivered: Factor VIII:C, mutants of Factor VIII:C, preferably those that are uncleavable. Also, useful to treat hemophilia are ribozyme and antisense polynucleotides as inhibitors of Tissue Factor Plasminogen Inhibitor (TFPI).

The routes of delivery for treating hemophilia include, for example, intravenous/intrahepatic injection, ex vivo transduction of stem cells or lymphocytes using retroviral vectors.

2. Treatment of Graft Versus Host Disease

In vivo delivery of polynucleotides encoding prodrugs can be used for direct ablation to treat graft versus host disease in, for example, leukemia bone marrow transplantation. Herpes thymidine kinase in conjunction with ganciclovir can be utilized for this purpose. Other examples of prodrugs are described in the cancer section.

The routes of delivery for treating graft versus host disease include, for example, ex vivo transduction of T-lymphocytes using retroviral vectors.

3. Vaccines

In vivo delivery of polynucleotides encoding a desired antigen can be utilized to induce an immune response. This response can include both cellular and humoral response. This type of vaccine can be used to treat cancer as well as infectious diseases. Further, such treatment can be either prophylactic or therapeutic immunotherapy.

Examples of infectious diseases include, Human Immunodeficiency Virus (HIV), Hepatitis A, B, C, etc., (HAV, HBV, HCV, etc.), Human Papiloma Virus (HPV), cytomegalovirus (CMV), herpes simplex 1 and 2 (HSV), etc. Preferred antigens include non-structural proteins 3, 4a, and 5b (NS3, NS4, and NS5b) of HCV; gB2 and gD2 of HSV; env and rev proteins of HIV.

Also, cancer antigens can be used in vaccines, for both therapeutic and prophylactic purposes.

The antigens can be presented in the context of Class I major histocompatibility antigens, or to induce a cellular cytotoxic T cell response, or to induce a humoral response comprising the synthesis of antibodies.

In addition, an antisense or ribozyme target to a immune suppressive molecule, IL-10, TGF-β, and CTLA-4, for example, can be useful to be administered with a vaccine.

The routes of delivery for vaccines include, for example, intramuscular injection, dendritic cell-based immunization, or oral immunization by both viral and non-viral vectors.

4. Diabetes Mellitus

Diabetes is another indication that can be treated by in vivo delivery of a replacement gene. The following are examples of useful polypeptides to be encoded by the replacement gene: insulin, insulin-like growth factor I and II (IGF-I and II).

Also useful for treating diabetes are polynucleotides encoding IAS-L, found on the surface of B cells in the pancreas, to protect the cells from immune destruction.

The routes of delivery for treating diabetes include, for example, liver-directed, parotid-directed, pancreas-directed, salivary gland-directed using both viral and non-viral vectors.

5. Hyperlipidemia

Hyperlipidemia can be treated by in vivo delivery of the following polynucleotides encoding apoproteins or lipoprotein receptors. A more extensive description of lipoproteins and apoproteins is provided below.

The routes of delivery for treating hyperlipidemia include, for example, liver-directed intravenous administration by both viral and non-viral vectors.

6. Myocardial Ischemia or Infarction

The following are examples of polynucleotides that are useful, when delivered in vivo, to treat myocardial ischemia or infarction:

polynucleotides encoding basic fibroblast growth factor (bFGF), fibroblast growth factor 5 (FGF-5) and IGF-I.

The routes of delivery for treating myocardial ischemia or infarction include, for example, intrapericardial delivery of viral vector or non-viral vectors.

7. Bowel Disease

The following are examples of polynucleotides that can be delivered in vivo to treat bowel disease:

(i) ribozymes or antisense polynucleotides as inhibitors of macrophage/inflammatory cell recruitment or activation, such as NFκB;

(ii) ribozymes or antisense polynucleotides to act as anti-apoptotic agents, such as inhibitors of interleukin 1b converting enzyme family;

(iii) polynucleotides encoding complement blockers, such as decay accelarting factor (DAF), membrane cofactor protein (MCP); and the fusions of DAF and MCP also known as CAB-2;

(iv) cyclooxygenase inhibitors;

(v) anti-proliferative agents, such as, ribozymes, antisense oligonucleotides, antibodies, protein, or peptides against c-myb, ras/raf, PI3 kinase, cyclins;

(vi) polynucleotides encoding suicide proteins/genes, such as, herpes thymidine kinase;

(vii) polynucleotides encoding replacement genes or proteins which maybe deficient or down regulated during the devleopment of inflammatory bowel disease.

(viii) polynucleotides encoding IκB.

8. Prostate Cancer and Benign Prostatic Hyperplasia

The following polynucleotides can be delivered to treat prostate cancer and benign prostatic hyperplasia:

(i) a polynucleotide encoding a pro-apoptotic agent, including for example, fas, fas ligand, fadd, fap-1, tradd, faf, rip, reaper, apoptin, interleukin-2 converting enzyme;

(ii) a polynucleotide encoding an anti-angiogenic agent, including, for example, bFGF soluble receptor and fragments, angiostatin, transforming growth factor-β (TGF-β), interferon-α (IFNα), proliferin-related protein, a urokinase plasminogen activator receptor antagonist, platelet factor 4 (PF4), thrombospondin, a tissue inhibitor of metalloproteinase, and prolactin;

(iii) a polynucleotide encoding a immunomodulating agent including, for example, interleukin-2 (IL-2), IFNα, IFNβ, IFNγ, granulocyte macrophage-colony stimulating factor (GM-CSF), and macrophage-colony stimulating factor (M-CSF);

(iv) a ribozyme or antisense polynucleotide as an anti-proliferative agent including, for example, an inhibitor of a signal transduction pathway, for example, an inhibitor of a signal transduction pathway mediated by myb, ras, ras superfamily, raf, phosphoinositol (PI3-kinase), a phosphotyrosine binding (PT13) domain, a SRC homology-2 (SH2) domain, a SRC homology-3 (SH3) domain, a plextrin homology (PH) domain, JUN kinase, and a stress activated kinase, signaling inositol phosphatases; and an inhibitor of a cyclin;

(v) a ribozyme or antisense polynucleotide as an inhibitor of a growth factor or inhibitor of a receptor of a growth factor, including, for example, epidermal growth factor (EGF), TGF-α, FGF, TGF-β, platelet derived growth factor (PDGF), keratinocyte growth factor (KGF), or any prostate cell specific growth factor, (vi) a polynucleotide encoding a tumor suppressor gene or a gene down-regulated during the onset of a hyperplastic condition in the prostate; and (vii) an antisense or ribozyme target to a immune suppressive molecule, IL-10, TGF-β, and CTLA-4, for example.

9. Anemia, Leukopenia, and Thrombocytopenia

Anemia can be treated by in vivo delivery of a polynucleotide encoding erythropoietin, GM-CSF-, G-CSF, M-CSF, and thrmobopoietin, for example. Examples of delivery routes for this indication include without limitation: liver-targeted intravenous administration of viral vectors and non-viral vectors. See the Examples below.

10. Cardiomyopathy

The following are examples of polynucleotides that can be delivered in vivo to treat cardiomyopathy: polynucleotides encoding, IGF-1, L-amino acid decarboxylas, inhibitors of β adrenergic receptor kinases (BARK), troponin, and β adrenergic receptors.

Examples of delivery routes for this indication include, without limitation, pericardial expression of IGF-1, and for the other genes, intramycardial injection or myocardial trageting via intracoronary injection or intrapericardial administration of viral vectors or non-viral vectors.

11. Rheumatoid Arthritis

The following are examples of polynucleotides that can be delivered in vivo to treat rheumatoid arthritis, polynucleotides encoding a prodrug, such as herpes thymidine kinase, MMP inhibitors, fas, and pro-apoptotic proteins, described above, and interleukin-1 receptor A, interleukin-10, IκB.

Also, antisense and ribozyme polynucleotides as inhibitors of NFκB.

Examples of delivery routes for this indication include, without limitation, intraarticular injection of viral and non-viral vectors.

12. Osteoarthritis and Psoriasis

The following are examples of polynucleotides that can be delivered in vivo to treat osteoarthritis and psoriasis: polynucleotides encoding IGF-1; ribozyme and antisense polynucleotides as inhibitors of metalloproteinase inhibitors.

Also, the following are examples of polynucleotides that can be delivered in vivo to treat osteoarthritis and psoriasis, polynucleotides encoding a prodrug, such as herpes thymidine kinase, MMP inhibitors, fas, and pro-apoptotic proteins, described above, and interleukin-1 receptor A, interleukin-10, IκB.

Also, antisense and ribozyme polynucleotides as inhibitors of NFκB.

Examples of delivery routes for this indication include, without limitation, intraarticular injection.

13. Restenosis

The following are examples of polynucleotides that can be delivered in vivo to treat restenosis:

(i) polynucleotides encoding a prodrug, such as thymidine kinase, other examples are described in the cancer section;

(ii) polynucleotides encoding tissue factor plasminogen inhibitor (TFPI);

(iii) polynucleotides encoding c-myb rbz, c-ras rbz, (iv) polynucleotides encoding pro-apoptotic agents, described above;

(v) polynucleotides encoding IκB.

Examples of delivery routes for this indication include, without limitation, intracoronary delivery of viral and non-viral vectors.

14. Cancer

The gene delivery vectors of the invention are useful in delivering therapeutic genes for treatment of hyperproliferative disorders, including malignancy, for treatment of infectious disease and for treatment of inflammatory diseases, including autoimmune disease. For instance, the gene therapy vectors can be used to express cytokines or proteins that convert an inactive or partially active prodrug into an active drug. In many cases, conversion of the prodrug into its active form results in a compound with cytolytic activity.

a. Prodrug converting enzymes

A number of "suicide genes" which encode different proteins useful in prodrug conversion can be used in the instant invention. For instance, nucleoside kinases such as thymidine kinase are particularly useful. In particular, the HSV-TK system has important advantages for anti-tumor cell therapy. See PCT publication number WO 91/02805 entitled "Recombinant Retroviruses Delivering Vector Constructs to Target Cells" and PCT publication number WO 95/14014091 entitled "Compositions and Methods for Utilizing Conditionally Lethal Genes" for a description of treatment of cancer and other diseases by gene delivery vectors expressing thymidine kinase and other prodrug converting enzymes. HSV-TK transduced tumor cells can mediate a significant bystander killing effect on untransduced neighboring cells in vitro and in vivo (Moolten et al., supra., Freeman et al. 1993, *Cancer Res.* 53:5274), most commonly as a result of transfer to the toxic ganciclovir metabolite, GCV triphosphate, between adjacent cells through intercellular gap junctions (Bi et al., 1993, *Human Gene Therap.* 4:725). Endothelial cells in capillary walls are connected by gap junctions, so a dramatic bystander effect created by GCV-triphosphate transfer between neighboring endothelial cells and the massive amplification effects of the clotting cascade and the tumor to endothelial cell ratio could ensue (Denekamp et al., 1986, *Cancer Topics* 6:6; Denekamp et al., 1984, *Prog. Appl. Microcir.* 4:28). Recent evidence suggests that the occasional transduction of tumor endothelial cells during intralesional therapy with HSV-TK retroviral vectors may account for a significant component of the antitumor activity of the vectors (Ram et al., 1994, *J. Neurosurg.* 81:256). In addition, the suicide gene is only conditionally cytotoxic to the target cells (i.e. only when GCV is given). Consequently, an ex vivo administration method can be be utilized. For example, in this type of protocol, endothelial cells may be isolated from tumor biopsies (Medzelewski et al., 1994, *Cancer Res.* 54:336), induced to proliferate with appropriate mitogens (Ferrara et al., supra) and transduced with TK in vitro. Transplanted EC become incorporated into the neovasculature in days to weeks after intratumoral injection (Lal et al., 1994, *Cancer Gene Therap.*1:322), so GCV treatment would follow a suitable 'lag phase' to allow the transduced EC to integrate functionally in to the tumor vasculature. The two-step enzyme-prodrug system offers greater flexibility of delicate clinical management, because cessation of GCV infusion in the event of (potentially very serious) complications arising from damage to normal EC, would block toxicity without the need to block transgene activity in situ.

A number of alternative 'suicide genes' in addition to thymidine kinase may also be useful for cancer gene therapy (Moolten et al., supra.). Introduction of the bacterial cytosine deaminase gene (Huber et al., 1993, *Cancer Res.* 53:4619) into tumor cells confers sensitivity to the antifungal agent 5-fluorocytosine (5-FC). Cytosine deaminase converts 5-FC to 5-fluorouracil (5-FU, Nishiyama et al., 1985, *Cancer Res.* 45:1753). Since 5-FU is commonly used chemotherapeutic drug for breast cancer, several groups have developed cytosine deaminase-based 'suicide gene' therapy models for this disease. Tumor specificity may be further increased by introducing the c-erbB2 promoter/enhancer elements 5' to the cytosine deaminase gene, so that the therapeutic transgene is preferentially transcribed in c-erbB2-overexpressing breast tumor cells (Harris et al., 1994, *Gene Therap.* 1:170). Alkaline phosphatase has been widely explored as prodrug-activating enzyme in the related field of antibody directed enzymne-prodrug therapy (ADEPT). This enzyme has the advantage that it can activate a wide range of phosphorylated derivatives of anticancer agents (e.g. mitomycin C, etoposide, etc.) that cannot cross cell membranes until the charged phosphate group is cleaved off, so a single enzyme could generate de novo a cocktail of chemotherapeutic agents within the tumor mass (Senter et al., 1993, *Bioconjugate Chem.* 4:3). Other suicide genes may encode a polypeptide or polypeptides (with a corresponding non-cytotoxic agent) such as Herpes Simpex virus thymidine kinase (ganciclovir or acyclovir), Varicella Zoster virus thymidine kinase (6 methoxypurine arabino nucleoside;

Huber et al., 1991, *Proc. Natl. Acad. Sci. USA* 88:8039), *E. coli* cytosine deaminase (fluorouracil; Mullen et al., 1992, *Proc. Natl. Acad. Sci. USA*. 89:33), *E. coli* xanthine-guanine phophoribosyl transferase (thioxanthine; Beshard et al., 1987, *Mol. Cell Biol.* 7:4139), *E. coli* or Leishmania purine nucleotide phosphorylase (various nontoxic purine deoxyadenosine, adenosine, deoxyguanosine, or guanosine derivatives (Koszalka and Krenitsky, 1979, *J. Biol Chem* 254:8185, 1979; Sorscher et al., 1994, *Gene Therapy* 1:233), cytochrome pla50 2B1 or cytochrome p450 reductase (e.g., 3amino-1,2,4 benzotriazine 1,4-dioxide (Walton et al., 1992, *Biochem. Pharmacol.* 44:251), cell surface alkaline phosphatase (e.g., etoposide monophosphate; Senter et al., 1988, *Proc. Natl. Acad. Sci. USA* 85:4842, 1988), nitroreductase (e.g., metronidazole or nitrofurantoin; Hof et al., 1988, *Immunitat und Infektion* 16:220), N-deoxyribosy transferase (1-deazapurine; Betbeder et al., 1989, *Nucleic Acids Res* 17:4217), pyruvate ferrodoxin oxidoreductase (metronidazol; Upcroft et al., 1990, *Int. J. Parasitolog,* 20:489), carboxypepidase G2 (aminoacylate nitrogen mustards; Antoniw et al., 1990, *Brit J. Cancer* 62:909), carboxypeptidase A (methotrexate alpha alanine; Haenseler et al., 1992, *Biochemistry* 31:891), •lactamase (cephalosporin derivatives; Meyer et al., 1993, *Cancer Res.* 53:3956; and Vradhula et al., 1993, *Bioconjugate Chemistry* 4:334), Actinomycin D synthetase complex (synthetic pentapeptide lactone precursors; Katz et al., 1990, *J. Antibiotics* 43:231), and •-glucuronidase (various glucuronide derivatives of toxic drugs such as doxorubicin; Bosslet et al., 1994, *Cancer Res.* 54:2151; Haeberlin et al., 1993, *Pharmaceutical Res.* 10:1553).

Any of a variety of other enzymes which convert inactive prodrugs into active drugs and known to those of skill in the art can also used in the gene delivery vehicles of the invention. For example, see PCT publication number WO 95/14014091 entitled "Compositions and Methods for Utilizing Conditionally Lethal Genes", and European Patent publication number EP90309430, entitled "Molecular Chimeras Useful for Cancer Therapy—Comprising Regulatory Sequences and heterologous enzyme, e.g. Varicella Zoster Virus Thymidine Kinase" for a description of additional prodrug/enzyme systems useful for gene therapy. As an additional example, see PCT Patent Publication No. WO 95/13095 entitled "New Prodrugs and Enzyme Targeting Molecule Conjugates—Useful in Antibody Direct Enzyme Prodrug Therapy of e.g. Viral Infections".

A variety of tumors may be targeted for treatment by the gene delivery vehicles of the invention. In general, solid tumors are preferred, although leukemias and lymphomas may also be treated if they have developed a solid mass, or if suitable tumor associated markers exist such that the tumor cells can be physically separated from nonpathogenic normal cells. Representative examples of suitable tumors include melanomas, colorectal carcinomas, lung carcinomas (including large cell, small cell, squamous and adenocarcinomas), renal cell carcinomas and breast adenocarcinomas. Gene delivery vehicles expressing thymidine kinase and other prodrug converting enzymes are also useful in the treatment of autoimmune diseases including rheumatoid arthritis, osteoarthritis and graft vs. host disease. See e.g. PCT Patent Publication No. WO 95/14091, entitled "Compositions and Methods for Utilizing Conditionally Lethal Genes," for a description of treatment of disease with gene therapy vectors expressing prodrug converting enzymes.

b. Cytokines

A variety of polynucleotides encoding cytokines and immune system modulators can be delivered by the gene delivery vehicles of the invention for treatment of a number of different disorders. Representative examples include cytokines, such as IL-1, IL-2 (Karupiah et al., 1990, *J. Immunology* 144:290–298; Weber et al., 1987, *J. Exp. Med.* 166:1716–1733; Gansbacher et al., 1990, *J. Exp. Med.* 172: 1217–1224; U.S. Pat. No. 4,738,927), IL-3, IL-4 (Tepper et al., 1989, *Cell* 57:503–512; Golumbek et al., 1991, *Science* 254:713–716, 1991; U.S. Pat. No. 5,017,691), IL-5, IL-6 (Brakenhof et al., 1987, *J. Immunol.* 139:4116–4121; WO 90/06370), IL-7 (U.S. Pat. No. 4,965,195), IL-8, IL-9, IL-10, IL-11, IL-12, IL-13 (*Cytokine Bulletin,* Summer 1994), IL-14 and IL-15, particularly IL-2, IL-4, IL-6, IL-12, and IL-13, alpha interferon (Finter et al., 1991, *Drugs* 42(5):749–765; U.S. Pat. No. 4,892,743; U.S. Pat. No. 4,966,843; WO 85/02862; Nagata et al., 1980, *Nature* 284:316–320; Familletti et al., 1981, *Methods in Enz.* 78:387–394; Twu et al., 1989, *Proc. Natl. Acad. Sci. USA* 86:2046–2050; Faktor et al., 1990, *Oncogene* 5:867–872), beta interferon (Seif et al., 1991, *J. Virol.* 65:664–671), gamma interferons (Radford et al., *The American Society of Hepatology* 2008–2015, 1991; Watanabe et al., *PNAS* 86:9456–9460, 1989; Gansbacher et al., 1990, *Cancer Research* 50:7820–7825; Maio et al., 1989, *Can. Immunol. Immunother.* 30:34–42; U.S. Pat. No. 4,762,791; U.S. Pat. No. 4,727,138), G-CSF (U.S. Pat. Nos. 4,999,291 and 4,810,643), GM-CSF (WO 85/04188), tumor necrosis factors (TNFs) (Jayaraman et al., 1990, *J. Immunology* 144:942–951), CD3 (Krissanen et al., 1987, *Immunogenetics* 26:258–266, 1987), ICAM-1 (Altman et al., 1989, *Nature* 338:512–514; Simmons et al., 1988, *Nature* 331:624–627), ICAM-2, LFA-1, LFA-3 (Wallner et al., 1987, *J. Exp. Med.* 166(4):923–932), MHC class I molecules, MHC class II molecules, B7.1-.3, $_2$-microglobulin (Parnes et al., 1981, *Proc. Natl. Acad. Sci.* 78:2253–2257), chaperones such as calnexin, MHC linked transporter proteins or analogs thereof (Powis et al., 1991, *Nature* 354:528–531, 1991).

Genes encoding any of the cytokine and immunomodulatory proteins described herein can be expressed in a gene delivery vehicle of the invention. Other forms of these cytokines which are known to those of skill in the art can also be used. For instance, nucleic acid sequences encoding native IL-2 and gamma-interferon can be obtained as described in U.S. Pat. Nos. 4,738,927 and 5,326,859, respectively, while useful muteins of these proteins can be obtained as described in U.S. Pat. No. 4,853,332. As an additional example, nucleic acid sequences encoding the short and long forms of mCSF can be obtained as described in U.S. Pat. Nos. 4,847,201 and 4,879,227, respectively.

Other nucleic acid molecules that encode cytokines, as well as other nucleic acid molecules that are advantageous for use within the present invention, may be readily obtained from a variety of sources, including, for example, depositories such as the American Type Culture Collection (ATCC, Rockville, Md.), or from commercial sources such as British Bio-Technology Limited (Cowley, Oxford England). Representative examples include BBG 12 (containing the GM-CSF gene coding for the mature protein of 127 amino acids), BBG 6 (which contains sequences encoding gamma interferon), ATCC No. 39656 (which contains sequences encoding TNF), ATCC No. 20663 (which contains sequences encoding alpha interferon), ATCC Nos. 31902, 31902 and 39517 (which contains sequences encoding beta interferon), ATCC No 67024 (which contains a sequence which encodes Interleukin-1b), ATCC Nos. 39405, 39452, 39516, 39626 and 39673 (which contains sequences encoding Interleukin-2), ATCC Nos. 59399, 59398, and 67326

(which contain sequences encoding Interleukin-3), ATCC No. 57592 (which contains sequences encoding Interleukin4), ATCC Nos. 59394 and 59395 (which contain sequences encoding Interleukin-5), and ATCC No. 67153 (which contains sequences encoding Interleukin-6).

Gene delivery vehicles expressing the above cytokines are useful in the treatment of a variety of disorders. For example, see PCT publication number US94/02951 entitled "Compositions and Methods for Cancer Immunotherapy" for a description of gene therapy treatment of malignancy.

15. Neurological Disorders and Diseases

Polynucleotides encoding tyrosine hydroxylase can be useful in treating Parkinson disease.

For stroke or any acute brain injuries, polynucleotides encoding IGF-1, bFGF, vascular endothelial growth factor (VEGF) are useful.

16. Pulmonary Disorders

For treating emphysema, polynucleotides encoding α1-anti-trypsin are useful.

For treating lung fibrosis, polynucleotides encoding superoxide dismutase (SOD) are useful.

For treating cystic fibrosis, polynucleotides encoding CFTR are useful.

ADDITIONAL AGENTS

Additional agents can be included with the desired polynucleotides to be delivered. These additional agents can facilitate endocytosis of the desired nucleic acids or aid binding of the nucleic acids to the cell surface or both, for example.

A. Polypeptides

One example are polypeptides which include, without limitation: asialoorosomucoid (ASOR); transferrin; asialoglycoproteins; antibodies; antibody fragments; ferritin; interleukins; interferons, granulocyte, macrophage colony stimulating factor (GM-CSF), granulocyte colony stimulating factor (G-CSF), macrophage colony stimulating factor (M-CSF), stem cell factor and erythropoietin. Viral antigens, such as envelope proteins, can also be used. Also, proteins from other invasive organisms, such as the 17 amino acid peptide from the circumsporozoite protein of plasmodium falciparum known as RII.

B. Hormones, Vitamins, Etc.

Other groups that can be included are, for example: hormones, steroids, androgens, estrogens, thyroid hormone, or vitamins, folic acid.

C. Polyalkylenes, Polysaccharides, Etc.

Polyalkylene glycols can be included with the desired polynucleotides. In a preferred embodiment, the polyalkylene glycol is polyethlylene glycol. In addition, mono-, di-, or polysaccarides can be included. In a preferred embodiment of this aspect, the polysaccharide is dextran or DEAE-dextran. Also, chitosan and poly(lactide-co-glycolide)

D. Lipids and Liposomes

The desired polynucleotide can also be encapsulated in lipids or packaged in liposomes prior to delivery to the subject or to cells derived therefrom.

Lipid encapsulation is generally accomplished using liposomes which are able to stably bind or entrap and retain nucleic acid. The ratio of condensed polynucleotide to lipid preparation can vary but will generally be around 1:1 (mg DNA:micromoles lipid), or more of lipid. For a review of the use of liposomes as carriers for delivery of nucleic acids, see, Hug and Sleight, 1991, Biochim. Biophys. Acta. 1097:1–17; Straubinger et al., in METHODS OF ENZYMOLOGY (1983), Vol. 101, pp. 512–527.

Liposomal preparations for use in the instant invention include cationic (positively charged), anionic (negatively charged) and neutral preparations. Cationic liposomes have been shown to mediate intracellular delivery of plasmid DNA (Feigner et al., 1987, Proc. Natl. Acad. Sci. USA 84:7413–7416); mRNA (Malone et al., 1989, Proc. Natl. Acad. Sci. USA 86:6077–6081); and purified transcription factors (Debs et al., 1990, J. Biol. Chem. 265:10189–10192), in functional form.

Cationic liposomes are readily available. For example, N[1-2,3-dioleyloxy)propyl]-N,N,N-triethylammonium (DOTMA) liposomes are available under the product line Lipofectin®, from GIBCO BRL, Grand Island, N.Y. (See, also, Felgner et al., 1987, Proc. Natl. Acad. Sci. USA 84:7413–7416). Other commercially available liposomes include transfectace (DDAB/DOPE) and DOTAP/DOPE (Boerhinger). Other cationic liposomes can be prepared from readily available materials using techniques well known in the art. See, e.g., Szoka et al., 1978, Proc. Natl. Acad. Sci. USA 75:4194–4198; PCT Publication No. WO 90/11092 for a description of the synthesis of DOTAP (1,2-bis(oleoyloxy)-3-(trimethylammonio)propane) liposomes.

Similarly, anionic and neutral liposomes are readily available, such as from Avanti Polar Lipids (Birmingham, Ala.), or can be easily prepared using readily available materials. Such materials include phosphatidyl choline, cholesterol, phosphatidyl ethanolamine, dioleoylphosphatidyl choline (DOPC), dioleoylphosphatidyl glycerol (DOPG), dioleoylphoshatidyl ethanolamine (DOPE), among others. These materials can also be mixed with the DOTMA and DOTAP starting materials in appropriate ratios. Methods for making liposomes using these materials are well known in the art.

The liposomes can comprise multilamellar vesicles (MLVs), small unilamellar vesicles (SUVs), or large unilamellar vesicles (LUVs). The various liposome-nucleic acid complexes are prepared using methods known in the art. See, e.g., Straubinger et al., in METHODS OF IMMUNOLOGY (1983), Vol. 101, pp. 512–527; Szoka et al., 1978, Proc. Natl. Acad. Sci. USA 75:4194–4198; Papahadjopoulos et al., 1975, Biochim. Biophys. Acta 394:483; Wilson et al., 1979, Cell 17:77; Deamer and Bangham, 1976, Biochim. Biophys. Acta 443:629; Ostro et al., 1977, Biochem. Biophys. Res. Commun. 76:836; Fraley et al, 1979, Proc. Natl. Acad. Sci. USA 76:3348); Enoch and Strittmatter, 1979, Proc. Natl. Acad. Sci. USA 76:145); Fraley et al., 1980, J. Biol. Chem. 255:10431; Szoka and Papahadjopoulos, 1978, Proc. Natl. Acad. Sci. USA 75:145; and Schaefer-Ridder et al., 1982, Science 215:166.

E. Lipoproteins

In addition, lipoproteins can be included with the polynucleotide to be delivered. Examples of lipoproteins to be utilized include: chylomicrons, HDL, IDL, LDL, and VLDL. Mutants, fragments, or fusions of these proteins can also be used. Also, modifications of naturally occurring lipoproteins can be used, such as acetylated LDL. These lipoproteins can target the delivery of polynucleotides to cells expressing lipoprotein receptors. Preferably, if lipoproteins are included with the polynucleotide to be delivered, no other targeting ligand is included in the composition.

If lipoproteins are included with the desired polynucleotides to be delivered, preferably, the composition comprises: (1) lipoprotein; (2) polynucleotide; and (3) a polynucleotide binding molecule.

Naturally occurring lipoproteins comprise a lipid and a protein portion. The protein portion are known as apoproteins. At the present, apoproteins A, B, C, D, and E have been isolated and identified. At least two of these contain several proteins, designated by Roman numerals, AI, AII, AIV; CI, CII, CIII.

A lipoprotein can comprise more than one apoprotein. For example, naturally occurring chylomicrons comprise A, B, C, and E, over time these lipoproteins lose A and acquire C and E apoproteins. VLDL comprises A, B, C, and E apoproteins, LDL comprises apoprotein B; and HDL comprises apoproteins A, C, and E.

The amino acids of these apoproteins are known and are described in, for example, Breslow, 1985, Annu Rev. Biochem 54:699; Law et al., 1986, *Adv. Exp Med. Biol.* 151:162; Chen et al., 1986, *J Biol Chem* 261: 12918; Kane et al., 1980, *Proc Natl Acad Sci USA* 77:2465; and Utermann et al., 1984, *Hum Genet* 65:232.

Lipoproteins contain a variety of lipids including, triglycerides, cholesterol (free and esters), and phopholipids. The composition of the lipids varies in naturally occurring lipoproteins. For example, chylomicrons comprise mainly triglycerides. A more detailed description of the lipid content of naturally occurring lipoproteins can be found, for example, in *Meth. Enzym.* 128 (1986). The composition of the lipids are chosen to aid in conformation of the apoprotein for receptor binding activity. The composition of lipids can also be chosen to facilitate hydrophobic interaction and association with the polynucleotide binding molecule.

Naturally occurring lipoproteins can be isolated from serum by ultracentrifugation, for instance. Such methods are described in *Meth. Enzy., supra; Pitas et al.,* 1980, *J. Biochem.* 255:5454–5460; and Mahey et al., 1979, *J. Clin. Invest* 64:743–750.

Lipoproteins can also be produced by in vitro or recombinant methods by expression of the apoprotein genes in a desired host cell. See, for example, Atkinson et al., 1986, *Annu Rev Biophys Chem* 15:403, and Radding et al., 1958, *Biochim. Biophys Acta* 30:443.

Lipoproteins can also be purchased from commercial suppliers, such as Biomedical Technologies, Inc., Stoughton, Mass., USA.

Mutants, fragments and fusion of the naturally occurring apoproteins are useful for delivery of polynucleotides. These polypeptides will retain more than about 80% amino acid identity; more typically, more than about 85%; even more typically, at least 90%. Preferably, these polypeptides will exhibit more than about 92% amino acid sequence identity with naturally occurring lipoproteins or fragment thereof; more preferably, more than about 94%; even more preferably, more than about 96%; even more preferably, more than about 98%; even more preferably, more than about 99% sequence identity.

Such mutants, fragments and fusions can be constructed by altering the polynucleotides encoding the desired lipoproteins by recombinant DNA techniques. See, for example, Sambrook et al., (1989) Molecular Cloning, A Laboratory Manual, 2d edition (Cold Spring Harbor Press, Cold Spring Harbor, N.Y.). These polynucleotides can be inserted into expression vectors and host cells can be utilized to produce the desired apoprotein.

In addition, naturally occurring lipoproteins, mutants, fragments, and fusions can be chemically altered. For example, acetylated LDL has biological activity. See, for example, Nagelkerke et al., 1983, *J. Biol. Chem.* 258(20): 12221–12227; Weisgraber et al., 1978, *J. Biol. Chem.* 253:9053–9062; Voyta et al., 1984, *J. Cell Biol.* 99:2034–2040; Goldstein et al., 1979, *Proc. Natl. Acad. Sci. USA* 76:333–337; and Pitas, 1981, *Arterosclerosis* 1:177–185.

Chemically modified lipoproteins can also be purchased from commercial suppliers, such as Biomedical Technologies, Inc., Stoughton, Mass., USA.

All of these polypeptides exhibit receptor binding properties of naturally occurring lipoproteins. Usually, such polypeptides exhibit at least about 20% receptor binding of naturally occurring lipoproteins. More typically, the polypeptides exhibit at least about 40%, even more typically the polypeptides exhibit at least about 60%; even more typically, at least about 70%; even more typically, at least about 80%; even more typically, at least about 85%; even more typically, at least about 90%; even more typically, at least about 95% receptor binding of the naturally occurring lipoproteins.

Typically, lipoproteins are present in an amount effective to increase the frequency of incorporation of polynucleotides into a cell. Such an amount is sufficient to increase the frequency of incorporation of polynucleotides into a cell by at least 10%, compared to the frequency of incoporation of naked polynucleotides; more usually, at least 15%; even more usually, 20%; even more usually, at least 30%. The increase can be between 40 to 100%, and even 1000% and 10000% increase.

"Polynucleotide binding molecule" refers to those compounds that associate with polynucleotides, and the association is not sequence specific. For example, such molecules can (1) aid in neutralizing the electrical charge of polynucleotide, or (2) facilitate condensation of nucleotides, or (3) inhibit serum or nuclease degradation. Optionally, polynucleotide binding molecules can interact with lipoproteins by either hydrophobic association or by charge. Polynucleotide binding molecules include, without limitation, polypeptides, mineral compounds, vitamins, etc.

Examples of polynucleotide binding molecules include: polylysine, polyarginine, polyornithine, and protamine. Examples of organic polycations include: spermine, spermidine, and purtrescine. Other examples include histones, protamines, human serum albumin, DNA binding proteins, non-histone chromosomal proteins, coat proteins from DNA viruses, such as $\phi$X174, transcriptional factors also contain domains that bind DNA and therefore may be useful as nucleic aid condensing agents. Briefly, transcriptional factors such as C/CEBP, c-jun, c-fos, AP-1, AP-2, AP-3, CPF, Prot-1, Sp-1, Oct-1, Oct-2, CREP, and TFIID contain basic domains that bind DNA sequences.

Examples of other positively charged moieties include polybrene, DEAE-dextran, and cationic lipids. Useful cationic lipids and liposomes are described above. Lipids and liposomes are not used in this aspect of the invention to encapsulate both polynucleotide and lipoprotein. The lipoprotein must be exposed to bind the its cell surface receptor.

Other synthetic compounds that are capable of binding negatively charged polynucleotides are useful, such as polymers of N-substituted glycines and others, as described below.

In a composition with a lipoprotein, the polynucleotide binding molecule can be present in an amount effective to neutralize the polynucleotide. However, the polynucleotide binding molecule also can be in excess of an effective amount to neutralize the polynucleotide to be delivered. Such an excess can produce a net positive electrical charge when complexed with the polynucleotides to be delivered. The positively charged complex can then interact with lipoproteins that comprise negatively charged lipids, such as phospholipids.

Typically, the polynucleotide binding molecule is in excess when the amount is 10% greater than the amount to neutralize the polynucleotide charge; more typically, the amount is 50% greater; even more typically, 100% greater; even more typically, 150% greater; even more typically, 200% greater; even more typically, 500% greater; even more typically, 20,000% greater; even more typically, 22,000% greater; even more typically, 25,000% greater; even more typically, 30,000% greater; even more typically, more than 40,000% greater than the amount effective to neutralize the electrical charge of the desired polynucleotide.

POLYCATIONIC AGENTS

Polycationic agents can be included, with or without lipoprotein, in a composition with the desired polynucleotide to be delivered.

Functional Properties
A. Net Positive Charge

Polycationic agents typically exhibit a net positive charge at physiological relevant pH and are capable of neutralizing the electrical charge of nucleic acids to facilitate delivery to a desired location. These agents have both in vitro, ex vivo, and in vivo applications. For example, these polycationic agents can be used to transfect cells used to produce recombinant proteins. Alternatively, the instant polycationic agents can be used to deliver nucleic acids to a living subject either intramuscularly, subcutaneously, etc.

Physiological relevant pH varies somewhat between in vitro and in vivo applications. Typically, physiological pH is at least 5.5; more typically, at least 6.0; even more typically, at least 6.5. Usually, physiologically relevant pH is no more than 8.5; more usually, no more than 8.0; even more usually, no more than 7.5.

Preferably, the isoelectric point of the instant polycationic agents to neutralize nucleic acids is at least 9.

B. Non-Toxicity and Non-Immunogenic Properties

The composition of the polycationic agents of the invention will exhibit the toxicity and immunogenic properties desired. In vitro cell culture will have different immunogenic constraints than in vivo mammalian applications.

The instant polycationic agents can be easily tested for toxicity. For example, the agents can be added to medium for cells used in the in vitro assays, such as cos-7, Chinese Hamster Ovary cells, etc. Alternatively, the agents can be tested in standard animal tests for safety.

C. Condensation Properties

Due to the electric charge, a subset of these polycationic agents are capable of condensing the desired nucleic acids to a compact size to facilitate delivery. Typically, condensation "collapses" polynucleotides or nucleic acids into macromolecular structures, commonly into a toroid form. The smaller size of condensed nucleic acids eases delivery by facilitating, for example, packaging nucleic acids into liposomes and/or reducing exposure to proteases and/or nucleases.

The condensed nucleic acids exhibit different properties compared to "relaxed" nucleic acids, such as (1) a decrease in intercalation of ethidium bromide or other intercalating dye or (2) a reduced mobility in gel electrophoresis. Thus, condensation can be measured by at least two different assays, an intercalating dye assay or a band shift assay.

One type of intercalating dye assay uses ethidium bromide. In this assay, test nucleic acids, conveniently plasmid DNA, are mixed with polycationic agent in a ratio from about 1:1 to a 1:50 weight/weight ration of plasmid to condensing agent. Following incubation, ethidium bromide is added to the reaction to a final concentration of 1 $\mu$g/mL. If a nucleic acid such as RNA is used as the test nucleic acid, acridine orange may be used as the intercalating dye. The reaction mixtures are transferred into UV transparent plastic tubes spotted with 1% agarose gel, or placed upon UV transparent plastic and illuminated with 260 nm light. The emission from the DNA-ethidium bromide complex is recorded on film by a camera equipped with an appropriate UV filter. The ability of an agent to condense DNA is inversely proportional to the intensity of the fluorescence in each reaction mixture.

The more precise test is a band shift assay. Briefly, this assay is performed by incubating nucleic acids, either labeled or unlabeled, with various concentrations of candidate condensing agents. Test nucleic acids, conveniently plasmid DNA, and condensing agent are mixed at 1:1 to 1:50 w/w ratios. Following incubation, each sample is loaded on a 1% agarose gel and electrophoresed. the gel is then either stained with ethidium bromide or dried and autoradiographed. DNA condensation is determined by the inability to enter the gel compared to a non-condensed standard. Sufficient condensation is achieved when at least 90% of the DNA fails to enter the gel to any significant degree.

Condensation can also be measured by directly determining the size of the complex using a light scattering instrument such as the a Coulter N4MD submicron analyzer, for example. Polynucleotides and a condensing agent are incubated at an appropriate ratio, either alone or in the present of 2% PEG-2000 (Fisher Scientific), and 0.6 M NaCl., and then diluted into 3 ml of water. This dilute solution is analyzed by the Coulter counter which will detect particles with a mean size of 0–1,000 nanometers (nm). Condensing agents, such as poly-L-lysine, typically yield particles with a mean diameter of approximately 50–200 nm. See Lee et al., 1996, *J. Biol. Chem.* 271: 8481–8487.

D. Serum and/or Nuclease Protection Properties

The instant polycationic agents are capable of protecting nucleic acids from degradation in serum or from nucleases, including nucleases present in biological fluids, such as serum, prostate, synovial fluid, etc. One advantage of this type of protection is that smaller amounts of the desired nucleic acids are needed for efficient administration.

When present in effective amounts, these polycationic agents can inhibit serum degradation by at least 5 minutes as compared with uncomplexed nucleic acids; more usually, the amount used is sufficient to inhibit degradation by at least 10 minutes; even more usually; the amount used is sufficient to inhibit degradation by at least 30 minutes; even more usually, the amount used is sufficient to inhibit degradation by at least 45 minutes; even more usually, the amount used is sufficient to inhibit degradation by at least 60 minutes; even more usually, the amount used is sufficient to inhibit degradation by at least 90 minutes; and more usually, the amount used is sufficient to inhibit degradation by at least 120 minutes.

Increased serum protection can be measured simply by incubation of the polycation/polynucleotide complex with mouse serum, for example. Preferably, the serum will not be heat inactivated. After incubation, the mixture can be analyzed by gel electrophoresis to determine the quantity of the polynucleotides remaining after incubation.

Alternatively, nucleases can be added to the polycationic agent/nucleic acid complexes. The resulting mixture can be analyzed by gel electrophoresis to determine the amount of degradation. Other biological fluids, such as prostate fluid, can also be tested.

E. Mediating Entry of Polynucleotides into a Cell

The polycationic agents can mediate entry of polynucleotides into a cell. Incorporation of polynucleotides into a cell can be measured by either protein expression assays or polynucleotide hybridization techniques, for example.

One method of detecting frequency of incorporation is to include a gene that encodes a marker protein, such as luciferase. Cells that have incorporated the delivered polynucleotides will express the marker protein. The protein can be detected by standard immunoassays, or by biological or enzymatic activity, as in the case of luciferase.

Alternatively, standard hybridization techniques, such as Southern or Northern blots or polymerase chain reaction (PCR) techniques, can be used to detect the presence of the desired polynucleotides.

F. Additional Properties

To facilitate entry of nucleic acids to the interior of cells, the instant agents can be capable of (a) binding the polynucleotide to the cell surface;

(b) cell membrane destabilization;

(c) triggering endocytosis;

(d) endosome buffering capacity;

(e) releasing DNA/lipid complexes from endosomes; or (f) nuclear tropism.

Assays for detecting these characteristics are standard and known to those skilled in the art.

Physical Properties

The following physical characteristics are factors to consider when determining the composition of the polycationic agents:

(a) distance between the substituents and the backbone (b) the total length of the chain;

(b) hydrophobicity and/or aromacity;

(c) number of hydrogen bonding groups; and (c) charge, including
(i) type of charge group, (ii) density of charge and (iii) position.

Other relevant characteristics include structural flexibility. For example, a helical conformation of the polycationic agent may be preferred for some applications.

Specific dimensions to be considered include (a) the distance of phosphate groups in the polynucleotide of interest; and (b) the distance of monomer groups in the agents of interest.

Polypeptide Polycationic Agents

The following are examples of useful polypeptides as polycationic agents: polylysine, polyarginine, polyornithine, and protamine. Other examples include histones, protamines, human serum albumin, DNA binding proteins, non-histone chromosomal proteins, coat proteins from DNA viruses, such as φX174, transcriptional factors also contain domains that bind DNA and therefore may be useful as nucleic aid condensing agents. Briefly, transcriptional factors such as C/CEBP, c-jun, c-fos, AP-1, AP-2, AP-3, CPF, Prot-1, Sp-1, Oct-1, Oct-2, CREP, and TFIID contain basic domains that bind DNA sequences.

Organic polycationic agents include: spermine, spermidine, and putrescine.

The dimensions and of the physical properties of a polycationic agent can be extrapolated from the list above, to construct other polypeptide polycationic agents or to produce synthetic polycationic agents.

Synthetic Polycationic Agents

Synthetic polycationic agents which are useful include, for example, DEAE-dextran, polybrene. Lipofectin®, and lipofectAMINE™ are monomers that form polycationic complexes when combined with polynucleotides.

A preferred group of polycationic agents of the present invention have the following general formula (I):

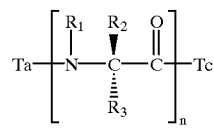

A preferred subset of these compounds include compounds having formula (I) where $R_2$ is hydrogen. Even more preferred are polymers comprising at least one natural amino acid. Also preferred are polymers where $R_2$ and $R_3$ are both hydrogen, also referred to as poly N-substituted glycines or poly NSGs.

A. Monomers

The polycationic agent of the invention comprises monomers with the following structure (II):

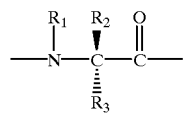

Generally, $R_1$, $R_2$, and $R_3$ are moieties each with a molecular weight from 1 to 250 daltons. More typically, the molecular weight is no more than 200; even more typically, no more than 175.

Typically, each monomer comprises one hydrogen at $R_1$, $R_2$, or $R_3$. More, typically, either $R_1$ and $R_3$ are both hydrogen, the structure of an L-amino acid; or $R_2$ and $R_3$ are both hydrogen, the structure of a NSG.

Monomers to be utilized in the polycationic agents can be either positively or negatively charged. Also, neutral substituents can also be utilized.

Degradation sites can be incorporated into the polymer, for example, by including substituents from a natural amino acid when $R_1$ and $R_3$ are hydrogen. These monomers can be positively or negatively charged, or neutral.

As a general rule, a basically charged monomer has a pKa value for the side chain of at least 7.5. Positively, or basically, charged monomers include without limitation those containing the following functional groups: amino, guanidino, hydrazido, and amidino. These functional groups can be either aromatic or aliphatic.

Positively charged monomers comprising hydrogen at $R_3$ and $R_1$, can be included in the polycationic agent, for example, as a degradation site. Such degradation site may aid in separation of the polycationic agent from the polynucleotide to permit further processing. For an L-amino acid like monomer, useful $R_2$ substitutents are, for example, from those found in naturally occurring amino acids, such as lysine and arginine. Also, sidechains from amino acid analogues can be used such as ornithine and canaline; or modifications of basic amino acids, such as homoarginine, and modifications of other amino acids such as guanidinovalinate, and aminoethylcysteine. The substitutents found in L-amino acids can also be incorporated at the $R_1$ and $R_3$ positions of the instant polycationic agents.

Naturally occurring amino acids and analogues are designated D-amino acids to indicate the chirality of these molecules. L-amino acids can also be incorporated as monomers into the polycationic agents. The substituents of L-amino acids can be, for example, the same as those named for the D-amino acids.

Preferable monomers include N-substituted glycine monomers. Exemplary N-substitutions include alkylphenyl, indolylalkyl, alkoxyphenyl, halophenylalkyl, and hydroxyphenylalkyl, as well as the N-substitutions shown below.

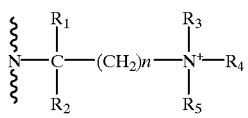

Alkylammonium,
where preferably $R_1$ = H;
 $R_2$ = H, $CH_3$;
 $R_3$, $R_4$, $R_5$ can each be $CH_3$, or $CH_3CH_2$; and
 n = 1–6.

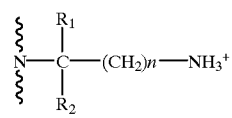

Aminoalkyl,
where preferably $R_1$ = H;
 $R_2$ = H, $CH_3$;
 n = 1–6.

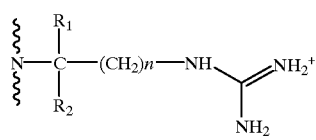

Guanidinoalkyl,
where preferably $R_1$ = H;
 $R_2$ = H, $CH_3$;
 n = 1–6.

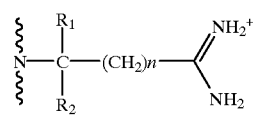

Amidinoalkyl,
where preferably $R_1$ = H;
 $R_2$ = H, $CH_3$;
 n = 1–6.

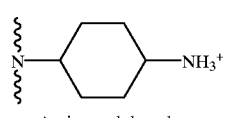

Aminocyclohexyl

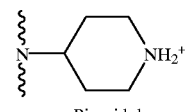

Piperidyl

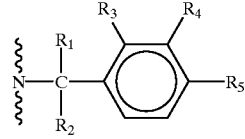

Guanidinobenzyl
where preferably $R_1$ = H; and
 $R_2$ = H, $CH_3$
 $R_3$, $R_4$, and $R_5$ each can be H or 

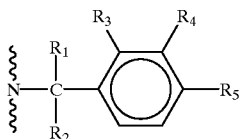

Amidinobenzyl
where preferably $R_1$ = H;
 $R_2$ = H, $CH_3$; and
 $R_3$, $R_4$, $R_5$ each can be 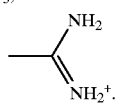

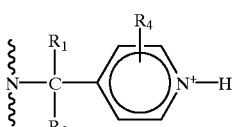

Pyridylmethyl
where preferably
 $R_1$ = H;
 $R_2$ = H, $CH_3$; and
 $R_4$ = H, $CH_3O$, Cl, F, Br, CH, $NO_2$, $CH_3$.

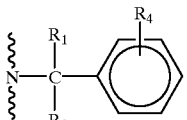

Aminobenzyl
where preferably
 $R_1$ = H;
 $R_2$ = H, $CH_3$; and
 $R_4$ = H, $CH_3O$, Cl, F, Br, CH, $NO_2$, $CH_3$.

The positively charged substituents described above can also be placed at the $R_2$ or $R_3$ positions of formulas (I) and (II).

The polycationic agents can comprise negatively charged or neutral monomers. As with the positively charged monomers, D-amino acid, L-amino acid, and NSGs are preferred to be incorporated as monomers.

The following are examples of such monomers:

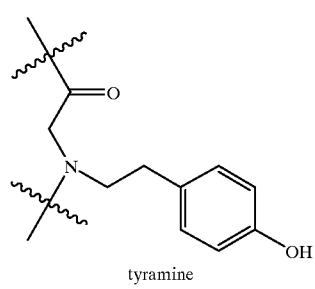

tyramine

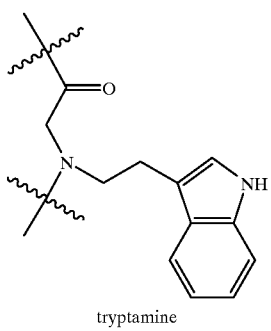
tryptamine

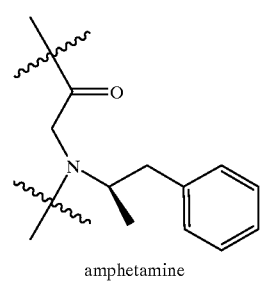
amphetamine

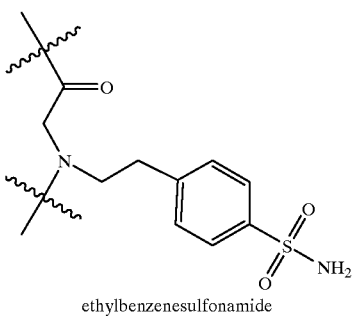
ethylbenzenesulfonamide

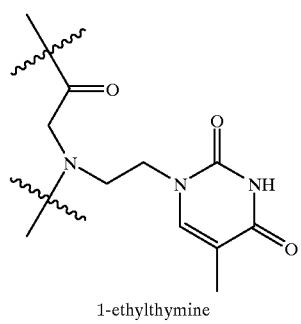
1-ethylthymine

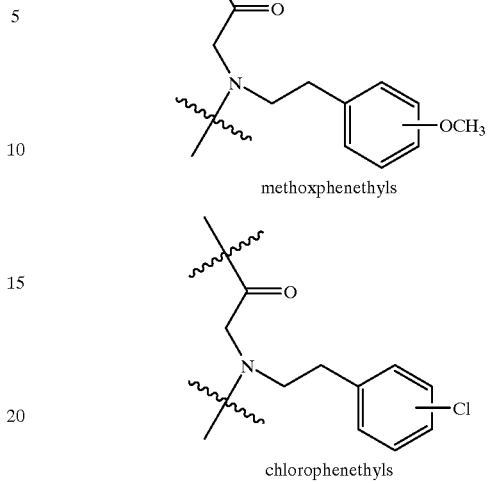
methoxphenethyls chlorophenethyls

B. Polycationic Polymers

Typically, the polycationic agents exhibit a predicted isoelectric point of at least 9, excluding the terminal groups. Further, the agents contain, excluding the terminal groups, at least 20% positively charged monomers; more typically, at least 25%; more typically, 30%; and preferably, at least 33% positively charged monomers. Typically, the agents do not comprise greater than 5% acidic monomers and preferably none.

The charge density and composition of the polycationic agent can be altered to accommodate the specific nucleic acid sequence, type, and other components included with the complex of nucleic acids and polycationic agent.

Usually, the length of the polymer is at least 8 monomers; even more usually, 12 monomers; even more usually, 18 monomers. More typically, the polycationic agents of the invention will be at least 24 monomer units in length; more typically, 30 monomer units; even more typically, 36 monomer units; even more typically, 48 monomer units. The polycationic agent can be up to 50 to 75 to 100 monomer units in length.

Preferably, the polycationic agent comprises monomers where all $R_2$ and $R_3$ are hydrogen. Even more preferably, where all $R_2$ and $R_3$ are hydrogen, the polycationic agent comprise repeating trimer units with the following monomer sequence (from amino to carboxy terminus): (1) neutral monomer, (2) neutral monomer, and (3) positively charged monomer.

Preferably, the neutral monomer comprises an aromatic group at the $R_1$ position; more preferably, wherein the aromatic group comprises a single ring; even more preferably, wherein the aromatic group is a six member ring.

Typically, the positively charged monomer is aminoalkyl at the $R_1$ position; more typically, the aminoalkyl comprises 1–6 carbon molecules; even more typically, the aminoalkyl is aminoethyl.

Typically, the polycationic agent comprises between 3 to 20 repeating trimers, trimers having two neutral and one positively charged $R_1$ groups are preferred, such as, for example, trimers having the sequence, neutral monomer, neutral monomer, positively charged monomer. More preferably, the polycationic agent comprises 5 to 18 trimers; preferably 8 to 16 trimers; and even more preferably, 12 to 16 trimers.

Optionally, the polycationic agent contains only positively charged monomers, excluding the terminal groups. Typically, such a polycationic agent comprises between 24 and 48 monomers; more typically, 30 to 40 monomers; even more typically, 36 monomers.

Polycationic agents of the present invention containing only positively charged monomers typically have guanidinoalkyl sidechains. Typically, the guanidinoalkyl sidechain comprises 1 to 6 carbon molecules. Preferably, the side chain is guanidino ethyl.

C. Neutral Polymers

A preferred group of neutral polymers of the present invention have the general formula (I):

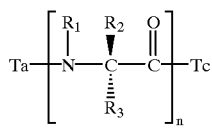

Preferably, $R_2$ is hydrogen. Even more preferred are polymers comprising at least one natural amino acid. Also preferred are polymers having formula (I) where $R_2$ and $R_3$ are hydrogen, also referred to as poly N-substituted glycines or poly NSGs.

Monomers employed in neutral polymers of the present invention have the same general formula as monomers employed in cationic polymers of the present invention, i.e.:

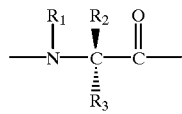

Generally, $R_1$, $R_2$, and $R_3$ are moieties each with a molecular weight from 1 to 250 daltons. More typically, the molecular weight is no more than 200; even more typically, no more than 175.

Typically, each monomer comprises one hydrogen at $R_1$, $R_2$, or $R_3$. More, typically, either $R_1$ and $R_3$ are both hydrogen, the structure of a L-amino acid; or $R_2$ and $R_3$ are both hydrogen, the structure of a NSG.

Monomers to be utilized in the neutral agents can be either positively or negatively charged. Also, neutral substituents can also be utilized. Neutral polymers exhibit no net positive or negative charge, excluding the terminal groups.

Degradation sites can be incorporated into the polymers by using naturally occuring amino acid substituents in monomers when $R_1$ and $R_3$ are hydrogen.

Naturally occurring amino acids and analogues are designated D-amino acids to indicate the chirality of these molecules. L-amino acids can also incorporated as monomers into the neutral polymers. The substituents of L-amino acids can be, for example, the same as those named for the D-amino acids.

Preferred monomers include N-substituted glycine monomers, and monomers that are capable of forming hydrogen bonds and/or ionic bonds with the polynucleotides to be delivered.

Examples of monomers for the neutral polymers include those described above and in the Examples below.

D. Linking Polymers Together

Polymers can be linked together incorporating terminating groups or sidechains that permit cross-linking of the polymers. For example, polymers can be linked by a disulfide bond. Other terminating groups useful for coupling polymers include, carbonate, urea, and the like.

E. Additional Groups to be Incorporated into the Polymer

Additional components can be included in the polycationic agents of the instant invention, such as targeting ligands. Such additional groups can facilitate endocytosis of the desired nucleic acids or aid binding of the nucleic acids to the cell surface.

Polypeptides can be incorporated into the polycationic agents. Examples include, without limitation: asialooroso-mucoid (ASOR); transferrin; asialoglycoproteins; antibodies; antibody fragments; ferritin; interleukins; interferons, granulocyte, macrophage colony stimulating factor (GM-CSF), granulocyte colony stimulating factor (G-CSF), macrophage colony stimulating factor (M-CSF), stem cell factor and erythropoietin. Viral antigens, such as envelope proteins, can also be used. Also, proteins from other invasive organisms are useful, such as the 17 amino acid peptide from the circumsporozoite protein of plasmodium falciparum known as RII.

In addition, lipoproteins can be incorporated into the polycationic agent, such as low density lipoprotein, high density lipoprotein, or very low density lipoprotein. Mutants, fragments, or fusions of these proteins can also be used.

Other groups that can be incorporated include without limitation: hormones, steroids, androgens, estrogens, thyroid hormone, or vitamins, folic acid. Folic acid can be incorporated into the polycationic agent according, for example, to Mislick et al., 1995, T. J. Bioconjugate Chem. 6:512.

Also, the polycationic agents of the instant invention can be chemically conjugated with polyalkylene glycol. In a preferred embodiment, the polyalkylene glycol is polyethlylene glycol. PEG can be incorporated with a polycation agent according, for example, to Lu et al., 1994, Int. J. Pept. Protein Res. 43:127.

In addition, the polycationic agent can be chemically conjugated with mono-, di-, or polysaccharide. In a preferred embodiment of this aspect, the polysaccharide is dextran.

These additional groups can be incorporated within the polycationic agent. For example, $R_1$, $R_2$, and $R_3$ can be a substituent that is capable of being activated to cross link with any one of the above groups. For example, a thiol group could be included to cross link with another group to form a disulfide bond.

F. Terminal Groups

The terminal groups of the instant polycationic agents can be chosen as convenient. Suitable terminal groups (i.e., Ta and Tc) include, for example, —$NH_2$, —OH, —SH, and —COOH. Terminal groups can be selected to enhance the targeting properties of the polycationic agent and can be any of the additional groups described above.

The additional groups described above can be incorporated at the terminus of the polycationic agent. For example, the polycationic agent can be (1) acylated with a variety of carboxylic acids; (2) sulfonylated with sulfonyl chlorides; or (3) derivatized with isocyanates or isothiocyanates. Once activated, the terminus can be reacted with any of the above-mentioned groups, such as a polypeptide, such as low density lipoprotein, or folic acid.

One means of adding a terminal group to the polycationic agent is, for example, is (1) to acylate the amino terminus with Fmoc-amino-hexanoic acid; and (2) to remove the protecting group, Fmoc, to generate a primary amine, which can be further functionalized.

Alternatively, the amino-terminal groups can include, without limitation: acyl, such as acetyl, benzoyl; or sulfonyl, such as dansyl.

Carboxy terminal groups can include, for example, amide or alkyl amide.

Synthesis of Polycationic Agents

Polycationic agents of the present invention can be synthesized by either solid or solution phase methods. The following is a solid phase method for the synthesis of NSGs, which can be generally used for a wide variety of side-chain substitutents. This method can be performed utilizing automated peptide synthesis instrumentation to permit rapid synthesis of polycationic agents of interest. Such instruments are commercially available from, for example, Applied Biosystems and Milligen.

A. Two Step Monomer Assembly

A method of synthesis is to assemble the monomer from two submonomers in the course of extending a polymer comprising an NSG monomer. This technique is described in Zuckermann et al., 1992, *J Amer Chem Soc* 114(26):10646–10647, and Zuckermann et al., PCT Patent Publication No. WO 94/06451. The NSGs can also be considered to be an alternating condensation of copolymer of an acylating agent and an amine.

The direction of polymer synthesis with the submonomers occurs in the carboxy to amino direction. The solid-phase assembly for each monomer, in the course of polymer formation, eliminates the need for Nα-protected monomers, as only reactive side-chain functionalities need to be protected.

Each monomer addition comprises two steps, an acylation step and a nucleophilic displacement step as shown in FIG. 1.

Specifically, each cycle of monomer addition consists of two steps:

(1) acylation of a secondary amine bound to the support with an acylating agent comprising a leaving group capable of nucleophilic displacement by an amine and a carbonyl group, preferably carboxyl. An example is a haloacetic acid; and (2) nucleophilic displacement of the leaving group with a sufficient amount of a submonomer comprising a primary amino group to introduce a side-chain. The amino group containing submonomer can be an alkoxyamine, semicarbazide, acyl hydrazide, substituted hydrazine or the like.

Acylation can be activitated with carbodiimide or other suitable carboxylate activation method.

The efficiency of the displacement is modulated by the choice of halide, e.g., I>Cl. Protection of aliphatic hydroxyl groups, carboxylic acids, carboxy, thiol, amino, some heterocycles, and other reactive side-chain functionalities is preferred to minimize undesired side reactions. However, the mild reactivity of some side-chain moieties toward displacement or acylation may allow their use without protection., e.g., indole, imidazole, and phenol.

B. Three Step Monomer Assembly

Figure 2:
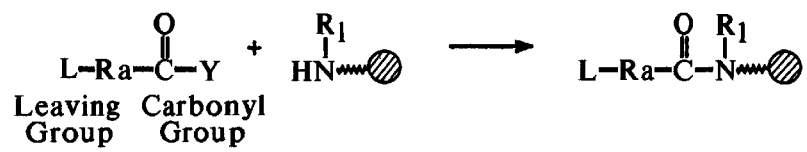
FIG. 2 is a schematic of a three-step monomer assembly reaction scheme.
Figure 2:
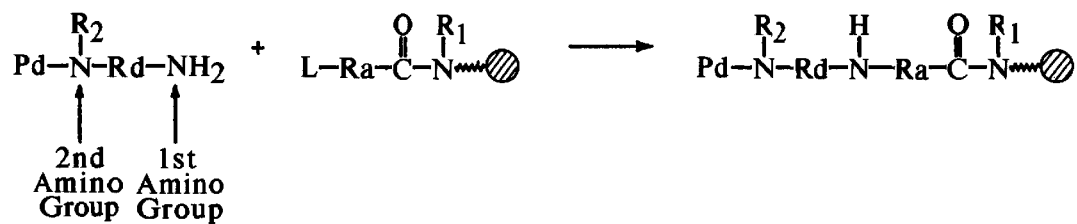
Figure 2:
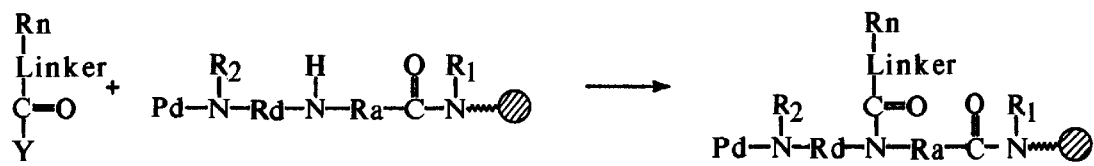
Figure 3:
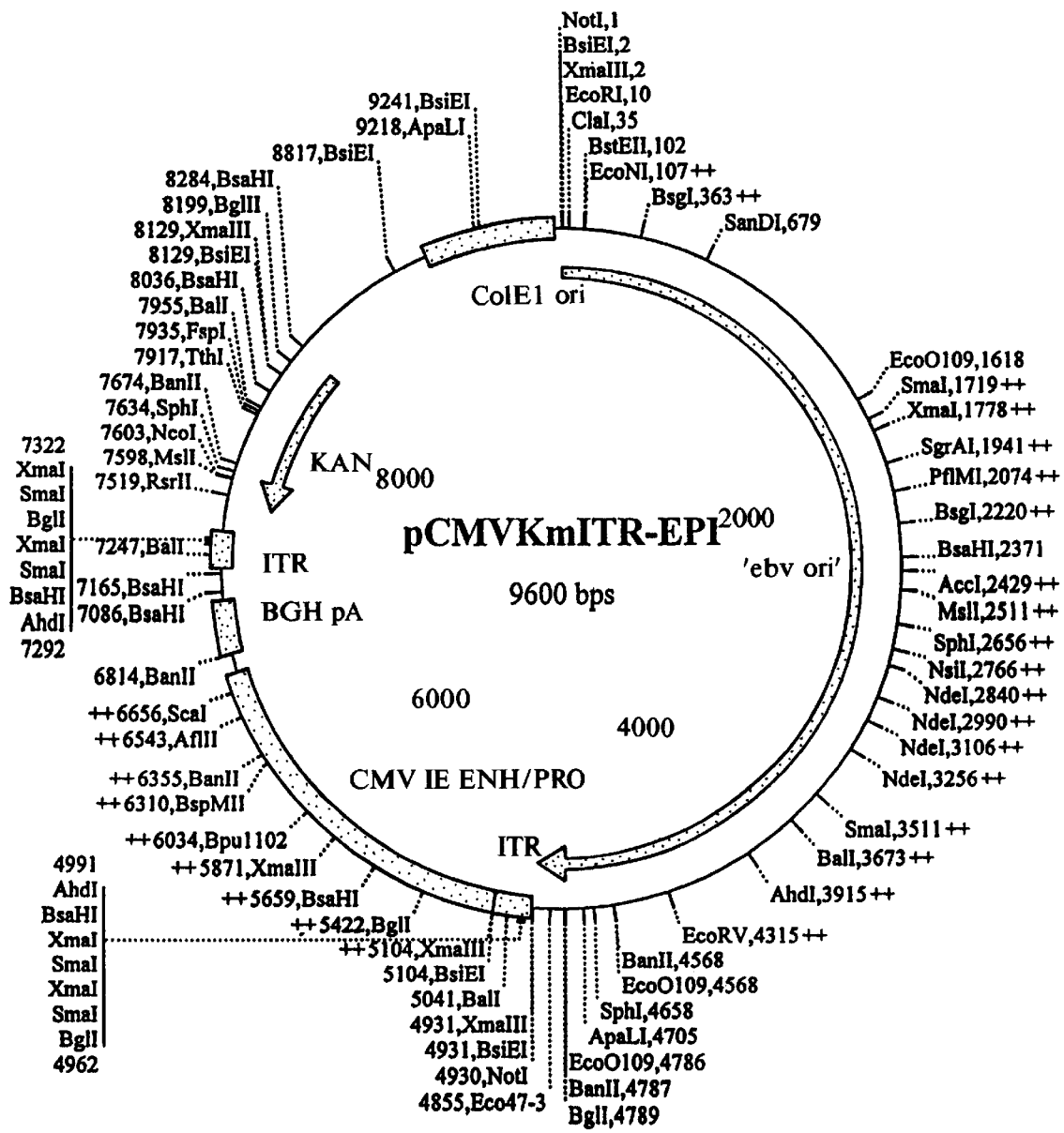
FIG. 3 is a plasmid map of vector pCMVKmITR-EPI.

NSGs can also be constructed utilizing a three step method for assembling each monomer as the polymer is extended. The backbone of the monomer of first extended by acylation step followed by a nucleophilic displacement. The side chain is introduced by a second acylation step. The reaction scheme is shown in FIG. 2.

The backbone of the monomer is assembled in the first two steps of the synthesis cycle. The first reaction is an acylation step where the carbonyl group of the acylating agent reacts with an amine. The acylating agent comprises a carbonyl group; a backbone, $R_a$; and a leaving group, L. Preferably, the carbonyl group is carboxyl.

The second step is a nucleophilic displacement of the leaving group by the first amino group of the displacing agent. The displacing agent comprises a first and a second amino group and a backbone, $R_d$. The first amino group is a primary amine, and the second step produces a secondary amine.

The third step is another acylation in which the another acylating submonomer reacts with the first amino group of the displacing agent to produce a tertiary amide. The acylation agent comprises a carbonyl group; an optional linker; and a sidechain. Preferably, the carbonyl group is carboxyl.

Pharmaceutical Compositions

The polycationic agent/polynucleotide complexes, whether or not encapsulated in liposomes, may be administered in pharmaceutical compositions. The pharmaceutical compositions comprise a therapeutically effective amount of nucleic acids.

The term "therapeutically effective amount" as used herein refers to an amount of a therapeutic agent sufficient to detectably treat, ameliorate, or prevent a particular disease or condition, i.e., an amount sufficient to induce a detectable therapeutic or preventative effect. The effect may include, for example, chemical markers or antigen levels. Therapeutic effects also include reduction in physical symptoms, such as decreased body temperature. The precise effective amount for a subject will depend upon the subject's size and health, the nature and extent of the cardiovascular condition, and the therapeutics or combination of therapeutics selected for administration. Thus, it is not useful to specify an exact effective amount in advance. However, the effective amount for a given situation can be determined by routine experimentation and is within the judgment of the clinician. For purposes of the present invention, an effective dose will be from about 0.01 mg/kg to 50 mg/kg or 0.05 mg/kg to about 10 mg/kg of the DNA constructs in the individual to which it is administered.

A pharmaceutical composition can also contain a pharmaceutically acceptable carrier. The term "pharmaceutically acceptable carrier" refers to a carrier for administration of a therapeutic agent, such as antibodies or a polypeptide, genes, and other therapeutic agents. The term refers to any pharmaceutical carrier that does not itself induce the production of antibodies harmful to the individual receiving the composition, and which may be administered without undue toxicity. Suitable carriers may be large, slowly metabolized macromolecules such as proteins, polysaccharides, polylactic acids, polyglycolic acids, polymeric amino acids, amino acid copolymers, and inactive virus particles. Such carriers are well known to those of ordinary skill in the art.

Pharmaceutically acceptable salts can be used therein, for example, mineral acid salts such as hydrochlorides, hydrobromides, phosphates, sulfates, and the like; and the salts of organic acids such as acetates, propionates, malonates, benzoates, and the like. A thorough discussion of pharmaceutically acceptable excipients is available in *Remington's Pharmaceutical Sciences* (Mack Pub. Co., New Jersey 1991).

Pharmaceutically acceptable carriers in therapeutic compositions may contain liquids such as water, saline, glycerol and ethanol. Additionally, auxiliary substances, such as wetting or emulsifying agents, pH buffering substances, and the like, may be present in such vehicles. Typically, the therapeutic compositions are prepared as injectables, either as liquid solutions or suspensions; solid forms suitable for solution in, or suspension in, liquid vehicles prior to injection may also be prepared. Liposomes are included within the definition of a pharmaceutically acceptable carrier.

Delivery Methods

Once formulated, the compositions of the invention can be administered (1) directly to the subject; (2) delivered ex vivo, to cells derived from the subject; or (3) in vitro for expression of recombinant proteins. The subjects to be treated can be mammals or birds. Also, human subjects can be treated.

Direct delivery of the compositions will generally be accomplished by injection, either subcutaneously, intraperitoneally, intravenously or intramuscularly or delivered to the interstitial space of a tissue. The compositions can also be administered into a tumor or lesion. Other modes of administration include oral and pulmonary administration, suppositories, and transdermal applications, needles, and gene guns or hyposprays. Dosage treatment may be a single dose schedule or a multiple dose schedule.

Methods for the ex vivo delivery and reimplantation of transformed cells into a subject are known in the art and described in e.g., International Publication No. WO 93/14778 (published Aug. 5, 1993). Examples of cells useful in ex vivo applications include, for example, stem cells, particularly hematopoetic, lymph cells, macrophages, dendritic cells, or tumor cells.

Generally, delivery of nucleic acids for both ex vivo and in vitro applications can be accomplished by the following procedures, for example, dextran-mediated transfection, calcium phosphate precipitation, polybrene mediated transfection, protoplast fusion, electroporation, encapsulation of the polynucleotide(s) in liposomes, and direct microinjection of the DNA into nuclei, all well known in the art.

The examples presented below are provided as a further guide to the practitioner of ordinary skill in the art, and are not to be construed as limiting the invention in any way.

EXAMPLE 1

Synthesis of Polycationic Agents

This example describes the synthesis of polycationic agents with the following structure:

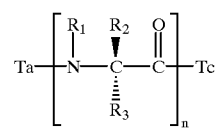

where $R_3$ and $R_2$ are hydrogen for all monomers. All polymers described in this example terminate in an amino and a carboxyl group unless specified, such as a folate terminating group.

The polycationic agents described below were synthesized according to the procedures described in Figliozzi et al., 1996, *Meth. Enzy.* 267:437–447, and Zuckermann et al., 1992, *J. Amer. Chem. Soc.* 114(26):10646–10647.

All polymers were synthesized using bromoacetic acid and primary amines. The following are substitutents of the primary amines to be positioned at $R_1$ to construct the polycationic agents:

---

Cationic Sidechains

---

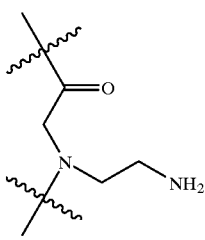

P = aminoethyl

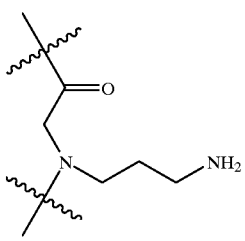

Pr = aminopropyl

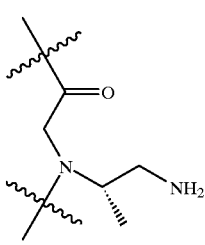

P* = (S)-1-methylethylenediamine

-continued
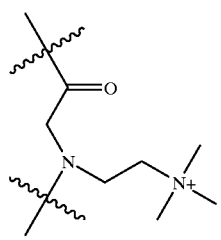
Q = trimethylaminoethyl
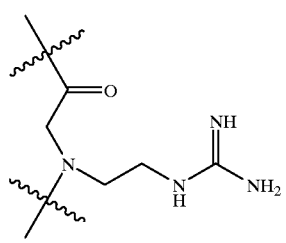
G = guanidinoethyl
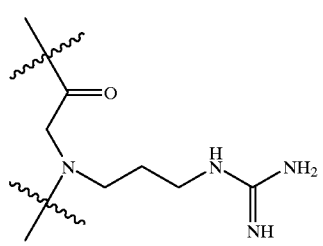
Gp = guanidinopropyl
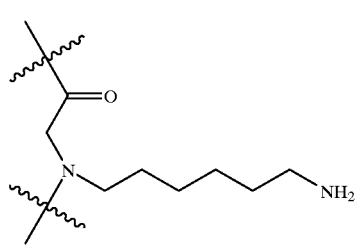
P' = aminohexyl
Other Sidechains
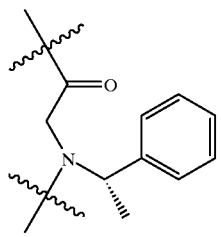
H = (S)-α-methylbenzyl
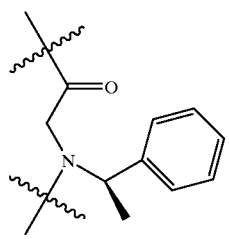
H+ = (R)-α-methylbenzyl -continued
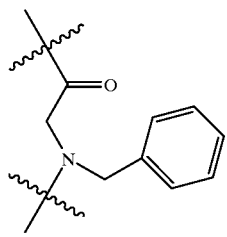
Bn = benzyl
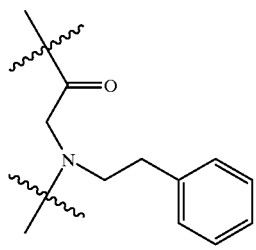
Ph = phenethyl
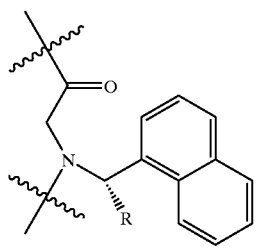
NM = naphthylmethyl (R = H)
sN = (S)-α-methylnaphthylmethyl (R = CH$_3$)
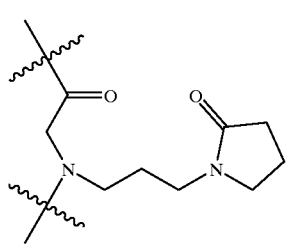
Py = N-pyrrolidonopropyl
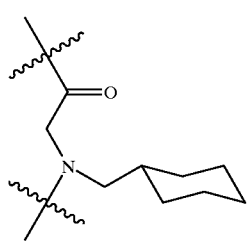
Chm = cyclohexylmethyl
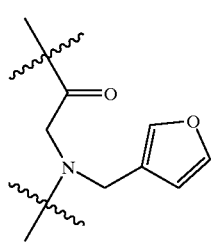
Ff = furfurylmethyl -continued
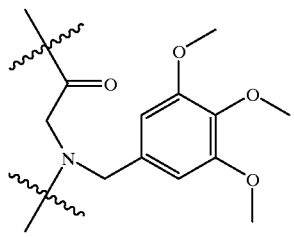
Tmb = 3,4,5-trimethoxybenzyl
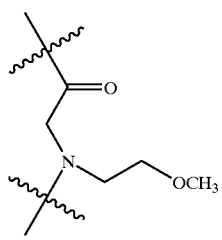
Me = methoxyethyl
| Other Sidechains | |
|---|---|
| 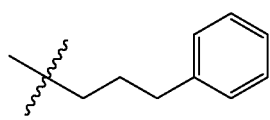 | Phpr = phenylpropyl |
| 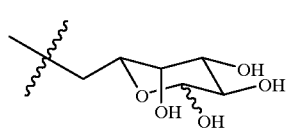 | 6-gal = 6-galactosyl |
| 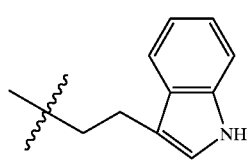 | Trp = 3'-indolylethyl |
| 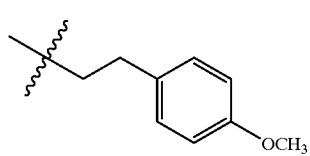 | p-MeOPh = p-methoxyphenylethyl |
| 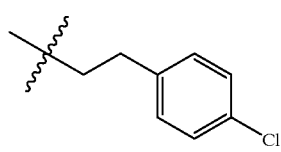 | p-ClPh = p-chlorophenylethyl |
| 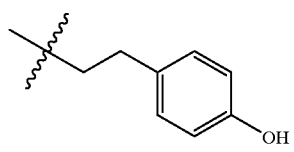 | Tyr = p-hydroxyphenylethyl |
Peptoid-Folic acid conjugates

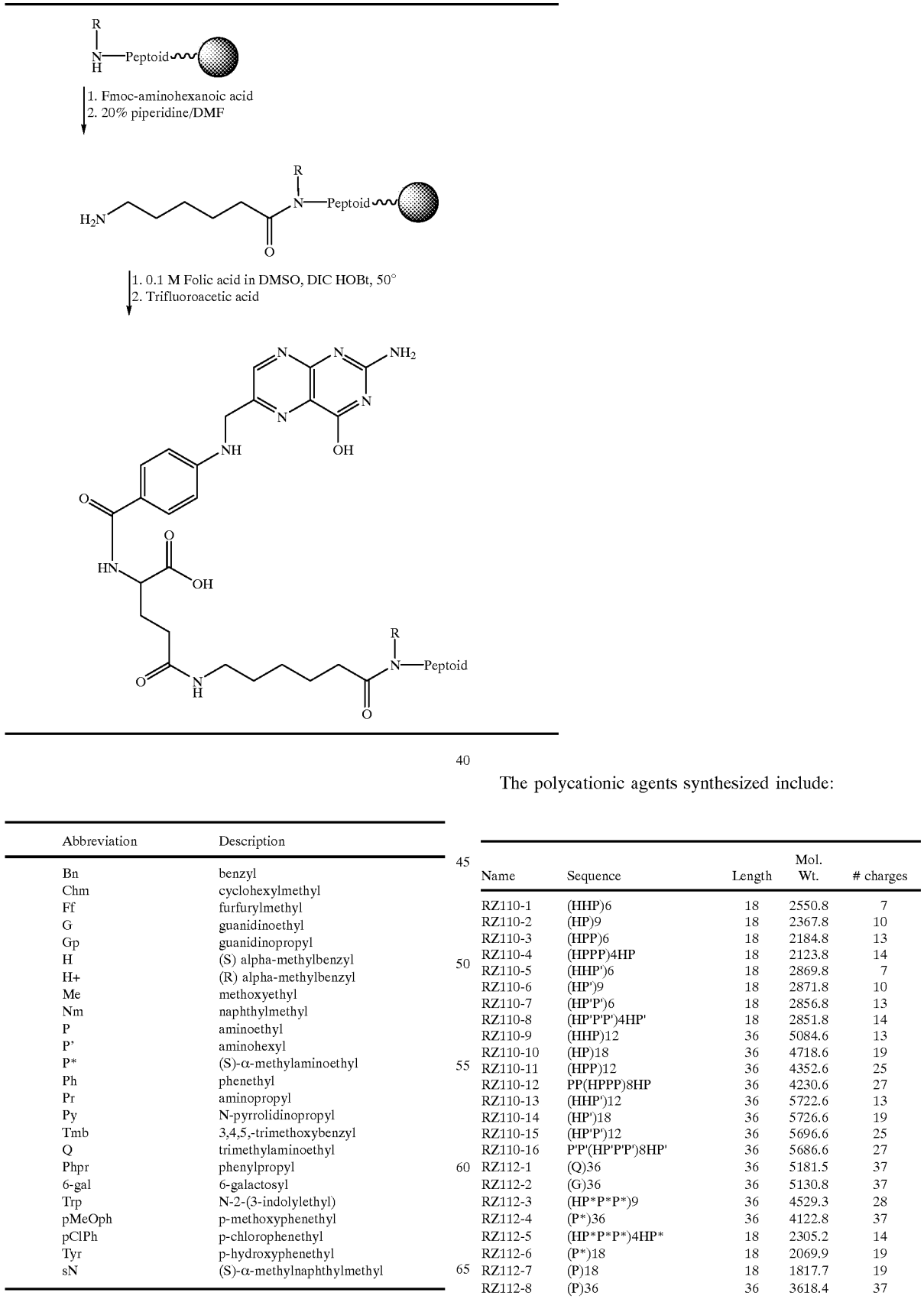

The polycationic agents synthesized include:

| Abbreviation | Description |
|---|---|
| Bn | benzyl |
| Chm | cyclohexylmethyl |
| Ff | furfurylmethyl |
| G | guanidinoethyl |
| Gp | guanidinopropyl |
| H | (S) alpha-methylbenzyl |
| H+ | (R) alpha-methylbenzyl |
| Me | methoxyethyl |
| Nm | naphthylmethyl |
| P | aminoethyl |
| P' | aminohexyl |
| P* | (S)-α-methylaminoethyl |
| Ph | phenethyl |
| Pr | aminopropyl |
| Py | N-pyrrolidinopropyl |
| Tmb | 3,4,5,-trimethoxybenzyl |
| Q | trimethylaminoethyl |
| Phpr | phenylpropyl |
| 6-gal | 6-galactosyl |
| Trp | N-2-(3-indolylethyl) |
| pMeOph | p-methoxyphenethyl |
| pClPh | p-chlorophenethyl |
| Tyr | p-hydroxyphenethyl |
| sN | (S)-α-methylnaphthylmethyl |

| Name | Sequence | Length | Mol. Wt. | # charges |
|---|---|---|---|---|
| RZ110-1 | (HHP)6 | 18 | 2550.8 | 7 |
| RZ110-2 | (HP)9 | 18 | 2367.8 | 10 |
| RZ110-3 | (HPP)6 | 18 | 2184.8 | 13 |
| RZ110-4 | (HPPP)4HP | 18 | 2123.8 | 14 |
| RZ110-5 | (HHP')6 | 18 | 2869.8 | 7 |
| RZ110-6 | (HP')9 | 18 | 2871.8 | 10 |
| RZ110-7 | (HP'P')6 | 18 | 2856.8 | 13 |
| RZ110-8 | (HP'P'P')4HP' | 18 | 2851.8 | 14 |
| RZ110-9 | (HHP)12 | 36 | 5084.6 | 13 |
| RZ110-10 | (HP)18 | 36 | 4718.6 | 19 |
| RZ110-11 | (HPP)12 | 36 | 4352.6 | 25 |
| RZ110-12 | PP(HPPP)8HP | 36 | 4230.6 | 27 |
| RZ110-13 | (HHP')12 | 36 | 5722.6 | 13 |
| RZ110-14 | (HP')18 | 36 | 5726.6 | 19 |
| RZ110-15 | (HP'P')12 | 36 | 5696.6 | 25 |
| RZ110-16 | P'P'(HP'P'P')8HP' | 36 | 5686.6 | 27 |
| RZ112-1 | (Q)36 | 36 | 5181.5 | 37 |
| RZ112-2 | (G)36 | 36 | 5130.8 | 37 |
| RZ112-3 | (HP*P*P*)9 | 36 | 4529.3 | 28 |
| RZ112-4 | (P*)36 | 36 | 4122.8 | 37 |
| RZ112-5 | (HP*P*P*)4HP* | 18 | 2305.2 | 14 |
| RZ112-6 | (P*)18 | 18 | 2069.9 | 19 |
| RZ112-7 | (P)18 | 18 | 1817.7 | 19 |
| RZ112-8 | (P)36 | 36 | 3618.4 | 37 |

-continued

| Name | Sequence | Length | Mol. Wt. | # charges |
|---|---|---|---|---|
| RZ120-1 | (MeMeP)8 | 24 | 2658.4 | 9 |
| RZ120-2 | (BnBnP)8 | 24 | 3170.8 | 9 |
| RZ120-3 | (HHP)8 | 24 | 3394.8 | 9 |
| RZ120-4 | (H+H+P)8 | 24 | 3394.8 | 9 |
| RZ120-5 | (MeMeP)12 | 36 | 3979.2 | 13 |
| RZ120-6 | (BnBnP)12 | 36 | 4747.6 | 13 |
| RZ120-7 | (HHP)12 | 36 | 5083.6 | 13 |
| RZ120-8 | (H+H+P)12 | 36 | 5083.6 | 13 |
| RZ120-9 | (MeMeP)16 | 48 | 5299.9 | 17 |
| RZ120-10 | (BnBnP)16 | 48 | 6324.5 | 17 |
| RZ120-11 | (HHP)16 | 48 | 6772.5 | 17 |
| RZ120-12 | (H+H+P)16 | 48 | 6772.5 | 17 |
| RZ120-13 | (HHP)12 folate | 36 | 5300 | 13 |
| RZ123-1 | (HHPr)12 | 36 | 5252 | 13 |
| RZ123-2 | (HHPr)12 | 36 | 5252 | 13 |
| RZ123-3 | (HHP)12 | 36 | 5084 | 13 |
| RZ123-4 | folate-(HHPr)12 | 36 | 5862 | 13 |
| RZ123-5 | (HHGp)12 | 36 | 5756 | 13 |
| RZ123-6 | (HHG)12 | 36 | 5588 | 13 |
| RZ124-1 | (HHPr)12 | 36 | 5252 | 13 |
| RZ124-2 | (sNsNPr)12 | 36 | 6452 | 13 |
| RZ124-3 | (NmNmPr)12 | 36 | 6116 | 13 |
| RZ124-4 | (PyPyPr) | 36 | 5756 | 13 |
| RZ124-5 | (HHPy)12 | 36 | 6069 | 13 |
| RZ124-6 | (Py)36 | 36 | 6573 | 1 |
| RZ124-7 | folate-(HHPr)12 | 36 | 5862 | 13 |
| RZ127-1 | (PhPhP)12 | 36 | 5085 | 13 |
| RZ127-2 | (ChmChmP)12 | 36 | 4895 | 13 |
| RZ127-3 | (TmbTmbP)12 | 36 | 6912 | 13 |
| RZ127-4 | (FfFfP)12 | 36 | 4508 | 13 |
| RZ136-3 | (PhprPhprP)12 | 36 | 5419 | 13 |
| RZ140-2 | (6-gal)12-(PhPhP)12 | 48 | 7712 | 13 |
| RZ140-3 | (TrpTrpP)12 | 36 | 6020 | 13 |
| RZ144-1 | (PhPPh)12 | 36 | 5083 | 13 |
| RZ144-2 | (PPhPh)12 | 36 | 5083 | 13 |
| RZ144-3 | (pMeoPhpMeoPhP)12 | 36 | 5803 | 13 |
| RZ144-4 | (pClPhpClPhP)12 | 36 | 5910 | 13 |
| RZ144-5 | AMCA-(PhPhP)12 | 36 | 5411 | 12 |
| RZ144-8 | (TyrTyrP)12 | 36 | 5467 | 12 |
| RZ144-12 | (6gal6galP)12 | 36 | 6475 | 13 |
| *RZ145-1 | (PhPhP)12 | 36 | 5085 | 13 |
| RZ147-2 | (PpMeOPhpMeOPh)12 | 36 | 5805 | 13 |

*purified

To summarize the method, Fmoc-Rink amide resin (NovaBiochem, San Diego, Calif., USA) is used as the solid support. This is the same resin that is used for the Fmoc synthesis of peptide C-terminal amides. The polycationic synthesis begins with the deprotection of the Fmoc group on the resin with 20% (v/v) piperidine-dimethylformamide (DMF). The amino resin is then acylated with bromoacetic acid. This is followed by nucleophilic displacement of the bromide with a primary amine to build the NSG monomer. The latter two steps are then continued in an iterative fashion to elaborate the desired oligomer.

All reactions and washings were performed at room temperature unless otherwise noted. Washing of the resin refers to the addition of a wash solvent (usually DMF or dimethylsulfoxide (DMSO)) to the resin, agitating the resin so that a uniform slurry is obtained (typically for about 20 seconds), followed by thorough draining of the solvent from the resin. Solvents were removed by vacuum filtration through the fritted bottom of the reaction vessel until the resin appeared dry (typically about 5 seconds). In all the syntheses, resin slurries were agitated via bubbling argon up through the bottom of the fritted vessel.

A fritted reaction vessel was charged with 100 mg (50 $\mu$mol) of Fmoc-Rink amide resin with a substitution level~0.50 mml/g resin. Two milliliters of DMF was added to the resin and this solution was agitated for 1–2 minutes to swell the resin. The DMF was then drained. The Fmoc group was then removed by adding 2.0 ml of 20% piperidine in DMF to the resin. This was agitated for 1 minute and then drained. Another 2 ml of 20% piperidine in DMF was added to the resin and agitated for 15 minutes and then drained. The resin was then washed with DMF, six times with 2 ml.

The deblocked amine was then acylated by adding 850 $\mu$l of 0.6 M bromoacetic acid in DMF to the resin followed by 200 $\mu$l of 3.2 M N,N'-diisoprooplycarbodiimide (DIC) in DMF. This solution was agitated for 30 minutes at room temperature and then drained. This step was repeated a second time. The resin was then washed with DMF, twice with 2 ml and DMSO, once with 2 ml. This completed one reaction cycle.

The second cycle was initiated by the acylating step with bromoacetic acid and DIC, followed by displacement with the second amine. This acylation/displacement cycle was repeated until the desired oligomer was obtained.

Cleavage of the resin from the polycationic agent is as follows. The dried resin was placed in a glass scintillation vial containing a teflon-coated micro stir bar, and approximately 5 ml of 95% tifluoroacetic acid (TFA) in water was added. The solution was stirred for 20 minutes and then filtered through an 8-ml solid-phase extraction (SPE) column fitted with a 20-$\mu$m polyethylene frit into a 50 ml polypropylene conical centrifuge tube. The resin was washed with 1 ml 95% TFA. The combined filtrates were then lyophilized three times from 1:1 acetonitrile:water. Material was redissolved to a concentration of 5 mM in 5% acetonitrile in water.

Preparation of guanidinoalkyl-containing Polymers:

The guanidinoalkyl sidechains were introduced into the polymers by post-synthesis modification of aminoalkyl sidechains. Thus, polymers were synthesized by the submonomer method as described above except that methoxybenzhydrylamine (MBHA) resin was used instead of the Rink resin. Wherever a guanidinoalky sidechain was desired, a mono-Boc-alkanediamine was incorporated in the displacement step. After elaboration of the polymers, the sidechain Boc groups were removed by treatment with 95% TFA/water for 20 min at room temp. (This does not remove the oligomer from the soliud support). The free amino groups were then guanidinylated by treatment with 1 H-pyrazole-1-carboxamidine (1 M in DMF, 2×1 hr, 40° C.). After washing with DMF and methylene chloride, the oligomer was cleaved from the resin with hydrofluoric acid, and lyophilized.

Preparation of folic acid—polymer conjugates:

Folic acid—polymer conjugates were prepared by adding a linker to the N-terminus of the resin-bound polymer which was then acylated with folic acid. Specifically, after elaboration of the polymer, the N-terminus was acylated with Fmoc-aminohexanoic acid (0.5 M in DMF, 0.5 M hydroxybenzotriazole, 0.5 M diisopropylcarbodiimide (DIC), 1×1 hr, room temp.). After Fmoc group removal (20% piperidine/DMF, 1×20 min, room temp.), the free primary amino group was acylated with folic acid (0.1 M in DMSO, 0.1 M DIC, 1×2 hr, 50° C.). After washing of the resin, the conjugate was cleaved with 95% TFA/water in the usual fashion.

EXAMPLE 2

Condensation of Polynucleotides

Polycationic agents were synthesized and isolated to a final concentration of 5 mM as described in Example 1. Polynucleotides were condensed with RZ110, RZ112, and RZ120 series compounds according to the following procedure.

(1) Dilute all polycationic agents to a final concentration of 3 nanomoles of positive charge per microliter.

(2) Add 1 µg of DNA to 1–2 µl of diluted polycationic agents.

(3) Adjust volume to 10 µl. This mixture can be stored overnight at 4° C.

(4) Add of 5 µl of DNA/polycationic mixture to 2 µl of 5× buffer, which does not contain SDS to maintain the complex. (5× buffer=40% sucrose, 0.25% bromphenol blue and 200 mM Tris Acetate, 4 mM EDTA (PH 7.8).

(5) Adjust volume to 10 µl.

(6) Run sample on a 1% agarose gel utilizing 75 volts for 1.5 hours.

Between 1 to 2 µl, all polycationic agents were judged to retard the migration of DNA into an agarose gel.

EXAMPLE 3

Inhibition of Serum Degradation

The RZ110, RZ112, and RZ120 series compounds were mixed with polynucleotide as described in Example 2. Five microliters of the overnight mixture was added to 5 µl of BalbC mouse serum. The serum was not heat treated but freeze thawed. The serum, polycationic agent, and polynucleotide mixture was incubated typically for 30 minutes at 37° C. The time of incubation varied between 5 and 60 minutes Next, 2 µl of 5× buffer containing 0.5% (wt/v) SDS was added to the incubated mixture. This final solution was loaded onto a 1% agarose gel and electrophoresed at 75 volts for 1.5 hours.

All of the compounds tested, i.e., the entire RZ110, 112, and 120 series, provided significant protection in a direct comparison. The entire RZ112 series and RZ110-3 and RZ110-8 inhibited serum degradation better than poly-L-lysine.

EXAMPLE 4

Peptoid Mediated In Vitro Delivery

DNA comprising a luciferase gene 1 µg/µl, was diluted into endotoxin free water. The plasmid DNA was CMVKm luciferase, which is described in more detail in Example 5.

The transfection protocol for in vitro delivery was as follows:

(A) HT1080 cells were used. These cells are available from American Type Culture Collection, Rockville, Md., USA, Accession No. CCL 121. This is a fibrosarcoma. The growth medium was Dulbecco's Modified Eagle medium (DME) with 10% heat-inactivated fetal calf serum.

(B) Twenty four hours prior to transfection, the cells were placed at 5×10$^4$ per well of a 24-well plate in 1 ml of medium.

1. Feed cells with 500 µl of DME-10% fetal calf serum (FCS ) or 500 µl Opti-MEM®. Opti-Mem® can be purchased from Gibco BRL, Life Technologies, Inc., Gaithersburg, Md., USA.

2. Add 200 µl Opti-MEM® to each tube.

3. Add 3 µl of the desired polycationic agent to the 200 µl of Opti-MEM®.

4. Add 2 µl of 1 µg/µl luciferase DNA, mix.

5. Incubate mixture for 5 minutes at room temperature.

6. Add 100 µl of the polycationic agent/DNA mixture to plate with DME-FCS, 100 µl to cells fed with Opti-MEM®.

7. Incubate cells and polycationic agent/DNA mixture for ~4 hours at 37° C.

8. Change media on all cells to DME-FCS.

9. DME-FCS was used as a positive control.

As a control, a transfectant, LT1, was used from Panvera, Inc., Madison, Wis., USA to transfect cells in serum and cells in Opti-MEM®.

10. Cells were tested for luciferase activity using a Promega Luciferase Assay System from Promega, Madison, Wis., USA., in accordance with the manufacturer's directions.

Results:

| Name | Formula | Luciferase (RLU) |
|---|---|---|
| RZ120-1 | (MeMeP)8 | 0 |
| RZ120-2 | (BnBnP)8 | 0.93 |
| RZ120-3 | (HHP)8 | 1.38 |
| RZ120-4 | (H+H+P)8 | 1.5 |
| RZ120-5 | (MeMeP)12 | 0 |
| RZ120-6 | (BnBnP)12 | 1.64 |
| RZ120-7 | (HHP)12 | 2.64 |
| RZ120-8 | (H+H+P)12 | 2.84 |
| RZ120-9 | (MeMeP)16 | 0 |
| RZ120-10 | (BnBnP)16 | 1.42 |
| RZ120-11 | (HHP)16 | 1.94 |
| RZ120-12 | (H+H+P)16 | 1.32 |
| control | LT1 | 51.96 |
| Experiment #2 | | |
| RZ110-1 | (HHP)6 | 0.0015 |
| RZ110-2 | (HP)9 | 0.0012 |
| RZ110-4 | (HPPP)4HP | 0.0004 |
| RZ110-5 | (HHP')6 | 0.0006 |
| RZ110-6 | (HP')9 | 0.0052 |
| RZ110-7 | (HP'P')6 | 0.0005 |
| RZ110-8 | (HP'P'P')4HP' | 0.0003 |
| RZ110-9 | (HHP)12 | 8.7 |
| RZ110-10 | (HP)18 | 0.0014 |
| RZ110-12 | PP(HPPP)8HP | 0.0459 |
| RZ110-13 | (HHP')12 | 2.5 |
| RZ110-14 | (HP')18 | 2.2 |
| RZ110-15 | (HP'P')12 | 0.064 |
| RZ110-16 | P'P'(HP'P'P')8 | 0.01 |
| control | LT 1 | 88.7 |

EXAMPLE 5

Targeting Ligand

A. Cells, Vector, and Compositions Used.

In a first experiment, murine endothelial cells (Py-4-1) which express high levels of acetylated-LDL receptors. The cells and the LDL receptors were used are described in Dubois et al., 1991, *Exp. Cell Res.* 196:302–313.

A luciferase-containing plasmid (pCMVkmLUC) was used to determine if polynucleotides could be delivered and expressed into endothelial cells when associated with polycationic agents described in Example 1 with acetylated-LDL (Ac-LDL). A description of the identification and isolation of endothelial cells based on their increased uptake of acetylated-low density lipoprotein is in Voyta et al., 1984, *J. Cell Biol.* 99: 2034–2040.

The plasmid used in these experiments pCMVkmLUC, was constructed by inserting the luc+gene from pSP-luc+ (Promega Corporation, Madison, Wis.) into the expression vector pCMVkm2. Briefly, pSP-luc+ was digested with the restriction enzymes Nhe1-EcoRV (Boehringer Mannheim, Indianapolis, Ind.) and a fragment of 1691 bp was isolated by standard methods. This fragment was inserted into pCMVkm2, which had been digested with XbaI and EcoRV using the Rapid Ligation Kit (Boehringer Mannheim, Indianapolis, Ind.). The sequence of pCMVkm2 is depicted in SEQ ID NO:2 and described below. The luc+gene was cloned into pCMVkm2 such that expression is driven by the CMV immediate early enhancer promoter and terminated by the bovine growth hormone polyadenylation signal.

The luciferase expression was compared to levels obtained with the same vector delivered in conjunction with lipofectamine, an agent used commonly to transfect cells in vitro (Hawley-Nelson et al., 1993, *Focus* 15:73). The results are presented in the table below.

B. Method of Transfection:

Briefly, the cells were plated in 24 well dishes, grown to approximately 80% confluence, transfected and assayed 24 hours later for luciferase activity. All transfections were done in serum containing medium. During transfection mixture preparation, pCMVkmLUC was first mixed with RZ 112, and the DNA-cationic polycationic agent complexes were then added to Ac-LDL. Serum containing medium was then added to the mixtures to adjust the volume delivered to each well to 0.5 ml.

Lipofectamine was used as a positive control. No lipoprotein was added to this positive control. Lipofectamine is a 3:1 (w/w) liposome formulation of the polycationic lipid 2,3,-dioleylosy-N-[2(spermine-carboxamido)ethyl]-N,N-dimethyl-1-propanaminiumtrifluoroacetate (DOSPA) and the neutral lipid dioleoyl phosphatidyl-ethanolamine (DOPE) in membrane-filtered water. Lipofectamine can be purchased from Life Technologies, Gaithersburg, Md., USA).

C. Luciferase Assay

Luciferase activity was assayed using the Promega Luciferase Assay System, Madison, Wis.

D. Results

Table 1 shows the results of an experiment where the polycationic agent, RZ-112-2 was compared to lipofectamine to deliver the luciferase gene to cells comprising the acetylated LDL receptor.

TABLE 1

| Group | Ac-LDL (µg) | pCMVkmLUC (µg) | RZ 112-2 (nm) | pg luc/mg protein |
|---|---|---|---|---|
| 1 | 5 | 10 | 2.5 | 61 |
| 2 | — | 10 | — | 0 |
| 3 | — | 10 | 2.5 | 16 |
| 4 | 0.5 | 1 | 0.25 | 16 |
| 5 | — | 1 | 0.25 | 17 |
| 6 | 0.5 | 10 | 2.5 | 631 |
| 7 | 0.5 | 10 | 5 | 1996 |
| LIPOFECTAMINE CONTROL | | | | |
| 8 | — | 10 | — | 10786 |

*each number represents the mean of three wells.

EXAMPLE 6

Comparison of Cells with and without Acetylated LDL Receptors

A. Cells with Acetylated LDL Receptors

For this experiment, K1735 mouse, epithelial melanoma cells were used. These cells express low or non-existent levels of Ac-LDL receptors. A description of the cells is in *J. Natl. Cancer Inst.* 69(4): (1982).

B. Methods

Briefly, the cells were plated in 24 well dishes at 10,000 cells per well in DME with 10% FCS supplemented with 2 mM L-glutamine. The Py-4-1 cells were cultured in 10% $CO_2$ at 37° C. The K1735 cells were cultured in 5% $CO_2$ at 37° C. The cells were grown to approximately 50% confluence, transfected and assayed 24 hours later for luciferase activity. All transfections were done in serum containing medium.

During transfection mixture preparation, pCMVkmLUC was first mixed with RZ 112-2, and the DNA-polycationic agent complexes were then added to Ac-LDL. Serum containing medium was then added to the mixtures to adjust the volume delivered to each well to 0.5 ml.

C. Results

TABLE 2

| | | | | Luciferase Activity | |
|---|---|---|---|---|---|
| | Ac-LDL | pCMVkmLUC | RZ 112-2 | pg luc/mg protein* | |
| Group | (µg) | (µg) | (nm) | Py-4-1 | K1735 |
| 1 | 0.5 | 1 | 1 | 1301 | 24 |
| 2 | 0.5 | 1 | 5 | 2181 | 0 |
| 3 | 0.5 | 1 | 10 | 373 | 0 |
| 4 | 0.5 | 10 | 5 | 840 | 0 |
| 5 | — | 1 | 5 | 327 | 0 |
| 6 | — | 1 | 5 | 945 | ND |
| 10 | 5 | 1 | 5 | 298 | ND |
| LIPOFECTAMINE CONTROL | | | | | |
| 7 | — | 1 | — | 23 | 0 |
| 8 | — | 10 | — | 2878 | 960 |

*each number represents the mean of three wells.

EXAMPLE 7

Injection of Polynucleotides Encoding Erythropoietin

A. Polynucleotides

CMVkm2 is the standard vector used in these studies. CMVkm2 is a vector optimized for expression in mammalian cells. The gene of interest is cloned into a polylinker which is inserted 3' of a human CMV expression cassette. This cassette contains the human CMV immediate early promoter/enhancer followed by intron A of the human CMV immediate early region (Chapman et al., 1991, *Nucl. Acids Res.* 19:3937–3986). Transcription is terminated by a polyadenylation site from the bovine growth hormone gene, which has been cloned immediately 3' of the polylinker. See SEQ ID NO:2 for the CMVkm2 vector.

The CMV-km-cmEPO vector was constructed from CMVkm2 as follows. The cynomolgus monkey EPO cDNA was acquired from the ATCC (Accession No. 67545, Rockville, Md.). This plasmid was cut with AvrII and BglII and inserted into the XbaI and BamHI sites of the CMVkm2 vector. The inserted sequence contains the entire coding region of cmEPO (Genbank accession M18189). See SEQ ID NO:3.

B. Mice

Immunodeficient severe combined immunodeficiency (SCID) mice were obtained from Charles River Labs, Wilmington, Mass., USA.

Intramuscular injections were performed as follows: mice were anaesthetized with 50 × of a solution which contained 80 mg/ml ketamine and 4 mg/ml of xylazine. The area surrounding the anterior tibialis muscle was shaved. Fifty µl of DNA, at a concentration of 2.7 ug/µl in 0.9% saline solution was injected into the anterior tibialis muscle of both legs using a 28 gauge needle. Twenty-four hours after the first injection, a second injection was performed using the identical protocol. Blood was taken from the orbital sinus to determine hematocrits on a weekly basis.

C. Result

The hematocrit readings on 6 mice which were injected with plasmid, CMVkm-cmEpo (which expresses the cynomolgus monkeys EPO cDNA), are shown in Table 3 below. The row marked control shows the average reading for three uninjected mice. The raw data for the three control mice is shown in the lower part of Table 3. Mouse 2 in the injected group died between 4 and 5 weeks post-injection.

described above in the Example 7 and the area surrounding the anterior tibialis muscle was shaved.

Fifty microliters of DNA at a concentration of 3.3. $\mu g/\mu l$ in 0.9% saline solution was injected into the anterior tibialis muscle of both legs using a 28 gauge needle.

Seventy-two hours after the first injection, a second injection was performed using the identical protocol.

Group 1 ob/ob mice were injected with a plasmid (CMVkM leptin-wt) which encodes the wild-type mouse leptin protein.

TABLE 3

Hematocrit Levels (%)

| Mouse | Week 0 | week 1 | week 2 | week 3 | week 4 | week 5 | week 6 | week 7 | week 8 | week 9 | week 10 |
|---|---|---|---|---|---|---|---|---|---|---|---|
| mouse 1 | 50 | 63 | 66.5 | 57.5 | 63 | 63.5 | 56.5 | 62.5 | 54 | 53.5 | 54.5 |
| mouse 2 | 50 | 64 | 64 | 56.5 | 55.5 | | | | | | |
| mouse 3 | 50 | 60 | 61.5 | 63 | 61 | 56 | 49.5 | 53 | 53.5 | 54.5 | 57 |
| mouse 4 | 50 | 62 | 68.5 | 71.5 | 67.5 | 60 | 62.5 | 59.5 | 57.5 | 53.5 | 55.5 |
| mouse 5 | 50 | 62 | 62.5 | 56 | 61 | 53.5 | 58 | 52.5 | 54 | 52.5 | 48.5 |
| mouse 6 | 50 | 66 | 63.5 | 62.5 | 60 | 58 | 58 | 53.5 | 55.5 | 52.5 | 52.5 |
| Control | 50 | 51.5 | 48 | 47.5 | 53 | 49.5 | 49.5 | 50.5 | 51.5 | 51 | 49 |

| control | week 0 | control wk 1 | control wk 2 | control wk 3 | control week 4 | control week 5 | control week 6 | control week 7 | control week 8 | control week 9 | control week 10 |
|---|---|---|---|---|---|---|---|---|---|---|---|
| mouse 1 | 50 | 52 | 48 | 46.5 | 52.5 | 48 | 49.5 | 52 | 51.5 | 50.5 | 46.5 |
| mouse 2 | 50 | 51 | 47 | 47 | 55 | 51 | 50.5 | 50 | 52 | 49 | 51.5 |
| mouse 3 | 50 | 52 | 49 | 48.5 | 52 | 49.5 | 48.5 | 48.5 | 51 | 52.5 | 50 |

EXAMPLE 8

Injection of Polynucleotides Encoding Leptin

A. Polynucleotides

Figure 4:
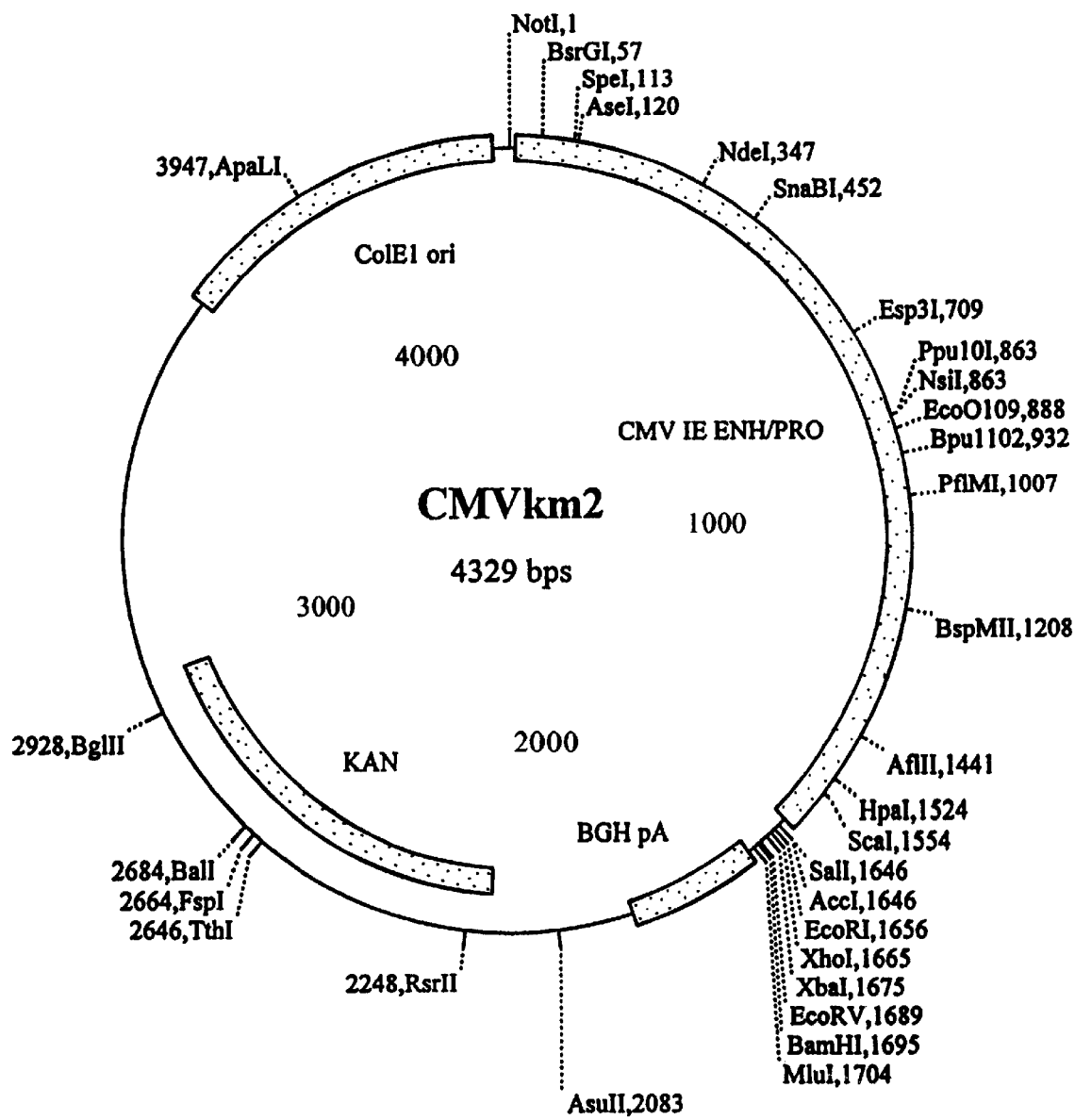
FIG. 4 is a plasmid map of vector CMVkm2.
Figure 5:
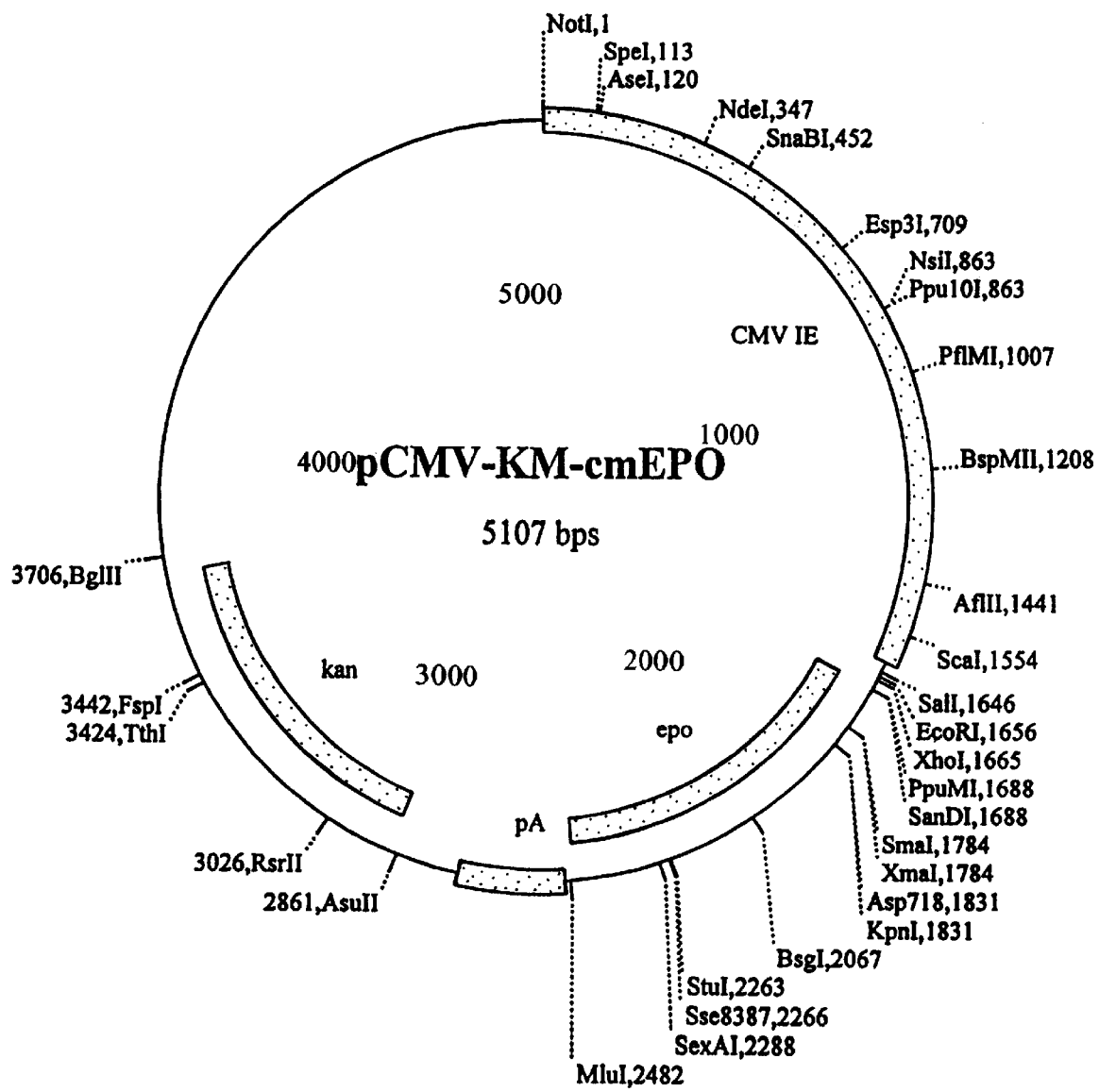
FIG. 5 is a plasmid map of vector pCMV-KM-cmEPO.
Figure 6:
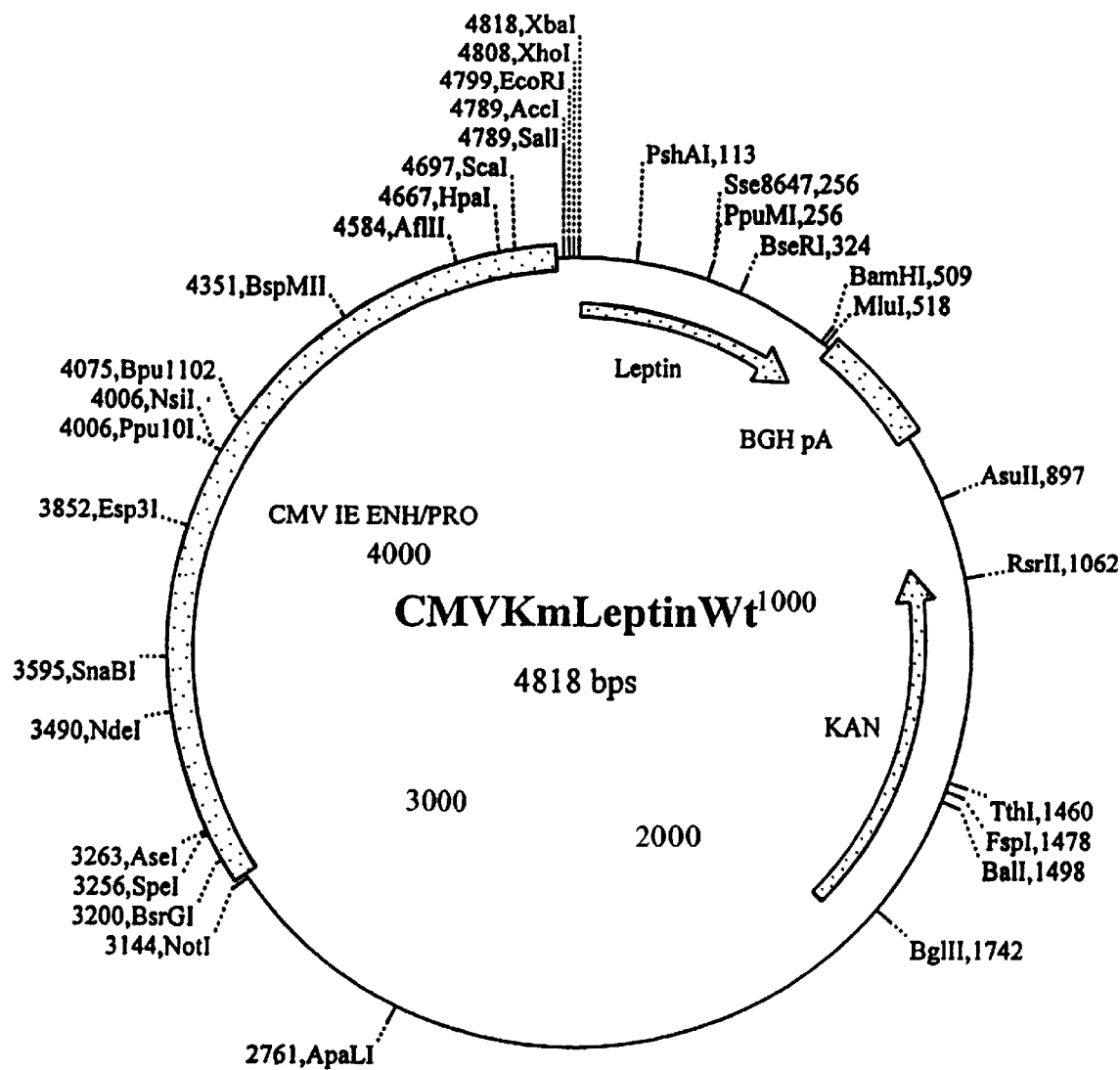
FIG. 6 is a plasmid map of vector CMVKmLeptin Wt.

The CMV-km2 vector, described above, was used for these experiments. Either the wild-type or HA version of the leptin coding region was inserted into the vector. The map of the plasmid is depicted in FIG. 4 and the sequence of the vector with the wild type leptin is shown in SEQ ID NO:4.

B. Mice

Ob/ob mice were obtained from Jackson Labs, Bar Harbor, Me., USA. The first of the recessive obesity mutations, the obese mutation (ob) was identified and described in 1950 by Ingall et al., 1950, *J. Hered.* 41:317–318. Subsequently, 5 single-gene mutations in mice have been observed to produce an obese phenotype, as described in Friedman et al., 1990, *Cell* 69:217–220. (More recently, the mouse obese gene and its human homologue have been cloned, as described in Zhang et al., 1994, *Nature* 372:425).

C. Method

Intramuscular injections were performed as follows: mice were anaesthetized with the same ketamine solution Group 2 ob/ob mice were injected with a plasmid (CMVkm-leptinHA) which encodes a form of mouse leptin which is modified with the epitope which is recognized by the antibody 12CA5. The amino acid sequence of the epitope is SYPYDVPDYASLGGPS (Wilson et al., 1984, *Cell* 37: 767–778).

Group 3 ob/ob mice were injected with a solution of 0.9% saline.

The mice were weighed each day (see Table 4) and the proportional weight gain for each mouse during the first eight days was calculated. The results are shown in Table 5. For any given day, the weight was subtracted from the weight of the individual mouse on day 0, and the difference was divided by the weight on day 0. The proportional weight change data from day 8 was analyzed using an unpaired t-test. When compared with group 3 control mice the p value from group 2 mice was 0.004. When compared with group 3 control mice, the p value for group 1 mice is 0.0038.

Note: the mice were not weighed on day 1 and day 2, the values for these days were extrapolated from day 3.

TABLE 4

Weight of Mice in Grams

| | day 0 | day 3 | day 4 | day 5 | day 6 | day 7 | day 8 | day 9 | day 10 | day 11 | day 12 |
|---|---|---|---|---|---|---|---|---|---|---|---|
| group 1 | | | | | | | | | | | |
| mouse 1 | 47 | 49 | 49 | 51 | 51 | 51 | 51 | 52 | 52 | 53 | 53 |
| mouse 2 | 48 | 49 | 49 | 51 | 51 | 51 | 51 | 52 | 53 | 52 | 53 |
| mouse 3 | 46 | 48 | 48 | 49 | 49 | 49 | 49 | 50 | 51 | 50 | 51 |
| mouse 4 | 47 | 48 | 48 | 49 | 49 | 49 | 50 | 50 | 50 | 50 | 51 |
| mouse 5 | 49 | 50 | 50 | 51 | 51 | 51 | 52 | 52 | 52 | 52 | 52 |

TABLE 4-continued

Weight of Mice in Grams

|  | day 0 | day 3 | day 4 | day 5 | day 6 | day 7 | day 8 | day 9 | day 10 | day 11 | day 12 |
|---|---|---|---|---|---|---|---|---|---|---|---|
| group 2 | | | | | | | | | | | |
| mouse 1 | 49 | 50 | 50 | 52 | 52 | 52 | 52 | 53 | 54 | 54 | 56 |
| mouse 1 | 43 | 45 | 44 | 45 | 45 | 44 | 45 | 45 | 45 | 46 | 47 |
| mouse 3 | 48 | 49 | 49 | 50 | 50 | 50 | 51 | 52 | 52 | 52 | 52 |
| mouse 4 | 49 | 50 | 50 | 52 | 51 | 51 | 52 | 52 | 52 | 52 | 53 |
| mouse 5 | 46 | 48 | 49 | 49 | 49 | 50 | 50 | 51 | 51 | 51 | 51 |
| group 3 | | | | | | | | | | | |
| mouse 1 | 40 | 42 | 42 | 43 | 43 | 45 | 45 | 45 | 45 | 45 | 46 |
| mouse 2 | 48 | 49 | 50 | 50 | 51 | 52 | 52 | 52 | 52 | 53 | 53 |
| mouse 3 | 48 | 50 | 50 | 52 | 52 | 53 | 53 | 55 | 55 | 55 | 55 |
| mouse 4 | 49 | 52 | 52 | 53 | 53 | 54 | 55 | 54 | 54 | 54 | 55 |
| mouse 5 | 43 | 45 | 46 | 47 | 48 | 49 | 50 | 49 | 49 | 48 | 49 |

TABLE 5

Proportional Change in Weight from Day 0 of Mice Injected with cDNA for Leptin (gp1), Leptin-HA (gp2) or Saline

|  | day 0 | day 1 | day 2 | day 3 | day 4 | day 5 | day 6 | day 7 | day 8 |
|---|---|---|---|---|---|---|---|---|---|
| Group 1 Mice Below Injected with CMVkM-Leptin-wt | | | | | | | | | |
| mouse 1 | 0 | 0.009 | 0.018 | 0.028 | 0.028 | 0.059 | 0.059 | 0.059 | 0.066 |
| mouse 2 | 0 | 0.013 | 0.026 | 0.039 | 0.039 | 0.085 | 0.085 | 0.085 | 0.085 |
| mouse 3 | 0 | 0.006 | 0.012 | 0.018 | 0.018 | 0.062 | 0.062 | 0.062 | 0.062 |
| mouse 4 | 0 | 0.014 | 0.028 | 0.042 | 0.042 | 0.065 | 0.065 | 0.065 | 0.065 |
| mouse 5 | 0 | 0.007 | 0.014 | 0.021 | 0.021 | 0.042 | 0.042 | 0.042 | 0.06 |
|  | 0 | 0.007 | 0.014 | 0.021 | 0.021 | 0.041 | 0.041 | 0.041 | 0.061 |
| Group 2 Mice Below Injected with CMVkM-LeptinHA | | | | | | | | | |
| mouse 1 | 0 | 0.006 | 0.013 | 0.02 | 0.02 | 0.06 | 0.06 | 0.06 | 0.06 |
| mouse 2 | 0 | 0.013 | 0.031 | 0.046 | 0.023 | 0.046 | 0.046 | 0.046 | 0.046 |
| mouse 3 | 0 | 0.007 | 0.014 | 0.021 | 0.021 | 0.04 | 0.04 | 0.04 | 0.062 |
| mouse 4 | 0 | 0.006 | 0.012 | 0.02 | 0.02 | 0.06 | 0.04 | 0.04 | 0.06 |
| mouse 5 | 0 | 0.014 | 0.028 | 0.043 | 0.065 | 0.065 | 0.065 | 0.08 | 0.08 |
| Group 3 Mice Below Injected with Saline | | | | | | | | | |
| mouse 1 | 0 | 0.016 | 0.032 | 0.05 | 0.05 | 0.06 | 0.06 | 0.125 | 0.125 |
| mouse 2 | 0 | 0.07 | 0.014 | 0.021 | 0.04 | 0.04 | 0.06 | 0.08 | 0.08 |
| mouse 3 | 0 | 0.013 | 0.026 | 0.04 | 0.04 | 0.08 | 0.08 | 0.1 | 0.1 |
| mouse 4 | 0 | 0.02 | 0.04 | 0.06 | 0.06 | 0.08 | 0.08 | 0.1 | 0.12 |
| mouse 5 | 0 | 0.015 | 0.03 | 0.045 | 0.069 | 0.09 | 0.12 | 0.14 | 0.14 |
| Average Proportional change in Weight for Each Group | | | | | | | | | |
| group 1 | 0 | 0.009 | 0.018 | 0.028 | 0.028 | 0.059 | 0.059 | 0.059 | 0.066 |
| group 2 | 0 | 0.009 | 0.018 | 0.028 | 0.029 | 0.054 | 0.05 | 0.053 | 0.061 |
| group 3 | 0 | 0.014 | 0.028 | 0.042 | 0.051 | 0.07 | 0.08 | 0.109 | 0.113 |

EXAMPLE 9

Peptoid Mediated In Vitro Delivery in COS, HT1080, and 293 Cell Lines

COS cells (available from the American Type Culture Collection, Rockville, Md., under Accession No. CRL 1651 and HT1080 cells (available from the American Type Culture Collection, Rockville, Md., under Accession No. CCL 121) were cultured and transfected with pCMVkmLUC and various polycationic agents of the present invention (described in Example 1) according to the transfection protocol described in Example 4. Luciferase activity was assayed according to the method described in Example 4. Total cell protein was measured using a Pierce BCA kit according to manufacturer's directions.

Figure 7A:
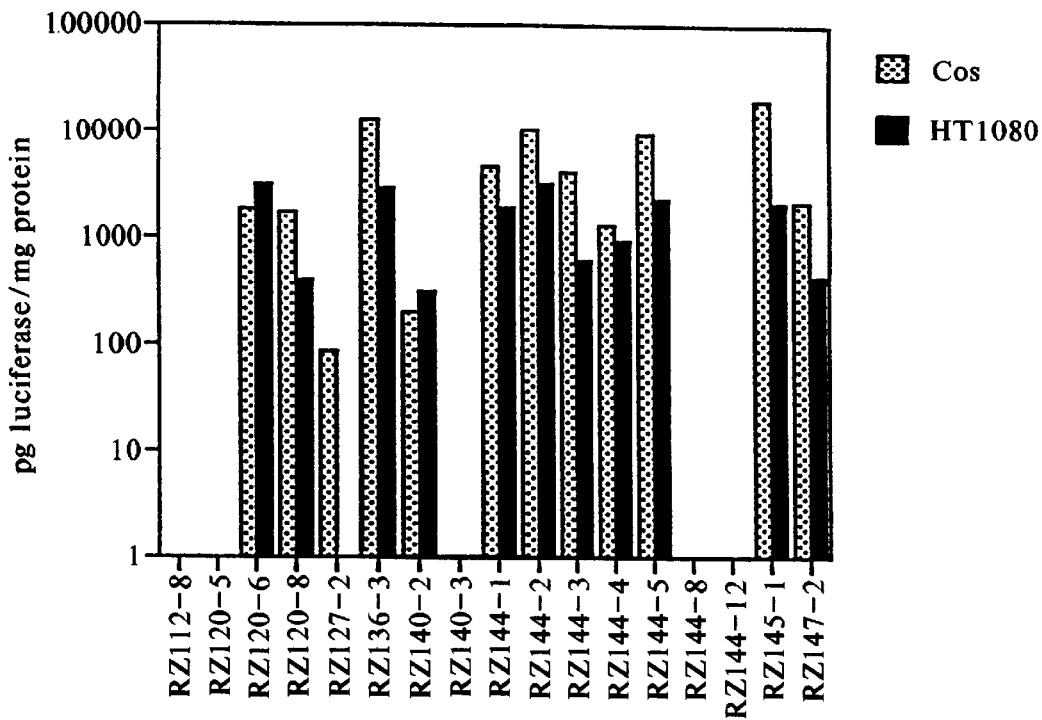
FIG. 7A illustrates transfection efficiencies for a diverse set of polycationic agents. The polycatonic agents were formulated with DNA at a 2:1, + to − charge ratio and added to either HT1080 (solid bar) or COS (stippled bar) in the presence of 10% serum. Luciferase activity was analyzed 48 hours post-transfection. Total cell protein was measured using a Pierce BCA assay and luciferase activity was normalized against total cell protein.

The results, shown in FIG. 7A, indicate that the ability of the polycationic agents to mediate transfection is not dependent on cell line type. Polycationic agents having a repeating trimer motif of neutral and cationic sidechains were particularly effective at mediating transfection.

Transfection efficiencies for a homologous series of cationic peptoids were evaluated. Specifically, cationic peptoids RZ-110-1 (18-mer), RZ-120-3 (24 mer), RZ120-7 (36 mer), and RZ120-11 (48 mer), which have the same repeating (HHP) motif were evaluated for their ability to transfect COS and HT1080 cells. These polycationic agents were complexed with pCMVkmLUC at a 2:1, + to − charge ratio. The concentration of negative charges on DNA was calculated using 3.03 nmol of phosphate per 1 μg of DNA, on the basis of the average molecular weight of 330 for each nucleotide. The formula weight of the polycationic agent was calculated as a semi-trifluoroacetate salt (50% of amino groups form salt with TFA), and the concentration of the polycationic agent was determined on the basis of the weight of the lyophilized peptoid. Amino groups were formally considered to be fully protonated to obtain the number of positive charges on the polycationic agent interest when calculating the + to − charge.

Figure 7B:
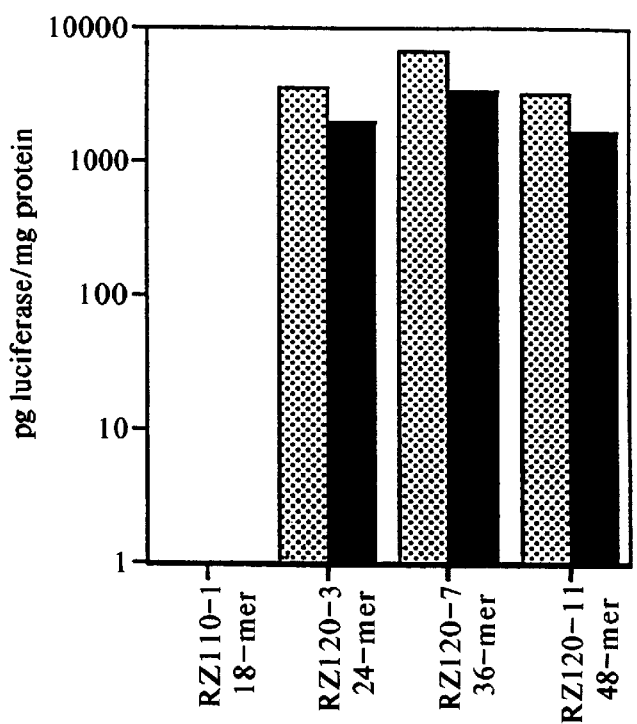
FIG. 7B illustrates the effect of oligomer length on transfection efficiency for polycationic agents having different numbers of the same repeating trimer motif. For both A and B each data point represents the average of 2 experiments.

As shown in FIG. 7B, transfection efficiencies for this particular series of cationic peptoids were largely independent of oligomer length for peptoids having 24 or more monomeric units.

Transfection efficiencies using polycationic agent RZ145-1 and commercially available cationic lipids, DMRIE-C™, Lipofectin® and lipofectamine were evaluated. In these experiments RZ145-1 was complexed with pCMVkmLUC at a 2:1, + to − charge ratio. Transfection with DMRIE-C™ Lipofectin®, lipofectamine was conducted according to manufacturer's directions. The cationic lipids were also employed at a 2:1, + to − charge ratio. 293 human embryonic kidney cells (Microbix, Toronto, Ontario, Canada), HT1080 cells, and NIH-3T3 cells (available from the American Type Culture Collection, Rockville, Md., Accession No. CRL 1658) were transfected, cultured either in the presence or absence of 10% serum, then assayed for luciferase production using the same protocol as described in Example 4. Luciferase was measured, as described in Example 4, 48 hours after initial transfection. Total cell protein was measured using a Pierce BCA kit according to manufacturer's directions.

Figure 8A:
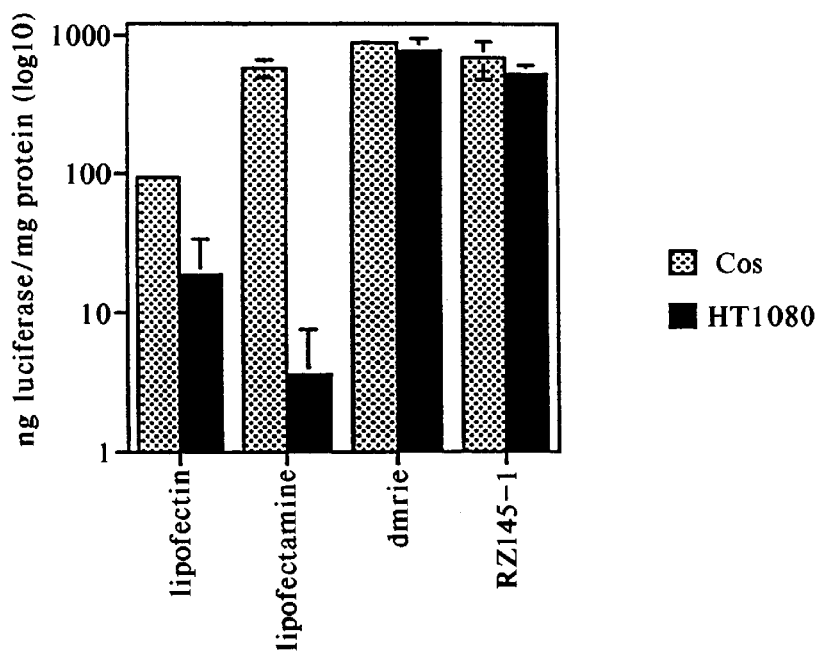
FIGS. 8(A–C) shows RZ145-1 peptoid-mediated transfection and transfection mediated by commercially available cationic liposome preparations. RZ145-1 or the indicated lipid was formulated and added to cells in the presence (solid bar) or absence (stippled bar) of 10% serum. Luciferase and total cell protein activity were measured 48 hours after initial transfection. Cells lines are (FIG. 8A) 293 human embryonic kidney cells, (FIG. 8B) HT1080 human fibrosarcoma cells, and (FIG. 8C) NIH03T3 mouse fibroblast cells. Each data point represents the average+strandard error of the mean of three transfections.
Figure 8B:
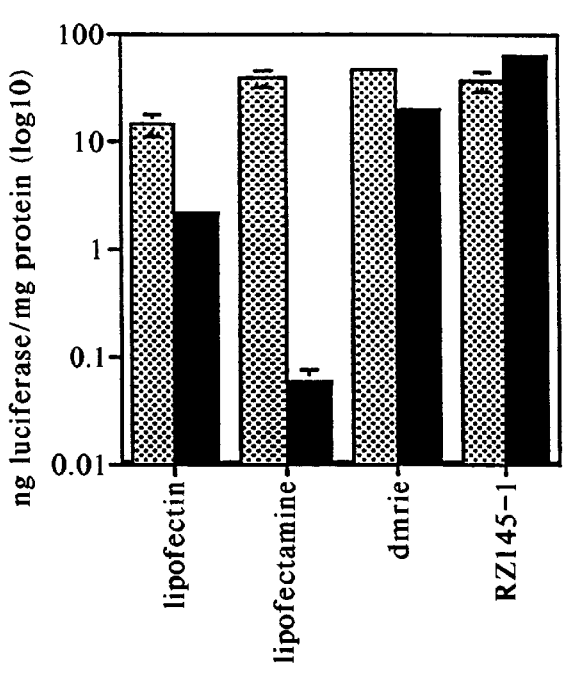
Figure 8C:
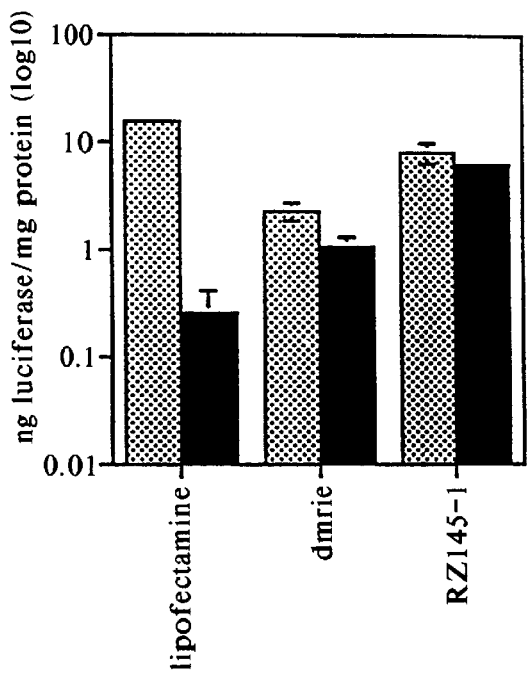

The results, shown in FIG. 8, indicate that, in contrast to Lipofectin® and lipofectamine, which were respectively 10- and 100-fold less efficient in the presence of serum, gene transfer mediated by polycationic agent RZ145-1 was insensitive to the presence of serum.

Figure 9A:
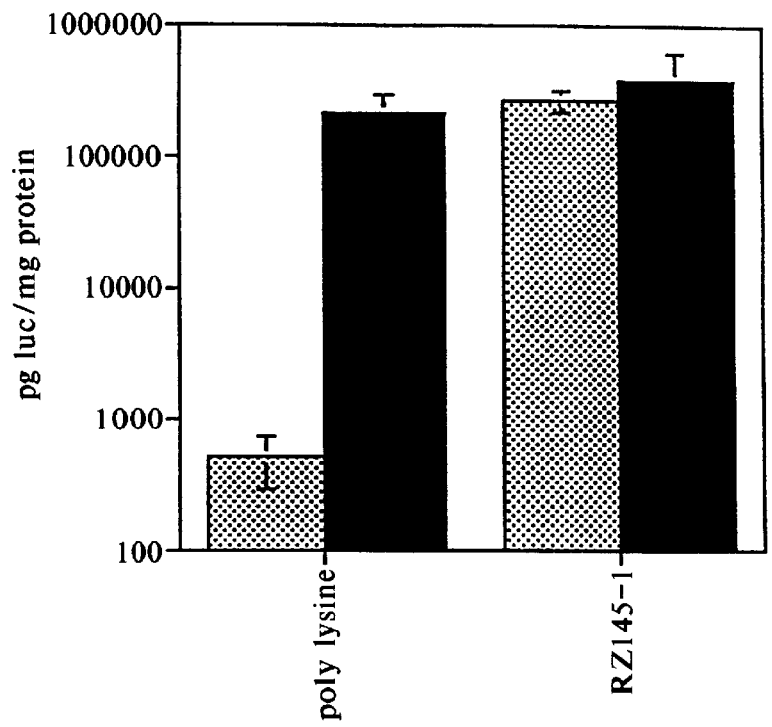
FIGS. 9A and 9B illustrate the effect of chloroquine on transfection with RZ145-1 in (A) 293 cells and (B) HT1080 cells. The cells were transfected in the presence (black bar) or absence (stippled bar) of 100 uM chloroquine. Cells were lysed 48 hours post transfection and luciferase activity and total protein content were measured.
Figure 9B:
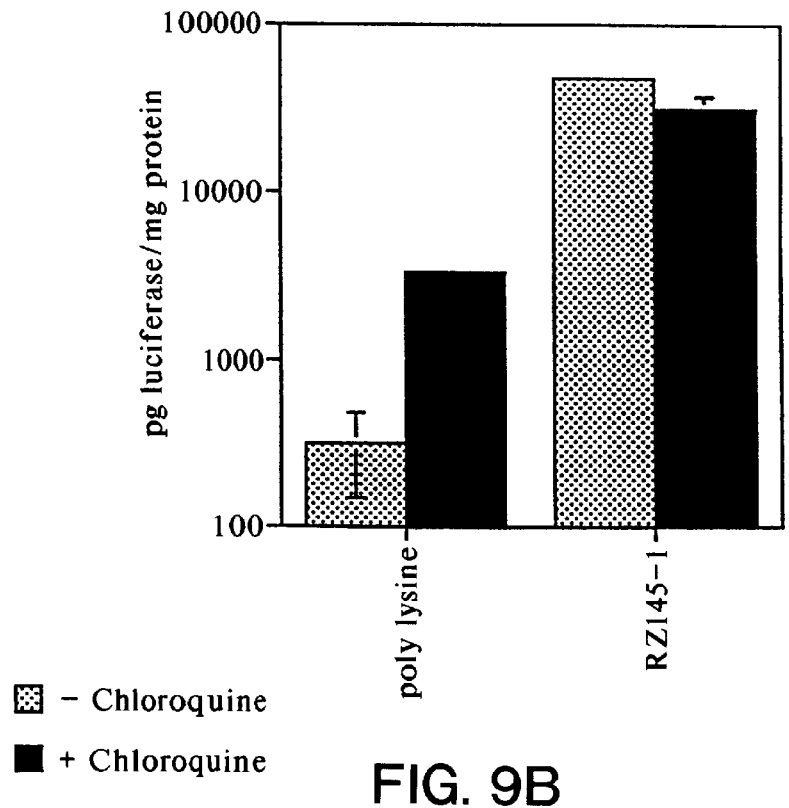

Transfection mediated by polycationic polymers, such as polylysine and histones, is greatly enhanced by addition of chloroquine to the transfection media. To determine whether chloroquine affected transfection mediated by polycationic agents of the present invention, HT1080 and 293 cells were transfected using RZ145-1 in the presence and absence of chloroquine. As a control, the same cell lines were transfected with polylysine both in the presence and absence of chloroquine. The results, shown in FIG. 9, indicate that the polycationic agent RZ145-1 was equally effective at mediating transfection both with and without chloroquine. In contrast, polylysine-mediated transfection in the absence of chloroquine was 100-fold lower than polylysine mediated transfection in the presence of chloroquine. In addition, the results indicate that cationic peptoid mediated transfection is more efficient than polylysine mediated transfection.

EXAMPLE 10

Preparation of a Stable Formulation of DNA/ Polycationic Agent Complex

A. DNA/Polycatinic Agent Complex Formation (2:1, + to – Change Ratio)

All operations were carried out at ambient temperature. DGPW (diagnosis grade purified water) was used to prepare the stock solutions. Both the polycationic agent and DNA samples had low salt concentrations (i.e., <1 mM) to avoid precipitation.

(1) Batch Method

Complexes of polycationic agent RZ145-1 and pCMVkmLUC, as follows, for up to 250 $\mu$g DNA. DNA (i.e., pCMVkmLUC) was diluted with 30% (v/v) ethanol in water to a concentration of 50 $\mu$g/ml corresponding to 151 $\mu$M of negative charge. RZ145-1 was diluted to 23.2 $\mu$M in 30% ethanol in water. To 1 part of the polycationic agent solution was added 1 part of DNA solution as quickly as possible with gentle agitation. The DNA solution was added to the solution of polycationic agent (rather than vice-versa) to avoid precipitation. Slow addition of the two solutions was avoided to avoid precipitation and the formation of large complexes.

(2) Continuous Method

For more than 250 $\mu$g of DNA, a continuous method for preparing concentrated formulations of polycationic agent/ DNA complex is preferred. The DNA and peptoid solutions were prepared as above and placed into separate bottles. Each bottle was connected to one port of a mixing tee. The bottles were simultaneously pressurized with 2 to 3 psi to deliver the two streams to the mixing tee at the same flow rate (e.g., 20 ml/min or higher).

B. Concentration Step

Two milliliters of the DNA-polycationic agent complex from part A was placed in a Centricon®-100 (Amico Inc. Beverly, Mass.), and centrifuged at 1000×g for 30 minutes or until the volume of the retentate containing polycationic agentDNA complex was approximately 50 $\mu$l. The filtrate was removed from the bottom receiver. The retentate was diluted with 2 ml of 5% glucose, and concentrated to 50 $\mu$l again. This operation was repeated again to produce a concentrated complex solution containing 1 mg/ml DNA in 5% glucose. This concentration step can be conducted at either 4° C. or at ambient temperature. The ethanol content of the final concentrated solution was less than 0.1%. No precipitation was observed in the concentrated solution.

What is claimed:

1. A polycationic agent having the following formula:

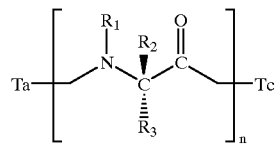

wherein
n is an integer from 10 to 100 resulting in a repeating trimer wherein two $R_1$ groups of each trimer are neutral and one $R_1$ group of each trimer is cationic;
$R_2$ and $R_3$ are hydrogen for each monomer:

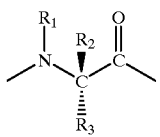

$T_a$ and $T_c$ are terminating groups;
said cationic $R_1$ groups are selected from the group consisting of ammoniumalkyl, aminoalkyl, guanidinoalkyl, amidinoalkyl, aminocyclohexyl, piperidyl, guanidinobenzyl, guanidino-α-methylbenzyl, amidinobenzyl, amidino-α-methylbenzyl, an aliphatic hydrazide, an aromatic hydrazide; pyridylmethyl, wherein the pyridyl ring is optionally further substituted with a group selected from methyl, methoxy, fluoro, chloro, bromo, and nitro; and aminobenzyl, wherein the benzyl ring is optionally further substituted with a group selected from methyl, methoxy, fluoro, chloro, bromo, and nitro;
wherein "ammonium" is trimethylammonium, triethylammonium, methyldiethylammonium, or ethyldimethylammonium, and "alkyl" is —CH(R)—$(CH_2)_m$—, where R is H or Me, and m is 1–6;
and said neutral $R_1$ groups are selected from the group consisting of a neutral moiety comprising an aromatic ring and having a molecular weight of 250 daltons or less, cyclohexyl methyl, 2-methoxyethyl, and 6-galactosyl;
wherein said polycationic agent comprises at least 25% positively charged monomers, excluding the terminating groups, and
wherein said polycationic agent exhibits a net positive electrical charge at a physiological pH.

2. The polycationic agent according to claim 1, wherein said cationic $R_1$ group is aminoethyl.

3. The polycationic agent according to claim 1, wherein said neutral $R_1$ groups are selected from the group consisting of phenethyl, benzyl, phenylpropyl, (R) alpha-methylbenzyl, (S) alpha-methylbenzyl, methoxyphenethyl, and chlorophenethyl.

4. The polycationic agent of claim 3, wherein $T_a$ and $T_c$ are terminating groups selected from the group consisting of —NH$_2$, —OH, —SH, —COOH, polypeptide, lipid, lipoprotein, vitamin, hormone, polyalkylene glycol, and saccharide.

5. The polycationic agent of claim 1 wherein n is 36.
6. The polycationic agent of claim 1, wherein n is 24.
7. The polycationic agent of claim 1, wherein n is 18.
8. The polycationic agent of claim 1, wherein n is 12.
9. The polycationic agent of claim 1, wherein said neutral $R_1$ groups are selected from the group consisting of phenethyl, p-methoxyphenyl ethyl, 4-sulfamidophenyl ethyl, phenyl propyl, halophenyl alkyl, hydroxyphenyl alkyl, benzyl, (R)-α-methylbenzyl, (S)-α-methylbenzyl, 3,4,5-trimethoxybenzyl, naphthyl methyl, (S)-α-methyl naphthyl methyl, furfuryl methyl, N-pyrrolidono propyl, indolyl alkyl, alkylphenyl, alkoxyphenyl, cyclohexyl methyl, 2-methoxyethyl, and 6-galactosyl.

* * * * *

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 9600 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:1:

```
GCGGCCGCGG AATTCTCATG TTTGACAGCT TATCATCGAT AAGCTGATCC TCACAGGCCG      60

CACCCAGCTT TTCTTCCGTT GCCCCAGTAG CATCTCTGTC TGGTGACCTT GAAGAGGAAG     120

AGGAGGGGTC CCGAGAATCC CCATCCCTAC CGTCCAGCAA AAAGGGGGAC GAGGAATTTG     180

AGGCCTGGCT TGAGGCTCAG GACGCAAATC TTGAGGATGT TCAGCGGGAG TTTTCCGGGC     240

TGCGAGTAAT TGGTGATGAG GACGAGGATG GTTCGGAGGA TGGGGAATTT TCAGACCTGG     300

ATCTGTCTGA CAGCGACCAT GAAGGGGATG AGGGTGGGGG GGCTGTTGGA GGGGGCAGGA     360

GTCTGCACTC CCTGTATTCA CTGAGCGTCG TCTAATAAAG ATGTCTATTG ATCTCTTTTA     420

GTGTGAATCA TGTCTGACGA GGGGCCAGGT ACAGGACCTG GAAATGGCCT AGGAGAGAAG     480

GGAGACACAT CTGGACCAGA AGGCTCCGGC GGCAGTGGAC CTCAAAGAAG AGGGGGTGAT     540
```

```
AACCATGGAC GAGGACGGGG AAGAGGACGA GGACGAGGAG GCGGAAGACC AGGAGCCCCG      600

GGCGGCTCAG GATCAGGGCC AAGACATAGA GATGGTGTCC GGAGACCCCA AAAACGTCCA      660

AGTTGCATTG GCTGCAAAGG GACCCACGGT GGAACAGGAG CAGGAGCAGG AGCGGGAGGG      720

GCAGGAGCAG GAGGGCAGG AGCAGGAGGA GGGGCAGGAG CAGGAGGAGG GGCAGGAGGG       780

GCAGGAGGGG CAGGAGGGGC AGGAGCAGGA GGAGGGGCAG GAGCAGGAGG AGGGGCAGGA      840

GGGGCAGGAG GGGCAGGAGC AGGAGGAGGG GCAGGAGCAG GAGGAGGGGC AGGAGGGGCA      900

GGAGCAGGAG GAGGGGCAGG AGGGGCAGGA GGGGCAGGAG CAGGAGGAGG GGCAGGAGCA      960

GGAGGAGGGG CAGGAGGGGC AGGAGCAGGA GGAGGGGCAG GAGGGGCAGG AGGGGCAGGA     1020

GCAGGAGGAG GGGCAGGAGC AGGAGGGGCA GGAGGGGCAG GAGGGGCAGG AGCAGGAGGG     1080

GCAGGAGCAG GAGGAGGGGC AGGAGGGGCA GGAGGGGCAG GAGCAGGAGG GGCAGGAGCA     1140

GGAGGGGCAG GAGCAGGAGG GGCAGGAGCA GGAGGGGCAG GAGGGGCAGG AGCAGGAGGG     1200

GCAGGAGGGG CAGGAGCAGG AGGGGCAGGA GGGGCAGGAG CAGGAGGAGG GGCAGGAGGG     1260

GCAGGAGCAG GAGGAGGGGC AGGAGGGGCA GGAGCAGGAG GGCAGGAGG GGCAGGAGCA      1320

GGAGGGGCAG GAGGGGCAGG AGCAGGAGGG GCAGGAGGGG CAGGAGCAGG AGGAGGGGCA     1380

GGAGCAGGAG GGGCAGGAGC AGGAGGTGGA GGCCGGGGTC GAGGAGGCAG TGGAGGCCGG     1440

GGTCGAGGAG GTAGTGGAGG CCGGGGTCGA GGAGGTAGTG GAGGCCGCCG GGGTAGAGGA     1500

CGTGAAAGAG CCAGGGGGG AAGTCGTGAA AGAGCCAGGG GGAGAGGTCG TGGACGTGGA      1560

GAAAAGAGGC CCAGGAGTCC CAGTAGTCAG TCATCATCAT CCGGGTCTCC ACCGCGCAGG     1620

CCCCCTCCAG GTAGAAGGCC ATTTTTCCAC CCTGTAGGGG AAGCCGATTA TTTTGAATAC     1680

CACCAAGAAG GTGGCCCAGA TGGTGAGCCT GACGTGCCCC CGGGAGCGAT AGAGCAGGGC     1740

CCCGCAGATG ACCCAGGAGA AGGCCCAAGC ACTGGACCCC GGGGTCAGGG TGATGGAGGC     1800

AGGCGCAAAA AAGGAGGGTG GTTTGGAAAG CATCGTGGTC AAGGAGGTTC AACCCGAAA      1860

TTTGAGAACA TTGCAGAAGG TTTAAGAGCT CTCCTGGCTA GGAGTCACGT AGAAAGGACT     1920

ACCGACGAAG GAACTTGGGT CGCCGGTGTG TTCGTATATG GAGGTAGTAA GACCTCCCTT     1980

TACAACCTAA GGCGAGGAAC TGCCCTTGCT ATTCCACAAT GTCGTCTTAC ACCATTGAGT     2040

CGTCTCCCCT TTGGAATGGC CCCTGGACCC GGCCACAAC CTGGCCCGCT AAGGGAGTCC      2100

ATTGTCTGTT ATTTCATGGT CTTTTTACAA ACTCATATAT TTGCTGAGGT TTTGAAGGAT     2160

GCGATTAAGG ACCTTGTTAT GACAAAGCCC GCTCCTACCT GCAATATCAG GGTGACTGTG     2220

TGCAGCTTTG ACGATGGAGT AGATTTGCCT CCCTGGTTTC CACCTATGGT GGAAGGGGCT     2280

GCCGCGGAGG GTGATGACGG AGATGACGGA GATGAAGGAG GTGATGGAGA TGAGGGTGAG     2340

GAAGGGCAGG AGTGATGTAA CTTGTTAGGA GACGCCCTCA ATCGTATTAA AAGCCGTGTA     2400

TTCCCCCGCA CTAAAGAATA AATCCCCAGT AGACATCATG CGTGCTGTTG GTGTATTTCT     2460

GGCCATCTGT CTTGTCACCA TTTTCGTCCT CCCAACATGG GGCAATTGGG CATACCCATG     2520

TTGTCACGTC ACTCAGCTCC GCGCTCAACA CCTTCTCGCG TTGGAAAACA TTAGCGACAT     2580

TTACCTGGTG AGCAATCAGA CATGCGACGG CTTTAGCCTG GCCTCCTTAA ATTCACCTAA     2640

GAATGGGAGC AACCAGCATG CAGGAAAAGG ACAAGCAGCG AAAATTCACG CCCCCTTGGG     2700

AGGTGGCGGC ATATGCAAAG GATAGCACTC CCACTCTACT ACTGGGTATC ATATGCTGAC     2760

TGTATATGCA TGAGGATAGC ATATGCTACC CGGATACAGA TTAGGATAGC ATATACTACC     2820

CAGATATAGA TTAGGATAGC ATATGCTACC CAGATATAGA TTAGGATAGC CTATGCTACC     2880

CAGATATAAA TTAGGATAGC ATATACTACC CAGATATAGA TTAGGATAGC ATATGCTACC     2940
```

```
CAGATATAGA TTAGGATAGC CTATGCTACC CAGATATAGA TTAGGATAGC ATATGCTACC    3000

CAGATATAGA TTAGGATAGC ATATGCTATC CAGATATTTG GGTAGTATAT GCTACCCAGA    3060

TATAAATTAG GATAGCATAT ACTACCCTAA TCTCTATTAG GATAGCATAT GCTACCCGGA    3120

TACAGATTAG GATAGCATAT ACTACCCAGA TATAGATTAG GATAGCATAT GCTACCCAGA    3180

TATAGATTAG GATAGCCTAT GCTACCCAGA TATAAATTAG GATAGCATAT ACTACCCAGA    3240

TATAGATTAG GATAGCATAT GCTACCCAGA TATAGATTAG GATAGCCTAT GCTACCCAGA    3300

TATAGATTAG GATAGCATAT GCTATCCAGA TATTTGGGTA GTATATGCTA CCCATGGCAA    3360

CATTAGCCCA CCGTGCTCTC AGCGACCTCG TGAATATGAG GACCAACAAC CCTGTGCTTG    3420

GCGCTCAGGC GCAAGTGTGT GTAATTTGTC CTCCAGATCG CAGCAATCGC GCCCCTATCT    3480

TGGCCCGCCC ACCTACTTAT GCAGGTATTC CCCGGGGTGC CATTAGTGGT TTTGTGGGCA    3540

AGTGGTTTGA CCGCAGTGGT TAGCGGGGTT ACAATCAGCC AAGTTATTAC ACCCTTATTT    3600

TACAGTCCAA AACCGCAGGG CGGCGTGTGG GGGCTGACGC GTGCCCCCAC TCCACAATTT    3660

CAAAAAAAAG AGTGGCCACT TGTCTTTGTT TATGGGCCCC ATTGGCGTGG AGCCCCGTTT    3720

AATTTTCGGG GGTGTTAGAG ACAACCAGTG GAGTCCGCTG CTGTCGGCGT CCACTCTCTT    3780

TCCCCTTGTT ACAAATAGAG TGTAACAACA TGGTTCACCT GTCTTGGTCC CTGCCTGGGA    3840

CACATCTTAA TAACCCCAGT ATCATATTGC ACTAGGATTA TGTGTTGCCC ATAGCCATAA    3900

ATTCGTGTGA GATGGACATC CAGTCTTTAC GGCTTGTCCC CACCCCATGG ATTTCTATTG    3960

TTAAAGATAT TCAGAATGTT TCATTCCTAC ACTAGTATTT ATTGCCCAAG GGGTTTGTGA    4020

GGGTTATATT GGTGTCATAG CACAATGCCA CCACTGAACC CCCCGTCCAA ATTTTATTCT    4080

GGGGGCGTCA CCTGAAACCT TGTTTTCGAG CACCTCACAT ACACCTTACT GTTCACAACT    4140

CAGCAGTTAT TCTATTAGCT AAACGAAGGA GAATGAAGAA GCAGGCGAAG ATTCAGGAGA    4200

GTTCACTGCC CGCTCCTTGA TCTTCAGCCA CTGCCCTTGT GACTAAAATG GTTCACTACC    4260

CTCGTGGAAT CCTGACCCCA TGTAAATAAA ACCGTGACAG CTCATGGGGT GGGAGATATC    4320

GCTGTTCCTT AGGACCCTTT TACTAACCCT AATTCGATAG CATATGCTTC CCGTTGGGTA    4380

ACATATGCTA TTGAATTAGG GTTAGTCTGG ATAGTATATA CTACTACCCG GAAGCATAT    4440

GCTACCCGTT TAGGGTTAAC AAGGGGGCCT TATAAACACT ATTGCTAATG CCCTCTTGAG    4500

GGTCCGCTTA TCGGTAGCTA CACAGGCCCC TCTGATTGAC GTTGGTGTAG CCTCCCGTAG    4560

TCTTCCTGGG CCCCTGGGAG GTACATGTCC CCCAGCATTG GTGTAAGAGC TTCAGCCAAG    4620

AGTTACACAT AAAGGCAATG TTGTGTTGCA GTCCACAGCA TGCAAAGTCT GCTCCAGGAT    4680

GAAAGCCACT CAGTGTTGGC AAATGTGCAC ATCCATTTAT AAGGATGTCA ACTACAGTCA    4740

GAGAACCCCT TTGTGTTTGG TCCCCCCCCG TGTCACATGT GGAACAGGGC CCAGTTGGCA    4800

AGTTGTACCA ACCAACTGAA GGGATTACAT GCACTGCCCC GAATACAAAA CAAAAGCGCT    4860

CCTCGTACCA GCGAAGAAGG GGCAGAGATG CCGTAGTCAG GTTTAGTTCG TCCGGCGGCG    4920

GGGCGATCCG CGGCCGCCTG CGCGCTCGCT CGCTCACTGA GGCCGCCCGG GCAAAGCCCG    4980

GGCGTCGGGC GACCTTTGGT CGCCCGGCCT CAGTGAGCGA GCGAGCGCGC AGAGAGGGAG    5040

TGGCCAACTC CATCACTAGG GGTTCCTTGT AGTTAATGAT TAACCCGCCA TGCTACTTAT    5100

CTACGGCCGC GGAATTTCGA CTCTAGGCCA TTGCATACGT TGTATCTATA TCATAATATG    5160

TACATTTATA TTGGCTCATG TCCAATATGA CCGCCATGTT GACATTGATT ATTGACTAGT    5220

TATTAATAGT AATCAATTAC GGGGTCATTA GTTCATAGCC CATATATGGA GTTCCGCGTT    5280
```

-continued

```
ACATAACTTA CGGTAAATGG CCCGCCTGGC TGACCGCCCA ACGACCCCCG CCCATTGACG    5340

TCAATAATGA CGTATGTTCC CATAGTAACG CCAATAGGGA CTTTCCATTG ACGTCAATGG    5400

GTGGAGTATT TACGGTAAAC TGCCCACTTG GCAGTACATC AAGTGTATCA TATGCCAAGT    5460

CCGCCCCCTA TTGACGTCAA TGACGGTAAA TGGCCCGCCT GGCATTATGC CCAGTACATG    5520

ACCTTACGGG ACTTTCCTAC TTGGCAGTAC ATCTACGTAT TAGTCATCGC TATTACCATG    5580

GTGATGCGGT TTTGGCAGTA CACCAATGGG CGTGGATAGC GGTTTGACTC ACGGGGATTT    5640

CCAAGTCTCC ACCCCATTGA CGTCAATGGG AGTTTGTTTT GGCACCAAAA TCAACGGGAC    5700

TTTCCAAAAT GTCGTAATAA CCCCGCCCCG TTGACGCAAA TGGGCGGTAG GCGTGTACGG    5760

TGGGAGGTCT ATATAAGCAG AGCTCGTTTA GTGAACCGTC AGATCGCCTG GAGACGCCAT    5820

CCACGCTGTT TTGACCTCCA TAGAAGACAC CGGGACCGAT CCAGCCTCCG CGGCCGGGAA    5880

CGGTGCATTG GAACGCGGAT TCCCCGTGCC AAGAGTGACG TAAGTACCGC CTATAGACTC    5940

TATAGGCACA CCCCTTTGGC TCTTATGCAT GCTATACTGT TTTTGGCTTG GGGCCTATAC    6000

ACCCCCGCTC CTTATGCTAT AGGTGATGGT ATAGCTTAGC CTATAGGTGT GGGTTATTGA    6060

CCATTATTGA CCACTCCCCT ATTGGTGACG ATACTTTCCA TTACTAATCC ATAACATGGC    6120

TCTTTGCCAC AACTATCTCT ATTGGCTATA TGCCAATACT CTGTCCTTCA GAGACTGACA    6180

CGGACTCTGT ATTTTTACAG GATGGGGTCC ATTTATTATT TACAAATTCA CATATACAAC    6240

AACGCCGTCC CCCGTGCCCG CAGTTTTTAT TAAACATAGC GTGGGATCTC CGACATCTCG    6300

GGTACGTGTT CCGGACATGG GCTCTTCTCC GGTAGCGGCG GAGCTTCCAC ATCCGAGCCC    6360

TGGTCCCATC CGTCCAGCGG CTCATGGTCG CTCGGCAGCT CCTTGCTCCT AACAGTGGAG    6420

GCCAGACTTA GGCACAGCAC AATGCCCACC ACCACCAGTG TGCCGCACAA GGCCGTGGCG    6480

GTAGGGTATG TGTCTGAAAA TGAGCTCGGA GATTGGGCTC GCACCTGGAC GCAGATGGAA    6540

GACTTAAGGC AGCGGCAGAA GAAGATGCAG GCAGCTGAGT TGTTGTATTC TGATAAGAGT    6600

CAGAGGTAAC TCCCGTTGCG GTGCTGTTAA CGGTGGAGGG CAGTGTAGTC TGAGCAGTAC    6660

TCGTTGCTGC CGCGCGCGCC ACCAGACATA ATAGCTGACA GACTAACAGA CTGTTCCTTT    6720

CCATGGGTCT TTTCTGCAGT CACCGTCGTC GACCTAAGAA TTCAGACTCG AGCAAGTCTA    6780

GAAAGCCATG GATATCGGAT CCACTACGCG TTAGAGCTCG CTGATCAGCC TCGACTGTGC    6840

CTTCTAGTTG CCAGCCATCT GTTGTTTGCC CCTCCCCCGT GCCTTCCTTG ACCCTGGAAG    6900

GTGCCACTCC CACTGTCCTT TCCTAATAAA ATGAGGAAAT TGCATCGCAT TGTCTGAGTA    6960

GGTGTCATTC TATTCTGGGG GGTGGGGTGG GGCAGGACAG CAAGGGGGAG GATTGGGAAG    7020

ACAATAGCAG GGGGTGGGC GAAGAACTCC AGCATGAGAT CCCCGCGCTG GAGGATCATC    7080

CAGCCGGCGT CCCGGAAAAC GATTCCGAAG CCCAACCTTT CATAGAAGGC GGCGGTGGAA    7140

TCGAAATCTC GTGATGGCAG GTTGGGCGTC GCTTGGTCGG TCATTTCGGT AGATAAGTAG    7200

CATGGCGGGT TAATCATTAA CTACAAGGAA CCCCTAGTGA TGGAGTTGGC CACTCCCTCT    7260

CTGCGCGCTC GCTCGCTCAC TGAGGCCGGG CGACCAAAGG TCGCCCGACG CCCGGGCTTT    7320

GCCCGGGCGG CCTCAGTGAG CGAGCGAGCG CGCAGCGAAC CCCAGAGTCC CGCTCAGAAG    7380

AACTCGTCAA GAAGGCGATA GAAGGCGATG CGCTGCGAAT CGGGAGCGGC GATACCGTAA    7440

AGCACGAGGA AGCGGTCAGC CCATTCGCCG CCAAGCTCTT CAGCAATATC ACGGGTAGCC    7500

AACGCTATGT CCTGATAGCG GTCCGCCACA CCCAGCCGGC CACAGTCGAT GAATCCAGAA    7560

AAGCGGCCAT TTTCCACCAT GATATTCGGC AAGCAGGCAT CGCCATGGGT CACGACGAGA    7620

TCCTCGCCGT CGGGCATGCG CGCCTTGAGC CTGGCGAACA GTTCGGCTGG CGCGAGCCCC    7680
```

```
TGATGCTCTT CGTCCAGATC ATCCTGATCG ACAAGACCGG CTTCCATCCG AGTACGTGCT    7740

CGCTCGATGC GATGTTTCGC TTGGTGGTCG AATGGGCAGG TAGCCGGATC AAGCGTATGC    7800

AGCCGCCGCA TTGCATCAGC CATGATGGAT ACTTTCTCGG CAGGAGCAAG GTGAGATGAC    7860

AGGAGATCCT GCCCCGGCAC TTCGCCCAAT AGCAGCCAGT CCCTTCCCGC TTCAGTGACA    7920

ACGTCGAGCA CAGCTGCGCA AGGAACGCCC GTCGTGGCCA GCCACGATAG CCGCGCTGCC    7980

TCGTCCTGCA GTTCATTCAG GGCACCGGAC AGGTCGGTCT TGACAAAAAG AACCGGGCGC    8040

CCCTGCGCTG ACAGCCGGAA CACGGCGGCA TCAGAGCAGC CGATTGTCTG TTGTGCCCAG    8100

TCATAGCCGA ATAGCCTCTC CACCCAAGCG GCCGGAGAAC CTGCGTGCAA TCCATCTTGT    8160

TCAATCATGC GAAACGATCC TCATCCTGTC TCTTGATCAG ATCTTGATCC CCTGCGCCAT    8220

CAGATCCTTG GCGGCAAGAA AGCCATCCAG TTTACTTTGC AGGGCTTCCC AACCTTACCA    8280

GAGGGCGCCC CAGCTGGCAA TTCCGGTTCG CTTGCTGTCC ATAAAACCGC CCAGTCTAGC    8340

TATCGCCATG TAAGCCCACT GCAAGCTACC TGCTTTCTCT TTGCGCTTGC GTTTTCCCTT    8400

GTCCAGATAG CCCAGTAGCT GACATTCATC CGGGGTCAGC ACCGTTTCTG CGGACTGGCT    8460

TTCTACGTGT TCCGCTTCCT TTAGCAGCCC TTGCGCCCTG AGTGCTTGCG GCAGCGTGAA    8520

GCTGTCAATT CCGCGTTAAA TTTTTGTTAA ATCAGCTCAT TTTTTAACCA ATAGGCCGAA    8580

ATCGGCAAAA TCCCTTATAA ATCAAAGAA TAGCCCGAGA TAGGGTTGAG TGTTGTTCCA     8640

GTTTGGAACA AGAGTCCACT ATTAAAGAAC GTGGACTCCA ACGTCAAAGG GCGAAAAACC    8700

GTCTATCAGG GCGATGGCGG ATCAGCTTAT GCGGTGTGAA ATACCGCACA GATGCGTAAG    8760

GAGAAAATAC CGCATCAGGC GCTCTTCCGC TTCCTCGCTC ACTGACTCGC TGCGCTCGGT    8820

CGTTCGGCTG CGGCGAGCGG TATCAGCTCA CTCAAAGGCG GTAATACGGT TATCCACAGA    8880

ATCAGGGGAT AACGCAGGAA AGAACATGTG AGCAAAAGGC CAGCAAAAGG CCAGGAACCG    8940

TAAAAAGGCC GCGTTGCTGG CGTTTTTCCA TAGGCTCCGC CCCCCTGACG AGCATCACAA    9000

AAATCGACGC TCAAGTCAGA GGTGGCGAAA CCCGACAGGA CTATAAAGAT ACCAGGCGTT    9060

TCCCCCTGGA AGCTCCCTCG TGCGCTCTCC TGTTCCGACC CTGCCGCTTA CCGGATACCT    9120

GTCCGCCTTT CTCCCTTCGG GAAGCGTGGC GCTTTCTCAT AGCTCACGCT GTAGGTATCT    9180

CAGTTCGGTG TAGGTCGTTC GCTCCAAGCT GGGCTGTGTG CACGAACCCC CCGTTCAGCC    9240

CGACCGCTGC GCCTTATCCG GTAACTATCG TCTTGAGTCC AACCCGGTAA GACACGACTT    9300

ATCGCCACTG GCAGCAGCCA CTGGTAACAG GATTAGCAGA GCGAGGTATG TAGGCGGTGC    9360

TACAGAGTTC TTGAAGTGGT GGCCTAACTA CGGCTACACT AGAAGGACAG TATTTGGTAT    9420

CTGCGCTCTG CTGAAGCCAG TTACCTTCGG AAAAAGAGTT GGTAGCTCTT GATCCGGCAA    9480

ACAAACCACC GCTGGTAGCG GCGGTTTTTT GTTTGCAAGC AGCAGATTAC GCGCAGAAAA    9540

AAAGGATCTC AAGAAGATCC TTTGATCTTT TCTTACTGAA CGGTGATCCC CACCGGAATT    9600
```

(2) INFORMATION FOR SEQ ID NO:2:

(i) SEQUENCE CHARACTERISTICS:
        (A) LENGTH: 4328 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:2:

```
GCCGCGGAAT TCGACTCTA GGCCATTGCA TACGTTGTAT CTATATCATA ATATGTACAT       60
```

```
TTATATTGGC TCATGTCCAA TATGACCGCC ATGTTGACAT TGATTATTGA CTAGTTATTA   120
ATAGTAATCA ATTACGGGGT CATTAGTTCA TAGCCCATAT ATGGAGTTCC GCGTTACATA   180
ACTTACGGTA AATGGCCCGC CTGGCTGACC GCCCAACGAC CCCCGCCCAT TGACGTCAAT   240
AATGACGTAT GTTCCCATAG TAACGCCAAT AGGGACTTTC CATTGACGTC AATGGGTGGA   300
GTATTTACGG TAAACTGCCC ACTTGGCAGT ACATCAAGTG TATCATATGC CAAGTCCGCC   360
CCCTATTGAC GTCAATGACG GTAAATGGCC CGCCTGGCAT TATGCCCAGT ACATGACCTT   420
ACGGGACTTT CCTACTTGGC AGTACATCTA CGTATTAGTC ATCGCTATTA CCATGGTGAT   480
GCGGTTTTGG CAGTACACCA ATGGGCGTGG ATAGCGGTTT GACTCACGGG GATTTCCAAG   540
TCTCCACCCC ATTGACGTCA ATGGGAGTTT GTTTTGGCAC CAAAATCAAC GGGACTTTCC   600
AAAATGTCGT AATAACCCCG CCCCGTTGAC GCAAATGGGC GGTAGGCGTG TACGGTGGGA   660
GGTCTATATA AGCAGAGCTC GTTTAGTGAA CCGTCAGATC GCCTGGAGAC GCCATCCACG   720
CTGTTTTGAC CTCCATAGAA GACACCGGGA CCGATCCAGC CTCCGCGGCC GGGAACGGTG   780
CATTGGAACG CGGATTCCCC GTGCCAAGAG TGACGTAAGT ACCGCCTATA GACTCTATAG   840
GCACACCCCT TTGGCTCTTA TGCATGCTAT ACTGTTTTTG GCTTGGGGCC TATACACCCC   900
CGCTCCTTAT GCTATAGGTG ATGGTATAGC TTAGCCTATA GGTGTGGGTT ATTGACCATT   960
ATTGACCACT CCCCTATTGG TGACGATACT TTCCATTACT AATCCATAAC ATGGCTCTTT  1020
GCCACAACTA TCTCTATTGG CTATATGCCA ATACTCTGTC CTTCAGAGAC TGACACGGAC  1080
TCTGTATTTT TACAGGATGG GGTCCATTTA TTATTTACAA ATTCACATAT ACAACAACGC  1140
CGTCCCCCGT GCCCGCAGTT TTTATTAAAC ATAGCGTGGG ATCTCCGACA TCTCGGGTAC  1200
GTGTTCCGGA CATGGGCTCT TCTCCGGTAG CGGCGGAGCT TCCACATCCG AGCCCTGGTC  1260
CCATCCGTCC AGCGGCTCAT GGTCGCTCGG CAGCTCCTTG CTCCTAACAG TGGAGGCCAG  1320
ACTTAGGCAC AGCACAATGC CCACCACCAC CAGTGTGCCG CACAAGGCCG TGGCGGTAGG  1380
GTATGTGTCT GAAAATGAGC TCGGAGATTG GGCTCGCACC TGGACGCAGA TGGAAGACTT  1440
AAGGCAGCGG CAGAAGAAGA TGCAGGCAGC TGAGTTGTTG TATTCTGATA AGAGTCAGAG  1500
GTAACTCCCG TTGCGGTGCT GTTAACGGTG GAGGGCAGTG TAGTCTGAGC AGTACTCGTT  1560
GCTGCCGCGC GCGCCACCAG ACATAATAGC TGACAGACTA ACAGACTGTT CCTTTCCATG  1620
GGTCTTTTCT GCAGTCACCG TCGTCGACCT AAGAATTCAG ACTCGAGCAA GTCTAGAAAG  1680
CCATGGATAT CGGATCCACT ACGCGTTAGA GCTCGCTGAT CAGCCTCGAC TGTGCCTTCT  1740
AGTTGCCAGC CATCTGTTGT TTGCCCCTCC CCCGTGCCTT CCTTGACCCT GGAAGGTGCC  1800
ACTCCCACTG TCCTTTCCTA ATAAAATGAG GAAATTGCAT CGCATTGTCT GAGTAGGTGT  1860
CATTCTATTC TGGGGGGTGG GGTGGGGCAG GACAGCAAGG GGGAGGATTG GGAAGACAAT  1920
AGCAGGGGGG TGGGCGAAGA ACTCCAGCAT GAGATCCCCG CGCTGGAGGA TCATCCAGCC  1980
GGCGTCCCGG AAAACGATTC CGAAGCCCAA CCTTTCATAG AAGGCGGCGG TGGAATCGAA  2040
ATCTCGTGAT GGCAGGTTGG CGTCGCTTG  GTCGGTCATT TCGAACCCCA GAGTCCCGCT  2100
CAGAAGAACT CGTCAAGAAG GCGATAGAAG GCGATGCGCT GCGAATCGGG AGCGGCGATA  2160
CCGTAAAGCA CGAGGAAGCG GTCAGCCCAT TCGCCGCCAA GCTCTTCAGC AATATCACGG  2220
GTAGCCAACG CTATGTCCTG ATAGCGGTCC GCCACACCCA GCCGGCCACA GTCGATGAAT  2280
CCAGAAAAGC GGCCATTTTC CACCATGATA TTCGGCAAGC AGGCATCGCC ATGGGTCACG  2340
ACGAGATCCT CGCCGTCGGG CATGCGCGCC TTGAGCCTGG CGAACAGTTC GGCTGGCGCG  2400
```

```
AGCCCCTGAT GCTCTTCGTC CAGATCATCC TGATCGACAA GACCGGCTTC CATCCGAGTA    2460

CGTGCTCGCT CGATGCGATG TTTCGCTTGG TGGTCGAATG GGCAGGTAGC CGGATCAAGC    2520

GTATGCAGCC GCCGCATTGC ATCAGCCATG ATGGATACTT TCTCGGCAGG AGCAAGGTGA    2580

GATGACAGGA GATCCTGCCC CGGCACTTCG CCCAATAGCA GCCAGTCCCT TCCCGCTTCA    2640

GTGACAACGT CGAGCACAGC TGCGCAAGGA ACGCCCGTCG TGGCCAGCCA CGATAGCCGC    2700

GCTGCCTCGT CCTGCAGTTC ATTCAGGGCA CCGGACAGGT CGGTCTTGAC AAAAAGAACC    2760

GGGCGCCCCT GCGCTGACAG CCGGAACACG GCGGCATCAG AGCAGCCGAT TGTCTGTTGT    2820

GCCCAGTCAT AGCCGAATAG CCTCTCCACC CAAGCGGCCG GAGAACCTGC GTGCAATCCA    2880

TCTTGTTCAA TCATGCGAAA CGATCCTCAT CCTGTCTCTT GATCAGATCT TGATCCCCTG    2940

CGCCATCAGA TCCTTGGCGG CAAGAAAGCC ATCCAGTTTA CTTTGCAGGG CTTCCCAACC    3000

TTACCAGAGG GCGCCCCAGC TGGCAATTCC GGTTCGCTTG CTGTCCATAA AACCGCCCAG    3060

TCTAGCTATC GCCATGTAAG CCCACTGCAA GCTACCTGCT TTCTCTTTGC GCTTGCGTTT    3120

TCCCTTGTCC AGATAGCCCA GTAGCTGACA TTCATCCGGG GTCAGCACCG TTTCTGCGGA    3180

CTGGCTTTCT ACGTGTTCCG CTTCCTTTAG CAGCCCTTGC GCCCTGAGTG CTTGCGGCAG    3240

CGTGAAGCTG TCAATTCCGC GTTAAATTTT TGTTAAATCA GCTCATTTTT TAACCAATAG    3300

GCCGAAATCG GCAAAATCCC TTATAAATCA AAAGAATAGC CCGAGATAGG GTTGAGTGTT    3360

GTTCCAGTTT GGAACAAGAG TCCACTATTA AGAACGTGG ACTCCAACGT CAAAGGGCGA     3420

AAAACCGTCT ATCAGGGCGA TGGCGGATCA GCTTATGCGG TGTGAAATAC CGCACAGATG    3480

CGTAAGGAGA AAATACCGCA TCAGGCGCTC TTCCGCTTCC TCGCTCACTG ACTCGCTGCG    3540

CTCGGTCGTT CGGCTGCGGC GAGCGGTATC AGCTCACTCA AAGGCGGTAA TACGGTTATC    3600

CACAGAATCA GGGGATAACG CAGGAAAGAA CATGTGAGCA AAAGGCCAGC AAAAGGCCAG    3660

GAACCGTAAA AAGGCCGCGT TGCTGGCGTT TTTCCATAGG CTCCGCCCCC CTGACGAGCA    3720

TCACAAAAAT CGACGCTCAA GTCAGAGGTG GCGAAACCCG ACAGGACTAT AAAGATACCA    3780

GGCGTTTCCC CCTGGAAGCT CCCTCGTGCG CTCTCCTGTT CCGACCCTGC CGCTTACCGG    3840

ATACCTGTCC GCCTTTCTCC CTTCGGGAAG CGTGGCGCTT TCTCATAGCT CACGCTGTAG    3900

GTATCTCAGT TCGGTGTAGG TCGTTCGCTC CAAGCTGGGC TGTGTGCACG AACCCCCCGT    3960

TCAGCCCGAC CGCTGCGCCT TATCCGGTAA CTATCGTCTT GAGTCCAACC CGGTAAGACA    4020

CGACTTATCG CCACTGGCAG CAGCCACTGG TAACAGGATT AGCAGAGCGA GGTATGTAGG    4080

CGGTGCTACA GAGTTCTTGA AGTGGTGGCC TAACTACGGC TACACTAGAA GGACAGTATT    4140

TGGTATCTGC GCTCTGCTGA AGCCAGTTAC CTTCGGAAAA AGAGTTGGTA GCTCTTGATC    4200

CGGCAAACAA ACCACCGCTG GTAGCGGCGG TTTTTTGTTT GCAAGCAGCA GATTACGCGC    4260

AGAAAAAAAG GATCTCAAGA AGATCCTTTG ATCTTTTCTA CTGAACGGTG ATCCCCACCG    4320

GAATTGCG                                                            4328
```

(2) INFORMATION FOR SEQ ID NO:3:

(i) SEQUENCE CHARACTERISTICS:
        (A) LENGTH: 5107 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

-continued

```
GCGGCCGCGG AATTTCGACT CTAGGCCATT GCATACGTTG TATCTATATC ATAATATGTA      60

CATTTATATT GGCTCATGTC CAATATGACC GCCATGTTGA CATTGATTAT TGACTAGTTA     120

TTAATAGTAA TCAATTACGG GGTCATTAGT TCATAGCCCA TATATGGAGT TCCGCGTTAC     180

ATAACTTACG GTAAATGGCC CGCCTGGCTG ACCGCCCAAC GACCCCCGCC CATTGACGTC     240

AATAATGACG TATGTTCCCA TAGTAACGCC AATAGGGACT TTCCATTGAC GTCAATGGGT     300

GGAGTATTTA CGGTAAACTG CCCACTTGGC AGTACATCAA GTGTATCATA TGCCAAGTCC     360

GCCCCCTATT GACGTCAATG ACGGTAAATG GCCCGCCTGG CATTATGCCC AGTACATGAC     420

CTTACGGGAC TTTCCTACTT GGCAGTACAT CTACGTATTA GTCATCGCTA TTACCATGGT     480

GATGCGGTTT TGGCAGTACA CCAATGGGCG TGGATAGCGG TTTGACTCAC GGGGATTTCC     540

AAGTCTCCAC CCCATTGACG TCAATGGGAG TTTGTTTTGG CACCAAAATC AACGGGACTT     600

TCCAAAATGT CGTAATAACC CCGCCCCGTT GACGCAAATG GGCGGTAGGC GTGTACGGTG     660

GGAGGTCTAT ATAAGCAGAG CTCGTTTAGT GAACCGTCAG ATCGCCTGGA GACGCCATCC     720

ACGCTGTTTT GACCTCCATA GAAGACACCG GGACCGATCC AGCCTCCGCG GCCGGGAACG     780

GTGCATTGGA ACGCGGATTC CCCGTGCCAA GAGTGACGTA AGTACCGCCT ATAGACTCTA     840

TAGGCACACC CCTTTGGCTC TTATGCATGC TATACTGTTT TTGGCTTGGG GCCTATACAC     900

CCCCGCTCCT TATGCTATAG GTGATGGTAT AGCTTAGCCT ATAGGTGTGG GTTATTGACC     960

ATTATTGACC ACTCCCCTAT TGGTGACGAT ACTTTCCATT ACTAATCCAT AACATGGCTC    1020

TTTGCCACAA CTATCTCTAT TGGCTATATG CCAATACTCT GTCCTTCAGA GACTGACACG    1080

GACTCTGTAT TTTTACAGGA TGGGGTCCAT TTATTATTTA CAAATTCACA TATACAACAA    1140

CGCCGTCCCC CGTGCCCGCA GTTTTTATTA AACATAGCGT GGGATCTCCG ACATCTCGGG    1200

TACGTGTTCC GGACATGGGC TCTTCTCCGG TAGCGGCGGA GCTTCCACAT CCGAGCCCTG    1260

GTCCCATCCG TCCAGCGGCT CATGGTCGCT CGGCAGCTCC TTGCTCCTAA CAGTGGAGGC    1320

CAGACTTAGG CACAGCACAA TGCCCACCAC CACCAGTGTG CCGCACAAGG CCGTGGCGGT    1380

AGGGTATGTG TCTGAAAATG AGCTCGGAGA TTGGGCTCGC ACCTGGACGC AGATGGAAGA    1440

CTTAAGGCAG CGGCAGAAGA AGATGCAGGC AGCTGAGTTG TTGTATTCTG ATAAGAGTCA    1500

GAGGTAACTC CCGTTGCGGT GCTGTTAACG GTGGAGGGCA GTGTAGTCTG AGCAGTACTC    1560

GTTGCTGCCG CGCGCGCCAC CAGACATAAT AGCTGACAGA CTAACAGACT GTTCCTTTCC    1620

ATGGGTCTTT TCTGCAGTCA CCGTCGTCGA CCTAAGAATT CAGACTCGAG CAAGTCTAGG    1680

TCGCTGAGGG ACCCCGGCCA GGCGCGGAGA TGGGGGTGCA CGAATGTCCT GCCTGGCTGT    1740

GGCTTCTCCT GTCTCTCGTG TCGCTCCCTC TGGGCCTCCC AGTCCGGGC GCCCCACCAC    1800

GCCTCATCTG TGACAGCCGA GTCCTGGAGA GGTACCTCTT GGAGGCCAAG GAGGCCGAGA    1860

ATGTCACGAT GGGCTGTTCC GAAAGCTGCA GCTTGAATGA GAATATCACC GTCCCAGACA    1920

CCAAAGTTAA CTTCTATGCC TGGAAGAGGA TGGAGGTCGG GCAGCAGGCT GTAGAAGTCT    1980

GGCAGGGCCT GGCCCTGCTC TCAGAAGCTG TCCTGCGGGG CCAGGCCGTG TTGGCCAACT    2040

CTTCCCAGCC TTTCGAGCCC CTGCAGCTGC ACATGGATAA AGCCATCAGT GGCCTTCGCA    2100

GCATCACCAC TCTGCTTCGG GCGCTGGGAG CCCAGGAAGC CATCTCCCTC CCAGATGCGG    2160

CCTCGGCTGC TCCACTCCGA ACCATCACTG CTGACACTTT CTGCAAACTC TTCCGAGTCT    2220

ACTCCAATTT CCTCCGGGGA AAGCTGAAGC TGTACACGGG GGAGGCCTGC AGGAGAGGGG    2280

ACAGATGACC AGGTGCGTCC AGCTGGGCAC ATCCACCACC TCCCTCACCA ACACTGCCTG    2340

TGCCACACCC TCCCTCACCA CTCCCGAACC CCATCGAGGG GCTCTCAGCT AAGCGCCAGC    2400
```

```
CTGTCCCATG GACACTCCAG TGCCAGCAAT GACATCTCAG GGGCCAGAGG AACTGTCCAG     2460

AGCACAACTC TGAGATCCAC TACGCGTTAG AGCTCGCTGA TCAGCCTCGA CTGTGCCTTC     2520

TAGTTGCCAG CCATCTGTTG TTTGCCCCTC CCCCGTGCCT TCCTTGACCC TGGAAGGTGC     2580

CACTCCCACT GTCCTTTCCT AATAAAATGA GGAAATTGCA TCGCATTGTC TGAGTAGGTG     2640

TCATTCTATT CTGGGGGGTG GGGTGGGGCA GGACAGCAAG GGGGAGGATT GGGAAGACAA     2700

TAGCAGGGGG GTGGGCGAAG AACTCCAGCA TGAGATCCCC GCGCTGGAGG ATCATCCAGC     2760

CGGCGTCCCG GAAAACGATT CCGAAGCCCA ACCTTTCATA GAAGGCGGCG GTGGAATCGA     2820

AATCTCGTGA TGGCAGGTTG GGCGTCGCTT GGTCGGTCAT TTCGAACCCC AGAGTCCCGC     2880

TCAGAAGAAC TCGTCAAGAA GGCGATAGAA GGCGATGCGC TGCGAATCGG GAGCGGCGAT     2940

ACCGTAAAGC ACGAGGAAGC GGTCAGCCCA TTCGCCGCCA AGCTCTTCAG CAATATCACG     3000

GGTAGCCAAC GCTATGTCCT GATAGCGGTC CGCCACACCC AGCCGGCCAC AGTCGATGAA     3060

TCCAGAAAAG CGGCCATTTT CCACCATGAT ATTCGGCAAG CAGGCATCGC CATGGGTCAC     3120

GACGAGATCC TCGCCGTCGG GCATGCGCGC CTTGAGCCTG GCGAACAGTT CGGCTGGCGC     3180

GAGCCCCTGA TGCTCTTCGT CCAGATCATC CTGATCGACA AGACCGGCTT CCATCCGAGT     3240

ACGTGCTCGC TCGATGCGAT GTTTCGCTTG GTGGTCGAAT GGGCAGGTAG CCGGATCAAG     3300

CGTATGCAGC CGCCGCATTG CATCAGCCAT GATGGATACT TTCTCGGCAG GAGCAAGGTG     3360

AGATGACAGG AGATCCTGCC CCGGCACTTC GCCCAATAGC AGCCAGTCCC TTCCCGCTTC     3420

AGTGACAACG TCGAGCACAG CTGCGCAAGG AACGCCCGTC GTGGCCAGCC ACGATAGCCG     3480

CGCTGCCTCG TCCTGCAGTT CATTCAGGGC ACCGGACAGG TCGGTCTTGA CAAAAAGAAC     3540

CGGGCGCCCC TGCGCTGACA GCCGGAACAC GGCGGCATCA GAGCAGCCGA TTGTCTGTTG     3600

TGCCCAGTCA TAGCCGAATA GCCTCTCCAC CCAAGCGGCC GGAGAACCTG CGTGCAATCC     3660

ATCTTGTTCA ATCATGCGAA ACGATCCTCA TCCTGTCTCT TGATCAGATC TTGATCCCCT     3720

GCGCCATCAG ATCCTTGGCG GCAAGAAAGC CATCCAGTTT ACTTTGCAGG GCTTCCCAAC     3780

CTTACCAGAG GGCGCCCCAG CTGGCAATTC CGGTTCGCTT GCTGTCCATA AAACCGCCCA     3840

GTCTAGCTAT CGCCATGTAA GCCCACTGCA AGCTACCTGC TTTCTCTTTG CGCTTGCGTT     3900

TTCCCTTGTC CAGATAGCCC AGTAGCTGAC ATTCATCCGG GGTCAGCACC GTTTCTGCGG     3960

ACTGGCTTTC TACGTGTTCC GCTTCCTTTA GCAGCCCTTG CGCCCTGAGT GCTTGCGGCA     4020

GCGTGAAGCT GTCAATTCCG CGTTAAATTT TTGTTAAATC AGCTCATTTT TTAACCAATA     4080

GGCCGAAATC GGCAAAATCC CTTATAAATC AAAAGAATAG CCCGAGATAG GGTTGAGTGT     4140

TGTTCCAGTT TGGAACAAGA GTCCACTATT AAAGAACGTG GACTCCAACG TCAAAGGGCG     4200

AAAAACCGTC TATCAGGGCG ATGGCGGATC AGCTTATGCG GTGTGAAATA CCGCACAGAT     4260

GCGTAAGGAG AAAATACCGC ATCAGGCGCT CTTCCGCTTC CTCGCTCACT GACTCGCTGC     4320

GCTCGGTCGT TCGGCTGCGG CGAGCGGTAT CAGCTCACTC AAAGGCGGTA ATACGGTTAT     4380

CCACAGAATC AGGGGATAAC GCAGGAAAGA ACATGTGAGC AAAAGGCCAG CAAAAGGCCA     4440

GGAACCGTAA AAAGGCCGCG TTGCTGGCGT TTTTCCATAG GCTCCGCCCC CCTGACGAGC     4500

ATCACAAAAA TCGACGCTCA AGTCAGAGGT GGCGAAACCC GACAGGACTA TAAAGATACC     4560

AGGCGTTTCC CCCTGGAAGC TCCCTCGTGC GCTCTCCTGT TCCGACCCTG CCGCTTACCG     4620

GATACCTGTC CGCCTTTCTC CCTTCGGGAA GCGTGGCGCT TTCTCATAGC TCACGCTGTA     4680

GGTATCTCAG TTCGGTGTAG GTCGTTCGCT CCAAGCTGGG CTGTGTGCAC GAACCCCCCG     4740
```

-continued

| | | | | |
|---|---|---|---|---|
| TTCAGCCCGA | CCGCTGCGCC | TTATCCGGTA | ACTATCGTCT | TGAGTCCAAC | CCGGTAAGAC | 4800 |
| ACGACTTATC | GCCACTGGCA | GCAGCCACTG | GTAACAGGAT | TAGCAGAGCG | AGGTATGTAG | 4860 |
| GCGGTGCTAC | AGAGTTCTTG | AAGTGGTGGC | CTAACTACGG | CTACACTAGA | AGGACAGTAT | 4920 |
| TTGGTATCTG | CGCTCTGCTG | AAGCCAGTTA | CCTTCGGAAA | AAGAGTTGGT | AGCTCTTGAT | 4980 |
| CCGGCAAACA | AACCACCGCT | GGTAGCGGCG | GTTTTTTGTT | TGCAAGCAGC | AGATTACGCG | 5040 |
| CAGAAAAAAA | GGATCTCAAG | AAGATCCTTT | GATCTTTTCT | TACTGAACGG | TGATCCCCAC | 5100 |
| CGGAATT | | | | | | 5107 |

(2) INFORMATION FOR SEQ ID NO:4:

(i) SEQUENCE CHARACTERISTICS:
        (A) LENGTH: 4818 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

| | | | | | | |
|---|---|---|---|---|---|---|
| GCGGCCGCGG | AATTTCGACT | CTAGGCCATT | GCATACGTTG | TATCTATATC | ATAATATGTA | 60 |
| CATTTATATT | GGCTCATGTC | CAATATGACC | GCCATGTTGA | CATTGATTAT | TGACTAGTTA | 120 |
| TTAATAGTAA | TCAATTACGG | GGTCATTAGT | TCATAGCCCA | TATATGGAGT | TCCGCGTTAC | 180 |
| ATAACTTACG | GTAAATGGCC | CGCCTGGCTG | ACCGCCCAAC | GACCCCCGCC | CATTGACGTC | 240 |
| AATAATGACG | TATGTTCCCA | TAGTAACGCC | AATAGGGACT | TTCCATTGAC | GTCAATGGGT | 300 |
| GGAGTATTTA | CGGTAAACTG | CCCACTTGGC | AGTACATCAA | GTGTATCATA | TGCCAAGTCC | 360 |
| GCCCCCTATT | GACGTCAATG | ACGGTAAATG | GCCCGCCTGG | CATTATGCCC | AGTACATGAC | 420 |
| CTTACGGGAC | TTTCCTACTT | GGCAGTACAT | CTACGTATTA | GTCATCGCTA | TTACCATGGT | 480 |
| GATGCGGTTT | TGGCAGTACA | CCAATGGGCG | TGGATAGCGG | TTTGACTCAC | GGGGATTTCC | 540 |
| AAGTCTCCAC | CCCATTGACG | TCAATGGGAG | TTTGTTTTGG | CACCAAAATC | AACGGGACTT | 600 |
| TCCAAAATGT | CGTAATAACC | CCGCCCCGTT | GACGCAAATG | GGCGGTAGGC | GTGTACGGTG | 660 |
| GGAGGTCTAT | ATAAGCAGAG | CTCGTTTAGT | GAACCGTCAG | ATCGCCTGGA | GACGCCATCC | 720 |
| ACGCTGTTTT | GACCTCCATA | GAAGACACCG | GGACCGATCC | AGCCTCCGCG | GCCGGGAACG | 780 |
| GTGCATTGGA | ACGCGGATTC | CCCGTGCCAA | GAGTGACGTA | AGTACCGCCT | ATAGACTCTA | 840 |
| TAGGCACACC | CCTTTGGCTC | TTATGCATGC | TATACTGTTT | TTGGCTTGGG | GCCTATACAC | 900 |
| CCCCGCTCCT | TATGCTATAG | GTGATGGTAT | AGCTTAGCCT | ATAGGTGTGG | GTTATTGACC | 960 |
| ATTATTGACC | ACTCCCCTAT | TGGTGACGAT | ACTTTCCATT | ACTAATCCAT | AACATGGCTC | 1020 |
| TTTGCCACAA | CTATCTCTAT | TGGCTATATG | CCAATACTCT | GTCCTTCAGA | GACTGACACG | 1080 |
| GACTCTGTAT | TTTTACAGGA | TGGGGTCCAT | TTATTATTTA | CAAATTCACA | TATACAACAA | 1140 |
| CGCCGTCCCC | CGTGCCCGCA | GTTTTTATTA | AACATAGCGT | GGGATCTCCG | ACATCTCGGG | 1200 |
| TACGTGTTCC | GGACATGGGC | TCTTCTCCGG | TAGCGGCGGA | GCTTCCACAT | CCGAGCCCTG | 1260 |
| GTCCCATCCG | TCCAGCGGCT | CATGGTCGCT | CGGCAGCTCC | TTGCTCCTAA | CAGTGGAGGC | 1320 |
| CAGACTTAGG | CACAGCACAA | TGCCCACCAC | CACCAGTGTG | CCGCACAAGG | CCGTGGCGGT | 1380 |
| AGGGTATGTG | TCTGAAAATG | AGCTCGGAGA | TTGGGCTCGC | ACCTGGACGC | AGATGGAAGA | 1440 |
| CTTAAGGCAG | CGGCAGAAGA | AGATGCAGGC | AGCTGAGTTG | TTGTATTCTG | ATAAGAGTCA | 1500 |
| GAGGTAACTC | CCGTTGCGGT | GCTGTTAACG | GTGGAGGGCA | GTGTAGTCTG | AGCAGTACTC | 1560 |

-continued

```
GTTGCTGCCG CGCGCGCCAC CAGACATAAT AGCTGACAGA CTAACAGACT GTTCCTTTCC   1620

ATGGGTCTTT TCTGCAGTCA CCGTCGTCGA CCTAAGAATT CAGACTCGAG CAAGTCTAGA   1680

ATGTGCTGGA GACCCCTGTG TCGGTTCCTG TGGCTTTGGT CCTATCTGTC TTATGTTCAA   1740

GCAGTGCCTA TCCAGAAAGT CCAGGATGAC ACCAAAACCC TCATCAAGAC CATTGTCACC   1800

AGGATCAATG ACATTTCACA CACGCAGTCG GTATCCGCCA AGCAGAGGGT CACTGGCTTG   1860

GACTTCATTC CTGGGCTTCA CCCCATTCTG AGTTTGTCCA AGATGGACCA GACTCTGGCA   1920

GTCTATCAAC AGGTCCTCAC CAGCCTGCCT TCCCAAAATG TGCTGCAGAT AGCCAATGAC   1980

CTGGAGAATC TCCGAGACCT CCTCCATCTG CTGGCCTTCT CCAAGAGCTG CTCCCTGCCT   2040

CAGACCAGTG GCCTGCAGAA GCCAGAGAGC CTGGATGGCG TCCTGGAAGC CTCACTCTAC   2100

TCCACAGAGG TGGTGGCTTT GAGCAGGCTG CAGGGCTCTC TGCAGGACAT TCTTCAACAG   2160

TTGGATGTTA GCCCTGAATG TGAGGATCCA CTACGCGTTA GAGCTCGCTG ATCAGCCTCG   2220

ACTGTGCCTT CTAGTTGCCA GCCATCTGTT GTTTGCCCCT CCCCCGTGCC TTCCTTGACC   2280

CTGGAAGGTG CCACTCCCAC TGTCCTTTCC TAATAAAATG AGGAAATTGC ATCGCATTGT   2340

CTGAGTAGGT GTCATTCTAT TCTGGGGGGT GGGGTGGGGC AGGACAGCAA GGGGGAGGAT   2400

TGGGAAGACA ATAGCAGGGG GGTGGGCGAA GAACTCCAGC ATGAGATCCC CGCGCTGGAG   2460

GATCATCCAG CCGGCGTCCC GGAAAACGAT TCCGAAGCCC AACCTTTCAT AGAAGGCGGC   2520

GGTGGAATCG AAATCTCGTG ATGGCAGGTT GGGCGTCGCT TGGTCGGTCA TTTCGAACCC   2580

CAGAGTCCCG CTCAGAAGAA CTCGTCAAGA AGGCGATAGA AGGCGATGCG CTGCGAATCG   2640

GGAGCGGCGA TACCGTAAAG CACGAGGAAG CGGTCAGCCC ATTCGCCGCC AAGCTCTTCA   2700

GCAATATCAC GGGTAGCCAA CGCTATGTCC TGATAGCGGT CCGCCACACC CAGCCGGCCA   2760

CAGTCGATGA ATCCAGAAAA GCGGCCATTT TCCACCATGA TATTCGGCAA GCAGGCATCG   2820

CCATGGGTCA CGACGAGATC CTCGCCGTCG GGCATGCGCG CCTTGAGCCT GGCGAACAGT   2880

TCGGCTGGCG CGAGCCCCTG ATGCTCTTCG TCCAGATCAT CCTGATCGAC AAGACCGGCT   2940

TCCATCCGAG TACGTGCTCG CTCGATGCGA TGTTTCGCTT GGTGGTCGAA TGGGCAGGTA   3000

GCCGGATCAA GCGTATGCAG CCGCCGCATT GCATCAGCCA TGATGGATAC TTTCTCGGCA   3060

GGAGCAAGGT GAGATGACAG GAGATCCTGC CCCGGCACTT CGCCCAATAG CAGCCAGTCC   3120

CTTCCCGCTT CAGTGACAAC GTCGAGCACA GCTGCGCAAG GAACGCCCGT CGTGGCCAGC   3180

CACGATAGCC GCGCTGCCTC GTCCTGCAGT TCATTCAGGG CACCGGACAG GTCGGTCTTG   3240

ACAAAAAGAA CCGGGCGCCC CTGCGCTGAC AGCCGGAACA CGGCGGCATC AGAGCAGCCG   3300

ATTGTCTGTT GTGCCCAGTC ATAGCCGAAT AGCCTCTCCA CCCAAGCGGC CGGAGAACCT   3360

GCGTGCAATC CATCTTGTTC AATCATGCGA AACGATCCTC ATCCTGTCTC TTGATCAGAT   3420

CTTGATCCCC TGCGCCATCA GATCCTTGGC GGCAAGAAAG CCATCCAGTT TACTTTGCAG   3480

GGCTTCCCAA CCTTACCAGA GGGCGCCCCA GCTGGCAATT CCGGTTCGCT TGCTGTCCAT   3540

AAAACCGCCC AGTCTAGCTA TCGCCATGTA AGCCCACTGC AAGCTACCTG CTTTCTCTTT   3600

GCGCTTGCGT TTTCCCTTGT CCAGATAGCC CAGTAGCTGA CATTCATCCG GGTCAGCAC   3660

CGTTTCTGCG GACTGGCTTT CTACGTGTTC CGCTTCCTTT AGCAGCCCTT GCGCCCTGAG   3720

TGCTTGCGGC AGCGTGAAGC TGTCAATTCC GCGTTAAATT TTTGTTAAAT CAGCTCATTT   3780

TTTAACCAAT AGGCCGAAAT CGGCAAAATC CCTTATAAAT CAAAAGAATA GCCCGAGATA   3840

GGGTTGAGTG TTGTTCCAGT TTGGAACAAG AGTCCACTAT TAAAGAACGT GGACTCCAAC   3900

GTCAAAGGGC GAAAAACCGT CTATCAGGGC GATGGCGGAT CAGCTTATGC GGTGTGAAAT   3960
```

-continued

```
ACCGCACAGA TGCGTAAGGA GAAAATACCG CATCAGGCGC TCTTCCGCTT CCTCGCTCAC    4020

TGACTCGCTG CGCTCGGTCG TTCGGCTGCG GCGAGCGGTA TCAGCTCACT CAAAGGCGGT    4080

AATACGGTTA TCCACAGAAT CAGGGGATAA CGCAGGAAAG AACATGTGAG CAAAAGGCCA    4140

GCAAAAGGCC AGGAACCGTA AAAAGGCCGC GTTGCTGGCG TTTTTCCATA GGCTCCGCCC    4200

CCCTGACGAG CATCACAAAA ATCGACGCTC AAGTCAGAGG TGGCGAAACC CGACAGGACT    4260

ATAAAGATAC CAGGCGTTTC CCCCTGGAAG CTCCCTCGTG CGCTCTCCTG TTCCGACCCT    4320

GCCGCTTACC GGATACCTGT CCGCCTTTCT CCCTTCGGGA AGCGTGGCGC TTTCTCATAG    4380

CTCACGCTGT AGGTATCTCA GTTCGGTGTA GGTCGTTCGC TCCAAGCTGG GCTGTGTGCA    4440

CGAACCCCCC GTTCAGCCCG ACCGCTGCGC CTTATCCGGT AACTATCGTC TTGAGTCCAA    4500

CCCGGTAAGA CACGACTTAT CGCCACTGGC AGCAGCCACT GGTAACAGGA TTAGCAGAGC    4560

GAGGTATGTA GGCGGTGCTA CAGAGTTCTT GAAGTGGTGG CCTAACTACG GCTACACTAG    4620

AAGGACAGTA TTTGGTATCT GCGCTCTGCT GAAGCCAGTT ACCTTCGGAA AAAGAGTTGG    4680

TAGCTCTTGA TCCGGCAAAC AAACCACCGC TGGTAGCGGC GGTTTTTTGT TTGCAAGCAG    4740

CAGATTACGC GCAGAAAAAA AGGATCTCAA GAAGATCCTT TGATCTTTTC TTACTGAACG    4800

GTGATCCCCA CCGGAATT                                                 4818
```